US009477301B2

(12) United States Patent
Kishi

(10) Patent No.: US 9,477,301 B2

(45) Date of Patent: Oct. 25, 2016

(54) OPERATION SUPPORT DEVICE AND ASSEMBLY METHOD THEREOF

(71) Applicant: OLYMPUS CORPORATION, Tokyo (JP)

(72) Inventor: Kosuke Kishi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 100 days.

(21) Appl. No.: 14/151,987

(22) Filed: Jan. 10, 2014

(65) Prior Publication Data

US 2014/0166023 A1 Jun. 19, 2014

Related U.S. Application Data

(63) Continuation of application No. PCT/JP2012/070408, filed on Aug. 3, 2012.

(60) Provisional application No. 61/515,203, filed on Aug. 4, 2011.

(30) Foreign Application Priority Data

Feb. 22, 2012 (JP) ................................ 2012-036226

(51) Int. Cl.

*A61B 19/08* (2006.01)
*G06F 3/01* (2006.01)
(Continued)

(52) U.S. Cl.

CPC ................. *G06F 3/01* (2013.01); *A61B 17/29* (2013.01); *A61B 17/32002* (2013.01);
(Continued)

(58) Field of Classification Search

CPC ................ A61B 19/2203; A61B 2017/00477; A61B 2019/2223; A61B 19/081; A61B 2019/223; A61B 2019/448; A61B 17/3423; A61B 2017/3445; A61B 2019/2215; A61B 2019/2234; A61B 2019/2242; A61B 19/26; A61B 19/5212

USPC ................ 128/849–856; 74/490.01; 600/102
See application file for complete search history.

(56) References Cited

U.S. PATENT DOCUMENTS

| | | |
|---|---|---|
| 3,139,990 A | 7/1964 | Jelatis et al. |
| 3,923,166 A | 12/1975 | Fletcher et al. |

(Continued)

FOREIGN PATENT DOCUMENTS

| | | |
|---|---|---|
| CN | 101027010 A | 8/2007 |
| CN | 101167658 A | 4/2008 |

(Continued)

OTHER PUBLICATIONS

Chinese Office Action dated Jun. 3, 2015 from related Chinese Application No. 201280035926.3, together with an English language translation.

(Continued)

*Primary Examiner* — Michael Brown

(74) *Attorney, Agent, or Firm* — Scully Scott Murphy & Presser, PC

(57) ABSTRACT

An operation support device having a surgical instrument unit and a surgical instrument unit support section, includes: an intermediate member connected to the surgical instrument support section and configured to hold the surgical instrument unit; a shielding member having a hole portion engaged with the intermediate member; and a driving force supply unit installed at the surgical instrument support section. A first space and a second space are formed by an assembly constituted by the shielding member and the intermediate member engaged with the hole portion as a boundary. The intermediate member is connected to the surgical instrument support section at a side of the first space, and holds the surgical instrument unit at a side of the second space. The driving force supply unit and the surgical instrument support section are disposed in the first space.

12 Claims, 27 Drawing Sheets

110 Ac Au 3b T1 3f 13d 13c 11A 12c 7 3b 18 6A 6B 7C 12d 3e T2 11B 11 1a 101c (101) 13 3a 4 5 7a 12A 12 12B 7b O11,O12,O3

(51) Int. Cl.

| | |
|---|---|
| ***A61B 17/29*** | (2006.01) |
| ***A61B 17/32*** | (2006.01) |
| ***A61B 18/14*** | (2006.01) |
| ***B25J 13/02*** | (2006.01) |
| *A61B 17/068* | (2006.01) |
| *A61B 17/00* | (2006.01) |

(52) U.S. Cl.

CPC .......... *A61B 18/1402* (2013.01); *A61B 34/30* (2016.02); *A61B 46/10* (2016.02); *A61B 90/50* (2016.02); *B25J 13/02* (2013.01); *A61B 17/068* (2013.01); *A61B 34/37* (2016.02); *A61B 34/71* (2016.02); *A61B 34/77* (2016.02); *A61B 46/23* (2016.02); *A61B 2017/00119* (2013.01); *A61B 2017/00477* (2013.01); *A61B 2017/00482* (2013.01); *Y10S 901/08* (2013.01); *Y10S 901/09* (2013.01); *Y10S 901/30* (2013.01); *Y10T 29/49826* (2015.01); *Y10T 74/18056* (2015.01)

(56) References Cited

U.S. PATENT DOCUMENTS 4,672,281 A 6/1987 Yagusic et al.
4,830,569 A 5/1989 Jannborg
4,872,803 A 10/1989 Asakawa
5,214,969 A 6/1993 Adkins et al.
5,603,723 A 2/1997 Aranyi et al.
5,632,432 A 5/1997 Schulze et al.
5,649,956 A 7/1997 Jensen et al.
5,656,903 A 8/1997 Shui et al.
5,712,543 A 1/1998 Sjostrom
5,760,530 A 6/1998 Kolesar
5,762,458 A 6/1998 Wang et al.
5,784,542 A 7/1998 Ohm et al.
5,817,119 A 10/1998 Klieman et al.
5,836,869 A 11/1998 Kudo et al.
5,855,583 A 1/1999 Wang et al.
5,871,493 A 2/1999 Sjostrom et al.
5,876,325 A 3/1999 Mizuno et al.
6,007,550 A 12/1999 Wang et al.
6,063,095 A 5/2000 Wang et al.
6,082,797 A 7/2000 Antonette
6,090,122 A 7/2000 Sjostrom et al.
6,102,850 A 8/2000 Wang et al.
6,132,368 A 10/2000 Cooper
6,132,441 A 10/2000 Grace
6,206,903 B1 3/2001 Ramans
6,246,200 B1 6/2001 Blumenkranz et al.
6,328,752 B1 12/2001 Sjostrom et al.
6,346,072 B1 2/2002 Cooper
6,430,473 B1 8/2002 Lee et al.
6,436,107 B1 8/2002 Wang et al.
6,441,577 B2 8/2002 Blumenkranz et al.
6,557,558 B1 5/2003 Tajima et al.
6,574,355 B2 6/2003 Green
6,587,750 B2 7/2003 Gerbi et al.
6,602,185 B1 8/2003 Uchikubo
6,645,196 B1 11/2003 Nixon et al.
6,666,876 B2 12/2003 Kawai et al.
6,676,684 B1 1/2004 Morley et al.
6,685,698 B2 2/2004 Morley et al.
6,699,177 B1 3/2004 Wang et al.
6,746,443 B1 6/2004 Morley et al.
6,783,524 B2 8/2004 Anderson et al.
6,786,896 B1 9/2004 Madhani et al.
6,853,879 B2 2/2005 Sunaoshi
6,866,671 B2 3/2005 Tierney et al.
6,905,460 B2 6/2005 Wang et al.
6,913,613 B2 7/2005 Schwarz et al.
7,083,571 B2 8/2006 Wang et al.
7,101,363 B2 9/2006 Nishizawa et al.
7,107,124 B2 9/2006 Green
7,118,582 B1 10/2006 Wang et al.
7,273,488 B2 9/2007 Nakamura et al.
7,295,893 B2 11/2007 Sunaoshi
7,313,464 B1 12/2007 Perreault et al.
7,331,967 B2 2/2008 Lee et al.
7,357,774 B2 4/2008 Cooper
7,373,219 B2 5/2008 Nowlin et al.
7,422,592 B2 9/2008 Morley et al.
7,476,237 B2 1/2009 Taniguchi et al.
7,549,998 B2 6/2009 Braun
7,594,912 B2 * 9/2009 Cooper .............. A61B 19/2203 600/102
7,608,083 B2 10/2009 Lee et al.
7,654,431 B2 2/2010 Hueil et al.
7,666,191 B2 2/2010 Orban, III et al.
7,674,255 B2 3/2010 Braun
7,695,481 B2 4/2010 Wang et al.
7,699,835 B2 4/2010 Lee et al.
7,699,855 B2 4/2010 Anderson et al.
7,778,733 B2 8/2010 Nowlin et al.
7,819,884 B2 10/2010 Lee et al.
7,819,885 B2 10/2010 Cooper
7,862,579 B2 1/2011 Ortiz et al.
7,865,266 B2 1/2011 Moll et al.
7,955,321 B2 6/2011 Kishi et al.
8,105,320 B2 1/2012 Manzo
8,155,479 B2 4/2012 Hoffman et al.
8,267,958 B2 9/2012 Braun
8,350,806 B2 1/2013 Nagasaka et al.
8,423,186 B2 4/2013 Itkowitz et al.
8,460,277 B2 * 6/2013 Suarez ............ A61B 17/32002 200/334
8,496,647 B2 7/2013 Blumenkranz et al.
8,540,748 B2 9/2013 Murphy et al.
8,744,137 B2 6/2014 Sakai et al.
8,845,681 B2 9/2014 Grace
8,876,858 B2 11/2014 Braun
8,888,789 B2 11/2014 Prisco et al.
8,903,549 B2 12/2014 Itkowitz et al.
8,906,002 B2 12/2014 Kishi et al.
9,039,681 B2 5/2015 Wang et al.
9,283,675 B2 3/2016 Hager et al.
9,308,009 B2 4/2016 Madan et al.
9,308,646 B2 4/2016 Lim et al.
2001/0021859 A1 9/2001 Kawai et al.
2001/0055062 A1 12/2001 Shioda et al.
2002/0072736 A1 6/2002 Tierney et al.
2002/0091374 A1 7/2002 Cooper
2002/0128552 A1 9/2002 Nowlin et al.
2003/0033024 A1 2/2003 Sunaoshi
2003/0060927 A1 3/2003 Gerbi et al.
2003/0069471 A1 4/2003 Nakanishi et al.
2003/0083648 A1 5/2003 Wang et al.
2003/0100817 A1 5/2003 Wang et al.
2003/0216723 A1 11/2003 Shinmura et al.
2004/0049205 A1 3/2004 Lee et al.
2004/0092912 A1 5/2004 Jinno et al.
2004/0111113 A1 6/2004 Nakamura et al.
2004/0140787 A1 7/2004 Okamoto et al.
2004/0186345 A1 9/2004 Yang et al.
2004/0186624 A1 9/2004 Oda et al.
2004/0243147 A1 12/2004 Lipow
2004/0246469 A1 12/2004 Hirose
2005/0020876 A1 1/2005 Shioda et al.
2005/0021050 A1 1/2005 Cooper
2005/0033117 A1 2/2005 Ozaki et al.
2005/0125027 A1 6/2005 Knodel et al.
2005/0149003 A1 7/2005 Tierney et al.
2005/0228365 A1 10/2005 Wang et al.
2005/0273086 A1 12/2005 Green et al.
2006/0052664 A1 3/2006 Julian et al.
2006/0074408 A1 4/2006 Jinno et al.
2006/0079865 A1 4/2006 Jinno et al.
2006/0079866 A1 4/2006 Jinno et al.
2006/0087746 A1 4/2006 Lipow
2006/0116973 A1 6/2006 Okamoto et al.
2006/0149162 A1 7/2006 Daw et al.
2006/0155262 A1 7/2006 Kishi et al.
2006/0161138 A1 7/2006 Orban, III et al.
2006/0190031 A1 8/2006 Wales et al.

(56) References Cited

U.S. PATENT DOCUMENTS

2006/0235436 A1 10/2006 Anderson et al.
2007/0012135 A1 1/2007 Tierney et al.
2007/0089557 A1* 4/2007 Solomon ............ A61B 19/2203 74/490.01
2007/0119274 A1 5/2007 Devengenzo et al.
2007/0137372 A1 6/2007 Devengenzo et al.
2007/0138992 A1 6/2007 Prisco et al.
2007/0142823 A1 6/2007 Prisco et al.
2007/0142825 A1 6/2007 Prisco et al.
2007/0156122 A1 7/2007 Cooper
2007/0167679 A1 7/2007 Miyamoto et al.
2007/0167680 A1 7/2007 Miyamoto et al.
2007/0173689 A1 7/2007 Ozaki et al.
2007/0197896 A1 8/2007 Moll et al.
2007/0208375 A1 9/2007 Nishizawa et al.
2007/0219668 A1 9/2007 Takahashi et al.
2007/0225550 A1 9/2007 Gattani et al.
2007/0249897 A1 10/2007 Miyamoto et al.
2007/0265638 A1 11/2007 Lipow et al.
2008/0015611 A1 1/2008 Jinno et al.
2008/0033240 A1 2/2008 Hoffman et al.
2008/0046122 A1 2/2008 Manzo et al.
2008/0051631 A1 2/2008 Dejima et al.
2008/0059131 A1 3/2008 Tokita et al.
2008/0103524 A1 5/2008 Grace
2008/0140088 A1 6/2008 Orban, III
2008/0147091 A1 6/2008 Cooper
2008/0177285 A1 7/2008 Brock et al.
2008/0204425 A1 8/2008 Nagasaka et al.
2008/0215065 A1 9/2008 Wang et al.
2008/0228196 A1 9/2008 Wang et al.
2008/0234866 A1 9/2008 Kishi et al.
2008/0243142 A1 10/2008 Gildenberg
2008/0262654 A1 10/2008 Omori et al.
2008/0287735 A1 11/2008 Takemoto et al.
2008/0312668 A1 12/2008 Grace
2009/0018700 A1 1/2009 Okamoto et al.
2009/0022262 A1 1/2009 Ohishi
2009/0030273 A1 1/2009 Murakami
2009/0034820 A1 2/2009 Sugiyama
2009/0036736 A1 2/2009 Dejima et al.
2009/0036902 A1 2/2009 DiMaio et al.
2009/0046146 A1 2/2009 Hoyt
2009/0057369 A1 3/2009 Smith et al.
2009/0088634 A1 4/2009 Zhao et al.
2009/0088773 A1 4/2009 Zhao et al.
2009/0088897 A1 4/2009 Zhao et al.
2009/0132088 A1 5/2009 Taitler
2009/0163948 A1 6/2009 Sunaoshi et al.
2009/0171147 A1 7/2009 Lee et al.
2009/0182193 A1 7/2009 Whitman et al.
2009/0193299 A1 7/2009 Sekiguchi et al.
2009/0204911 A1 8/2009 Sekiguchi et al.
2009/0247877 A1 10/2009 Tanaka et al.
2009/0281378 A1 11/2009 Banju et al.
2009/0326318 A1 12/2009 Tognaccini et al.
2010/0010673 A1 1/2010 Wang et al.
2010/0013812 A1 1/2010 Gu et al.
2010/0087835 A1 4/2010 Blumenkranz et al.
2010/0160728 A1 6/2010 Yoshie
2010/0163057 A1 7/2010 Anderson et al.
2010/0174293 A1 7/2010 Orban, III et al.
2010/0217284 A1 8/2010 Grace
2010/0217528 A1 8/2010 Sato et al.
2010/0225209 A1 9/2010 Goldberg et al.
2010/0228264 A1 9/2010 Robinson et al.
2010/0228265 A1 9/2010 Prisco
2010/0234857 A1 9/2010 Itkowitz et al.
2010/0274087 A1 10/2010 Diolaiti et al.
2010/0291520 A1 11/2010 Kurenov et al.
2010/0317965 A1 12/2010 Itkowitz et al.
2010/0318099 A1 12/2010 Itkowitz et al.
2010/0318101 A1 12/2010 Choi
2010/0332031 A1 12/2010 Itkowitz et al.
2011/0015650 A1 1/2011 Choi et al.
2011/0050852 A1 3/2011 Lamprecht et al.
2011/0118707 A1 5/2011 Burbank
2011/0118748 A1 5/2011 Itkowitz
2011/0118753 A1 5/2011 Itkowitz et al.
2011/0137337 A1 6/2011 van den Dool et al.
2011/0190932 A1 8/2011 Tsusaka et al.
2011/0230894 A1 9/2011 Simaan et al.
2011/0238079 A1 9/2011 Hannaford et al.
2011/0276058 A1 11/2011 Choi et al.
2011/0279374 A1 11/2011 Park et al.
2011/0282493 A1 11/2011 Ortmaier
2011/0288579 A1 11/2011 Hyodo
2011/0306952 A1 12/2011 Chen et al.
2012/0071752 A1 3/2012 Sewell et al.
2012/0165828 A1 6/2012 Duque et al.
2012/0191245 A1 7/2012 Fudaba et al.

FOREIGN PATENT DOCUMENTS

CN 101426412 A 5/2009
DE 10 2008 041 867 A1 3/2010
EP 0 677 278 A1 10/1995
EP 1 728 475 A2 12/2006
EP 2 092 875 A1 8/2009
EP 2 298 220 A1 3/2011
EP 2 332 484 A2 6/2011
JP 63-029810 A 2/1988
JP 64-034688 A 2/1989
JP 01-271185 A 10/1989
JP 02-071980 A 3/1990
JP 02-292193 A 12/1990
JP 03-161289 A 7/1991
JP 05-096477 A 4/1993
JP 5-329784 A 12/1993
JP 07-001366 A 1/1995
JP 07-194609 A 8/1995
JP 07-241300 A 9/1995
JP 07-246578 A 9/1995
JP 07-096182 B2 10/1995
JP 8-66883 A 3/1996
JP 08-215204 A 8/1996
JP 08-243080 A 9/1996
JP H10-502265 A 3/1998
JP 10-128538 A 5/1998
JP 11-300662 A 11/1999
JP 2000-312684 A 11/2000
JP 2001-087281 A 4/2001
JP 2001-113481 A 4/2001
JP 2001-277157 A 10/2001
JP 2001-309920 A 11/2001
JP 2002-014287 A 1/2002
JP 2002-059380 A 2/2002
JP 2002-102248 A 4/2002
JP 2002-272758 A 9/2002
JP 2002-537884 A 11/2002
JP 2003-024336 A 1/2003
JP 2003-053685 A 2/2003
JP 2003-250812 A 9/2003
JP 2003-265500 A 9/2003
JP 2003-340752 A 12/2003
JP 2004-105451 A 4/2004
JP 2004-114201 A 4/2004
JP 2005-511185 A 4/2005
JP 2005-192743 A 7/2005
JP 3686947 B2 8/2005
JP 2005-261827 A 9/2005
JP 2005-312991 A 11/2005
JP 2006-061272 A 3/2006
JP 2006-167867 A 6/2006
JP 2006-288955 A 10/2006
JP 2006-321027 A 11/2006
JP 2007-029274 A 2/2007
JP 2007-038315 A 2/2007
JP 2007-98507 A 4/2007
JP 2007-105485 A 4/2007
JP 3999816 B2 10/2007
JP 2008-000282 A 1/2008
JP 2008-036793 A 2/2008
JP 4058113 B2 3/2008

(56) References Cited

FOREIGN PATENT DOCUMENTS

| | | | |
|---|---|---|---|
| JP | 2008-093270 | A | 4/2008 |
| JP | 2008-104854 | A | 5/2008 |
| JP | 2008-514357 | A | 5/2008 |
| JP | 2008-173724 | A | 7/2008 |
| JP | 4129313 | B2 | 8/2008 |
| JP | 4176126 | B2 | 11/2008 |
| JP | 2009-028157 | A | 2/2009 |
| JP | 2009-056164 | A | 3/2009 |
| JP | 2009-512514 | A | 3/2009 |
| JP | 2009-520573 | A | 5/2009 |
| JP | 2009-178230 | A | 8/2009 |
| JP | 2009-178541 | A | 8/2009 |
| JP | 2009-530037 | A | 8/2009 |
| JP | 2009-195694 | A | 9/2009 |
| JP | 2009-226029 | A | 10/2009 |
| JP | 2009-226093 | A | 10/2009 |
| JP | 2009-269127 | A | 11/2009 |
| JP | 2010-504127 | A | 2/2010 |
| JP | 2010-076012 | A | 4/2010 |
| JP | 2010-524548 | A | 7/2010 |
| JP | 2011-509112 | A | 3/2011 |
| JP | 2011-206213 | A | 10/2011 |
| JP | 2012-000199 | A | 1/2012 |
| JP | 2012-091310 | A | 5/2012 |
| WO | 96/00044 | A1 | 1/1996 |
| WO | 97/16123 | A1 | 5/1997 |
| WO | 97/16124 | A1 | 5/1997 |
| WO | 97/29690 | A1 | 8/1997 |
| WO | 98/25666 | A1 | 6/1998 |
| WO | 00/51486 | A1 | 9/2000 |
| WO | 00/60421 | A2 | 10/2000 |
| WO | 03/049596 | A2 | 6/2003 |
| WO | 2006/039092 | A2 | 4/2006 |
| WO | 2006/111966 | A2 | 10/2006 |
| WO | 2007/047782 | A2 | 4/2007 |
| WO | 2007/075864 | A1 | 7/2007 |
| WO | 2007/111955 | A2 | 10/2007 |
| WO | 2007/126443 | A2 | 11/2007 |
| WO | 2007/138674 | A1 | 12/2007 |
| WO | 2008/038184 | A2 | 4/2008 |
| WO | 2008/108289 | A1 | 9/2008 |
| WO | 2009/034477 | A2 | 3/2009 |
| WO | 2009/089614 | A1 | 7/2009 |
| WO | 2010/006057 | A1 | 1/2010 |
| WO | 2010/093152 | A2 | 8/2010 |
| WO | 2010/109932 | A1 | 9/2010 |
| WO | 2010/126127 | A1 | 11/2010 |
| WO | 2011/025786 | A1 | 3/2011 |
| WO | 2011/060139 | A2 | 5/2011 |
| WO | 2011/060185 | A1 | 5/2011 |
| WO | 2011/060187 | A1 | 5/2011 |
| WO | 2011/085815 | A1 | 7/2011 |
| WO | 2012/042949 | A1 | 4/2012 |

OTHER PUBLICATIONS

Chinese Office Action dated Jul. 1, 2015 from related Chinese Application No. 201280037244.6, together with an English language translation.

Extended Supplementary European Search Report dated Jul. 1, 2015 from related European Application No. 12 82 0066.4.

Extended Supplementary European Search Report dated Jul. 2, 2015 from related European Application No. 12 81 9672.2.

Extended Supplementary European Search Report dated Jul. 23, 2015 from related European Application No. 12 81 9455.2.

English Abstract of JP 01-234140 dated Sep. 19, 1989.

International Search Report dated Oct. 23, 2012 issued in PCT/JP2012/070414.

International Search Report dated Sep. 4, 2012 issued in PCT/JP2012/070408.

International Search Report dated Aug. 28, 2012 issued in PCT/JP2012/069927.

International Search Report dated Sep. 4, 2012 issued in PCT/JP2012/070415.

International Search Report dated Oct. 16, 2012 issued in PCT/JP2012/070581.

International Search Report dated Nov. 13, 2012 issued in PCT/JP2012/070576.

International Search Report dated Sep. 18, 2012 issued in PCT/JP2012/070417.

International Search Report dated Oct. 30, 2012 issued in PCT/JP2012/070418.

International Search Report dated Sep. 11, 2012 issued in PCT/JP2012/070416.

International Search Report dated Sep. 18, 2012 issued in PCT/JP2012/070407.

International Search Report dated Sep. 18, 2012 issued in PCT/JP2012/069868.

International Search Report dated Nov. 6, 2012 issued in PCT/JP2012/069919.

International Search Report dated Sep. 11, 2012 issued in PCT/JP2012/069696.

U.S. Office Action dated Apr. 9, 2015 received, namely U.S. Appl. No. 14/169,675.

U.S. Office Action dated May 8, 2015 received, namely U.S. Appl. No. 14/157,920.

Notice of Allowance dated Jan. 20, 2015 from U.S. Appl. No. 13/566,023.

Notice of Allowance dated Jan. 29, 2015 from U.S. Appl. No. 14/168,551.

Extended Supplementary European Search Report dated Feb. 12, 2015 from related European Application No. 12 81 9447.9.

Extended Supplementary European Search Report dated Feb. 13, 2015 from related European Application No. 12 82 0679.4.

Supplementary European Search Report dated Feb. 18, 2015 from related European Application No. 12 82 0758.6.

Extended Supplementary European Search Report dated Feb. 23, 2015 from related European Application No. 12 81 9877.7.

Extended Supplementary European Search Report dated Feb. 23, 2015 from related European Application No. 12 82 0239.7.

Partial Supplementary European Search Report dated Feb. 26, 2015 from related European Application No. 12 82 0066.4.

Partial Supplementary European Search Report dated Feb. 27, 2015 from related European Application No. 12 81 9672.2.

Extended Supplementary European Search Report dated Mar. 2, 2015 from related European Application No. 12 82 0017.7.

Extended Supplementary European Search Report dated Mar. 16, 2015 from related European Application No. 12 82 0479.9.

Extended Supplementary European Search Report dated Mar. 16, 2015 from related European Application No. 12 81 9504.7.

Extended Supplementary European Search Report dated Mar. 16, 2015 from related European Application No. 12 81 9398.4.

Office Action dated Mar. 25, 2015 received, namely U.S. Appl. No. 14/169,321.

Extended Supplementary European Search Report dated Mar. 27, 2015 from related European Application No. 12 82 0056.5.

Office Action dated Nov. 19, 2015 received, namely U.S. Appl. No. 14/157,920.

Japanese Office Action dated Jan. 19, 2016 from related Japanese Patent Application No. 2012-036226, together with an English language translation.

Office Action dated Mar. 24, 2016 received in U.S. Appl. No. 13/566,047.

Office Action dated Feb. 22, 2016 received in U.S. Appl. No. 14/168,496.

Office Action dated Mar. 10, 2016 received in U.S. Appl. No. 13/566,012.

Office Action dated Sep. 16, 2015 received, namely U.S. Appl. No. 13/566,012.

Office Action dated Oct. 19, 2015 received, namely U.S. Appl. No. 14/168,525.

Japanese Office Action dated Apr. 26, 2016 from related Japanese Patent Application No. 2012-157788.

Japanese Office Action dated Apr. 26, 2016 from related Japanese Patent Application No. 2012-154945.

(56) References Cited

OTHER PUBLICATIONS

Notice of Allowance dated Apr. 22, 2016 issued in U.S. Appl. No. 14/157,920.
Office Action dated Jun. 16, 2016 received in related U.S. Appl. No. 14/169,742.
European Patent Office Communication dated May 23, 2016 in related European Application No. 12 819 877.7.
Office Action dated May 9, 2016 received in related U.S. Appl. No. 14/170,856.
Japanese Office Action dated Jun. 14, 2016 in related Japanese Patent Application No. 2012-012104.

* cited by examiner

O1
1A
1
1B
Ac
1a
2
2A
2B
ac
7b
7
AU
6D
6C
7a
8
3b
3c
3
3d
3a
2c
4
2d
5
3b
6A
6B
O2,O3

21
21a
21e
21g
21A
21B
21b
21C
21c
21d
C12
22
22a
22A
22B
22g
22b
C21
C23
23
23a
23b
23c
23d
23A
23B
23C
23D
24
25
32A
32B
C32
35a
35b
4
5
6A
6C
6D
7
7C
7D
O21,O22,O23

Ac
$A_U$
6A
6B
$S_2$
23d
22d
$S_2$
23a
22c
23
$S_1$
7b
7a
7
8
23A
6D
6C
22
22A
22B
22a
101c
(101)

21
21A (21Aχ)
21A (21Aγ)
21C (21Cχ)
21C (21Cγ)
29
29B
29D
29A
21f
29d (29dχ)
29d (29dγ)
29C (29Cχ)
29C (29Cγ)
29c (29cγ)
21m
21j (21jχ)
29c (29cχ)
21B (21Bχ)
21a
21B (21Bγ)
21j (21jγ)

OPERATION SUPPORT DEVICE AND ASSEMBLY METHOD THEREOF

This application is a continuation application based on a PCT Patent Application No. PCT/JP2012/070408, filed Aug. 3, 2012, whose priority is claimed on both U.S. Provisional Application No. 61/515,203, filed on Aug. 4, 2011, and Japanese Patent Application No. 2012-036226, filed on Feb. 22, 2012. The contents of all of the PCT Application, the US Provisional Application, and the Japanese Application are incorporated herein by reference.

BACKGROUND OF THE INVENTION

1. Field of the Invention

The present invention relates to an operation support device and an assembly method thereof.

2. Description of Related Art

In the related art, in order to support a surgical operation, an operation support device in which a surgical instrument unit is supported by a surgical instrument unit support section is well known.

In such an operation support device, in order to prevent contamination to a patient or a treated subject (hereinafter, simply referred to as a subject) or contamination from the subject, sterilization treatment is performed on an area in contact with or adjacent to the subject. However, for example, it is difficult to perform the sterilization treatment on a unit in which a mechanism requiring electric control such as a motor is disposed. For this reason, such a unit is covered by a sterilization drape to be treated as an unclean area (a non-sterilization field). Then, a clean area (a sterilization field) in which a unit subjected to the sterilization treatment is disposed is provided outside the sterilization drape.

For example, Japanese Patent No. 4058113 discloses "a robot surgical operation system configured to perform a treatment sequence in a sterilized field, the system includes surgical operation equipment, a manipulator assembly including a manipulator arm having a proximal end portion and a distal end portion, a sterilized drape configured to cover at least the manipulator arm of the manipulator assembly and block the manipulator arm from the sterilized field, and an adapter configured to connect the distal end portion of the manipulator arm to the surgical operation equipment and transmit at least secondary movement from the manipulator assembly to the equipment, wherein the adapter extends through the sterilized drape and includes one or more electric connectors configured to transmit an electrical signal from the manipulator arm to the surgical operation equipment and from the surgical operation equipment to the manipulator arm."

That is, Japanese Patent No. 4058113 discloses a medical manipulator in which a hole is formed in the drape covering the manipulator arm, the adapter is mounted on the manipulator arm via the hole, and a treatment tool unit is mounted on the adapter.

In the medical manipulator disclosed in Japanese Patent No. 4058113, in order to distinguish an unclean area from a clean area, sterilization treatment is performed on the adapter exposed to the outside from the hole of the drape and the treatment tool unit mounted on the adapter, and thereby the clean area being formed.

SUMMARY OF THE INVENTION

According to a first aspect of the present invention, an operation support device has a surgical instrument unit and a surgical instrument unit support section configured to detachably support the surgical instrument unit. The operation support device includes: a sterilizable intermediate member rotatably connected to the surgical instrument support section and configured to detachably hold the surgical instrument unit; a sterilizable shielding member having at least one hole portion engaged with the intermediate member; and a driving force supply unit installed at the surgical instrument support section and configured to supply a driving force to the surgical instrument unit via the intermediate member. A first space and a second space are formed by an assembly constituted by the shielding member and the intermediate member engaged with the hole portion of the shielding member as a boundary. The intermediate member is detachably connected to the surgical instrument support section at a side of the first space. The intermediate member detachably holds the surgical instrument unit at a side of the second space. The driving force supply unit and the surgical instrument support section are disposed in the first space.

According to a second aspect of the present invention, in the operation support device according to the first aspect of the present invention, as at least the intermediate member is rotated, a rotary driving force may be supplied to the surgical instrument unit.

According to a third aspect of the present invention, in the operation support device according to the first aspect or the second aspect of the present invention, at least a pair of hole portions may be provided. The intermediate member may have a through-hole portion, into which the surgical instrument unit is inserted, provided to pass through the pair of hole portions and constituting a part of the second space.

According to a fourth aspect of the present invention, in the operation support device according to the third aspect of the present invention, the through-hole portion may have a detachable sterilized sheath.

According to a fifth aspect of the present invention, in the operation support device according to any one of the first aspect to the fourth aspect of the present invention, the driving force supply unit may have at least a linear driving force supply unit configured to advance and retract a drive shaft section in a certain direction to supply a linear driving force. The intermediate member may have at least a linear driving transmission shaft section movably installed in the same direction as the drive shaft section. The surgical instrument unit may be driven by the linear driving force received from the linear driving transmission shaft section.

According to a sixth aspect of the present invention, in the operation support device according to any one of the first aspect to the fifth aspect of the present invention, the intermediate member and the surgical instrument unit may be detachably installed to advance and retract with respect to the hole portion in a certain axial direction.

According to a seventh aspect of the present invention, in the operation support device according to the sixth aspect of the present invention, the intermediate member and the driving force supply unit may be detachably installed in the axial direction.

According to an eighth aspect of the present invention, in the operation support device according to any one of the first aspect to the seventh aspect of the present invention, the shielding member may include a drape and a frame member joined with the drape. The hole portion on which the intermediate member is mounted may be formed at an inner circumferential portion of the frame member.

According to a ninth aspect of the present invention, in the operation support device according to the eighth aspect of the present invention, the frame member joined with the drape may be detachably installed with respect to the driving force transmission section.

According to a tenth aspect of the present invention, in the operation support device according to any one of the first aspect to the seventh aspect of the present invention, the shielding member may include a drape and a coated housing joined with the drape. The hole portion through which the intermediate member is capable of passing may be formed at the coated housing.

According to an eleventh aspect of the present invention, in the operation support device according to the tenth aspect of the present invention, the coated housing joined with the drape may be detachably installed with respect to the driving force transmission section.

According to a twelfth aspect of the present invention, an assembly method of an operation support device is an assembly method of an operation support device having a surgical instrument unit and a surgical instrument unit support section configured to detachably support the surgical instrument unit. The operation support device includes: a sterilizable intermediate member rotatably connected to the surgical instrument support section and configured to detachably hold the surgical instrument unit; a sterilizable shielding member having at least one hole portion engaged with the intermediate member; and a driving force supply unit installed at the surgical instrument support section and configured to supply a driving force to the surgical instrument unit via the intermediate member. The assembly method of the operation support device includes: a shielding member disposing process of disposing the shielding member to cover the driving force supply unit and the surgical instrument support section; a first connecting process of engaging the hole portion of the shielding member with the intermediate member to form an assembly, positioning the driving force supply unit and the surgical instrument support section in a first space using the assembly as a boundary, and detachably connecting the intermediate member and the surgical instrument support section in a side of the first space; and a second connecting process of detachably holding the intermediate member and the surgical instrument unit in a side of a second space opposite to the first space using the assembly as a boundary.

DETAILED DESCRIPTION OF THE INVENTION

Figure 1:
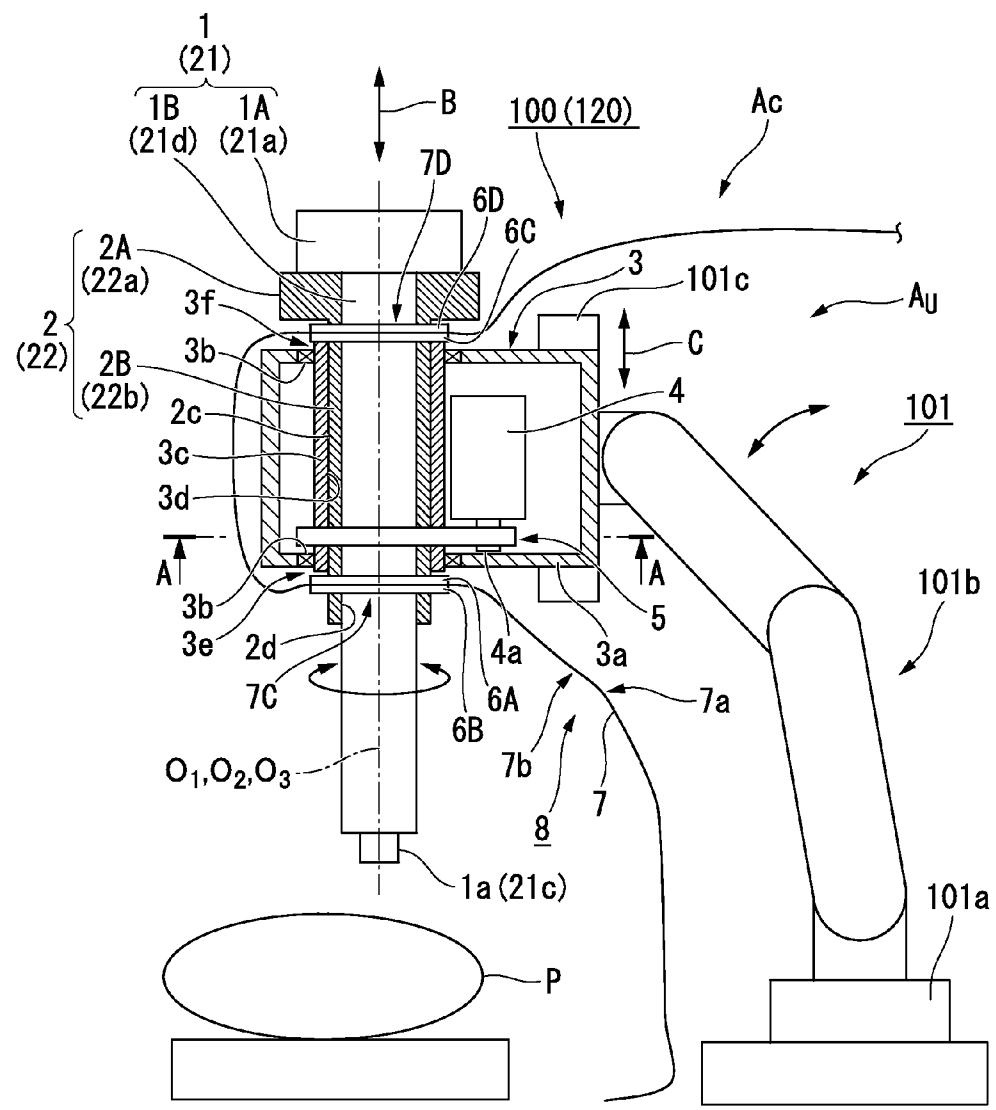
FIG. 1 is a schematic partial cross-sectional view showing a configuration of an operation support device according to a first embodiment of the present invention.

Hereinafter, embodiments of the present invention will be described with reference to the accompanying drawings. Throughout the drawings, even in different embodiments, like or similar members are designated by same reference numerals, and description thereof will not be repeated.

First Embodiment

An operation support device according to a first embodiment of the present invention will be described.

Figure 2:
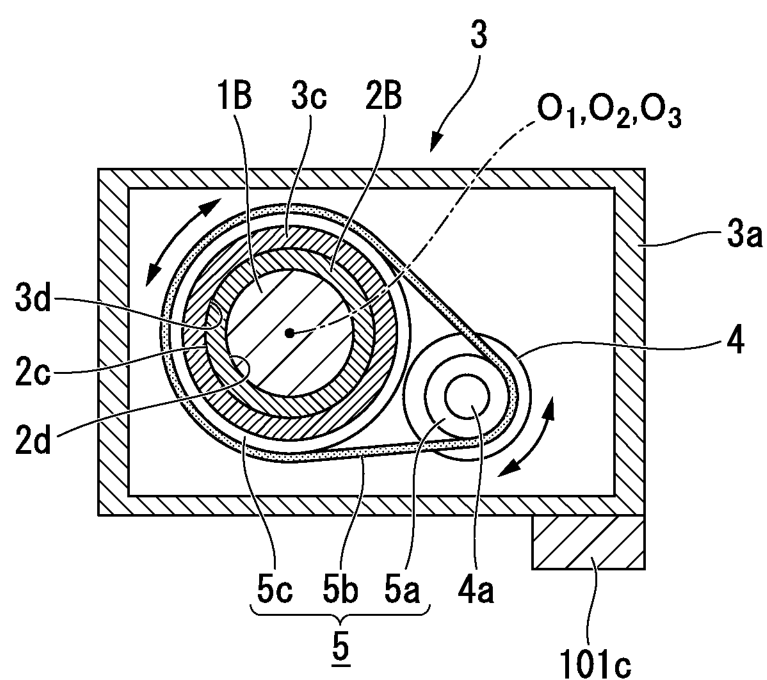
FIG. 2 is a cross-sectional view taken along line A-A of FIG. 1.
Figure 3:
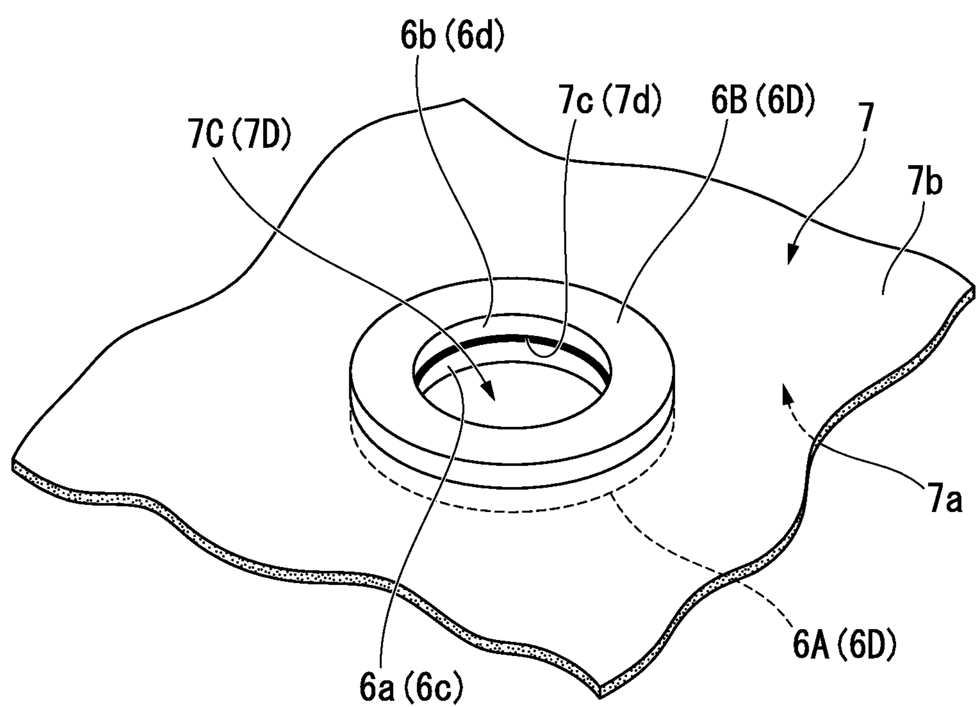
FIG. 3 is a schematic perspective view showing a configuration of a shielding member of the operation support device according to the first embodiment of the present invention.

FIG. 1 is a schematic partial cross-sectional view showing a configuration of the operation support device according to the first embodiment of the present invention. FIG. 2 is a cross-sectional view taken along line A-A of FIG. 1. FIG. 3 is a schematic perspective view showing a configuration of a shielding member of the operation support device according to the first embodiment of the present invention.

As shown in FIG. 1, for example, in a surgical operation, an operation support device 100 according to the present embodiment is an apparatus for manipulating a surgical instrument or moving the surgical instrument in a state in which the surgical instrument is disposed at an appropriate position such as a body cavity of a patient P, or the like.

The operation support device 100 includes a surgical instrument unit support section 101, a surgical instrument driving unit 3 (a driving force supply unit), an intermediate member 2, a treatment tool unit 1 (a surgical instrument unit), and a drape 7 (a shielding member). The surgical instrument driving unit 3 and the intermediate member 2, and the intermediate member 2 and the treatment tool unit 1 are detachably connected in an axial direction as shown by an arrow B. Accordingly, the surgical instrument driving unit 3 (the driving force supply unit), the intermediate member 2, and the treatment tool unit 1 configure a substantially shaft-shaped exterior extending from a proximal end side to a distal end side upon connection as a whole.

Here, the distal end side of the operation support device 100 is a side directed to the body cavity of the patient in use, and the proximal end side is an opposite side thereof.

Hereinafter, in particular, when a relative positional relation among the surgical instrument driving unit 3, the intermediate member 2, and the treatment tool unit 1 (surgical instrument unit) in a connection state in a longitudinal direction is shown, a distal end side, a proximal end side, a distal end portion, a proximal end portion, and so on are referred to with the same meanings as described above unless specifically indicated otherwise.

In addition, when directions related to members such as a tubular shape, a column shape, a shaft shape, or the like, in which a central axis can be specified, are described, a direction along the central axis may be referred to as an axial direction, a direction circling about the central axis may be referred to as a circumferential direction, and a direction perpendicular to the central axis may be referred to as a radial direction.

The surgical instrument unit support section 101 is configured to detachably support the treatment tool unit 1 via the surgical instrument driving unit 3. In the present embodiment, the surgical instrument unit support section 101 includes a base 101*a*, a multi-joint arm 101*b* installed on the base 101*a*, and a linear driving moving section 101*c* connected to an end portion of the multi-joint arm 101*b* opposite to the base 101*a*.

The multi-joint arm 101*b* is configured by appropriately assembling arms connected to joints that can perform movement having multiple degrees of freedom such as rotation, linear driving, or the like, by a drive unit (not shown) such as a motor, or the like. For this reason, as the multi-joint arm 101*b* is manipulated by a manipulation unit (not shown), a position and an orientation of the linear driving moving section 101*c* with respect to the base 101*a* can be varied.

For example, the multi-joint arm 101*b* may be a slave arm of a master slave type medical manipulator system. In this case, since the surgical instrument driving unit 3 is electrically connected to a control unit of the medical manipulator system and configured to perform a motion based on a control signal from a master arm, the surgical instrument driving unit 3 can configure a part of a slave arm.

The surgical instrument unit support section 101 includes a movable part or an electric circuit. For this reason, in the present embodiment, sterilization treatment by, for example, vapor, heat, pressure, or chemicals, or the like (hereinafter, simply referred to as sterilization treatment), is not performed on the entire surgical instrument unit support section 101. However, in the surgical instrument unit support section 101, a sterilization treatment may be appropriately performed on an area in which the sterilization treatment can be easily performed.

The surgical instrument driving unit 3 is a member configured to generate displacement or a force (hereinafter, simply referred to as "a driving force") for operating the treatment tool unit 1 based on a control signal from drive control unit (not shown) and to transmit the driving force to the treatment tool unit 1 via the intermediate member 2.

In the present embodiment, the surgical instrument driving unit 3 is configured to supply the driving force to rotate the treatment tool unit 1 about a central axis $O_1$ thereof.

The surgical instrument driving unit 3 includes a support section 3*a* supported by the linear driving moving section 101*c* to enable movement in one direction, a shaft rotating member 3*c* supported to enable rotation about a certain central axis $O_3$ with respect to the support section 3*a*, a motor 4, and a transmission mechanism 5.

The support section 3*a* may have an appropriate shape such as a box shape, a plate shape, a block shape, or the like, as long as the shaft rotating member 3*c* can be rotatably supported.

In the present embodiment, as an example, the support section 3*a* is formed in a box shape. Through-holes are formed in the support section 3*a* at coaxial positions in two opposite side surfaces thereof. The through-holes are coaxially formed, and outer rings of bearings 3*b* are fixed to inner circumferential portions of the through-holes.

The shaft rotating member 3*c* has an outer diameter such that the shaft rotating member 3*c* is inserted into inner rings of the bearings 3*b* to be fixed to the bearings 3*b*. The shaft rotating member 3*c* is a tubular member having a through-hole portion 3*d* formed therein, which becomes coaxial with a rotation central axis of the bearing 3*b*. A length of the shaft rotating member 3*c* is a length protruding outward slightly more than the support section 3*a*, in a state in which a proximal end portion 3*f* and a distal end portion 3*e* are fitted into the inner rings of the bearings 3*b*, respectively.

In addition, while not specifically shown in FIG. 1, flange portions or fixing members are formed at end portions of the shaft rotating member 3*c* to lock or fix the inner rings of the bearings 3*b*.

For this reason, the shaft rotating member 3*c* is rotatably supported by the support section 3*a* via the bearings 3*b*. A rotation central axis of the shaft rotating member 3*c* restricted by rotation central axes of the bearings 3*b* is referred to as a central axis $O_3$.

The support section 3*a* can be installed in an appropriate orientation with respect to the linear driving moving section 101*c*. In the present embodiment, as an example, the support section 3*a* is installed in an orientation in which a moving direction (see an arrow C of FIG. 1) of the linear driving moving section 101*c* is parallel to the central axis $O_3$.

The motor 4 is a member for supplying a rotary driving force to the shaft rotating member 3*c*. The motor 4 is electrically connected to a drive control unit (not shown), and rotated based on a control signal from the drive control unit.

The transmission mechanism 5 configured to transmit the rotary driving force of the motor 4 to the shaft rotating member 3*c* is installed between a motor output shaft 4*a* of the motor 4 and the surgical instrument driving unit 3.

The transmission mechanism 5 may employ an appropriate transmission mechanism such as a gear transmission mechanism, a belt transmission mechanism, or the like. In the present embodiment, as an example, as shown in FIG. 2, the transmission mechanism 5 employs a belt transmission mechanism including a drive pulley 5*a* installed at the motor output shaft 4*a*, a driven pulley 5*c* fixed to an outer circumferential section of a distal end side of the shaft rotating member 3*c*, and a transmission belt 5*b* fitted to and rotated by the drive pulley 5*a* and the driven pulley 5*c*.

In the present embodiment, a toothed belt is employed as the transmission belt 5*b* to accurately transmit a rotation angle without generating slippage.

In the present embodiment, in the surgical instrument driving unit 3, the motor 4 and the transmission mechanism 5 are covered by the support section 3*a*. However, the bearings 3*b* are exposed to the support section 3*a*. For this reason, sterilization treatment is not performed on the entire surgical instrument driving unit 3. In addition, a sterilization treatment may be appropriately performed on a member on which the sterilization treatment can be easily performed.

In the present embodiment, the shaft rotating member 3*c* is a member for changing a rotation position of the treatment tool unit 1 by rotating an orientation of the treatment tool unit 1 about the central axis $O_1$. For this reason, the shaft rotating member 3*c* may be configured to be rotated by at least half-turns in different directions.

The intermediate member 2 is a member configured to detachably connect the surgical instrument driving unit 3 and the treatment tool unit 1 and transmit a driving force from the surgical instrument driving unit 3 to the treatment tool unit 1. In addition, the intermediate member 2 is a member configured to connect the treatment tool unit 1, on which the sterilization treatment is performed, to the surgical instrument driving unit 3, on which the sterilization treatment is not performed, with no contact therebetween.

As shown in FIG. 1, the intermediate member 2 is a substantially tubular member about a central axis $O_2$, and a proximal end portion 2A and a tubular section 2B are disposed from a proximal end side to a distal end side thereof.

The proximal end portion 2A is a portion for detachably connecting the treatment tool unit 1 (to be described later). In the present embodiment, the proximal end portion 2A has an annular shape having a diameter larger than an outer diameter of the shaft rotating member 3*c*.

A conventional connection mechanism used for connection to the treatment tool unit 1 may be appropriately employed in a connection mechanism to the treatment tool unit 1. However, a connection means in which connection and disconnection is performed by the treatment tool unit 1 being advanced or retracted in a direction along the central axis $O_2$, may be more preferable.

As an example of such a preferable connection means, for example, a concavo-convex fitting structure or the like constituting a snap fit may be used. In this case, for example, a rod-shaped deformation section, which is elastically deformable, having a first engaging section formed at one end thereof, and a second engaging section engaged with the first engaging section in a concavo-convex shape may be installed at the proximal end portion 2A and the treatment tool unit 1, respectively. However, the second engaging section may be installed at the treatment tool unit 1, and the deformation section may be installed at the proximal end portion 2A.

The tubular section 2B is a tubular section passing through and inserting into the through-hole portion 3*d* of the shaft rotating member 3*c*, and includes an outer circumferential insertion section 2*c* having a shape fitted into the through-hole portion 3*d*.

The tubular section 2B has a length such that the tubular section 2B can pass through the drape rings 6A and 6B, the shaft rotating member 3*c*, and the drape rings 6C and 6D, in a state in which the shaft rotating member 3*c* is sandwiched between drape rings 6A and 6B, and drape rings 6C and 6D described later.

The drape rings 6A and 6B are fixed with the drape 7 (a blocking member) sandwiched therebetween. A hole portion 7C (see FIG. 3) having a size through which the tubular section 2B of the intermediate member 2 can pass is formed at the drape rings 6A and 6B and the drape 7.

Similarly, the drape rings 6C and 6D are fixed with the drape 7 sandwiched therebetween. A hole portion 7D (see FIG. 3) having a size through which the tubular section 2B of the intermediate member 2 can pass is formed at the drape rings 6C and 6D and the drape 7.

The drape 7 is a shielding member configured to block the surgical instrument unit support section 101, at which the surgical instrument driving unit 3 is installed, from the treatment tool unit 1, together with the surgical instrument driving unit 3. The drape 7 is formed of a sheet-shaped member having flexibility such as polyethylene, or the like, on which the sterilization treatment is performed.

In the present embodiment, the drape rings 6C and 6D, through which the tubular section 2B of the intermediate member 2 passes, are positioned to enable free rotation with respect to the tubular section 2B while interposed between the proximal end portion 2A of the intermediate member 2 and the shaft rotating member 3*c*. In addition, the tubular section 2B of the intermediate member 2 passes through the drape rings 6A and 6B. As a positional relation between the drape rings 6A and 6B and the drape rings 6C and 6D of the drape 7 is adjusted, it is possible to prevent the drape rings 6A and 6B from falling out from the tubular section 2B of the intermediate member 2. Meanwhile, a snap fit-shaped protrusion may be formed at the drape rings 6C and 6D or the tubular section 2B of the intermediate member 2 to prevent the drape rings 6A and 6B from falling out from the tubular section 2B of the intermediate member 2.

A key (a protrusion, not shown) engaged with a groove (not shown) extending in an axial direction of an inner circumference of the shaft rotating member 3*c* is disposed at the tubular section 2B of the intermediate member 2. For this reason, the intermediate member 2 and the shaft rotating member 3*c* are rotated together about the central axis $O_2$. In addition, the intermediate member 2 and the shaft rotating member 3*c* are configured to be slidably detachable in a direction of an arrow B. However, the intermediate member 2 is not easily deviated from the shaft rotating member 3*c* by friction and gravity between an outer circumferential surface of the tubular section 2B of the intermediate member 2 and an inner circumferential surface of the shaft rotating member 3*c* unless a person intentionally extracts the intermediate member 2 from the shaft rotating member 3*c*. However, positions of the intermediate member 2 and the shaft rotating member 3*c* may be fixed by a key (not shown) of the tubular section 2B of the intermediate member 2 and a snap fit disposed in a groove (not shown) of an inner circumference of the shaft rotating member 3*c*.

In addition, a surgical instrument unit insertion hole 2*d*, through which the treatment tool unit 1 can be inserted, is installed to pass through center portions of the proximal end portion 2A and the tubular section 2B in the axial direction.

The treatment tool unit 1 is configured to have a surgical instrument 1*a*, which is equipment or an instrument used in a surgical operation, formed at a distal end thereof, and configured to receive a driving force from the surgical instrument driving unit 3 via the intermediate member 2. The treatment tool unit 1 is detachably installed with respect to the intermediate member 2 in the axial direction.

As the surgical instrument 1*a*, equipment or an instrument that can be used through only movement by the surgical instrument unit support section 101 or rotation movement by the surgical instrument driving unit 3, with no application of a driving force from the outside, for example, a treatment tool such as a high frequency knife, or the like, may be used.

However, an instrument for receiving a driving force from the outside and performing an opening/closing motion or a curve motion, for example, a forceps, a stapler, an endoscope, a distal end portion of which is able to perform a curve motion, or the like may be employed.

Hereinafter, as an example, a case of the instrument used through only movement by the surgical instrument unit support section 101 or rotation movement by the surgical instrument driving unit 3 will be described.

The intermediate member 2 does not have a movable part or an electric circuit that has a possibility of deterioration due to the sterilization treatment. For this reason, the sterilization treatment is performed on the entire intermediate member 2.

The treatment tool unit 1 has substantially a shaft shape as a whole. The treatment tool unit 1 includes a connecting section 1A connected to the intermediate member 2, and a shaft-shaped section 1B having a proximal end portion connected to the connecting section 1A and a distal end portion provided with the surgical instrument 1*a*.

The connecting section 1A is detachably connected to the proximal end side of the proximal end portion 2A of the intermediate member 2.

The shaft-shaped section 1B has an outer diameter such that the shaft-shaped section 1B can be inserted into the surgical instrument unit insertion hole 2*d* of the intermediate member 2. The shaft-shaped section 1B has a length such that the shaft-shaped section 1B passes through the surgical instrument unit insertion hole 2*d*.

An engaging section (not shown) configured to position the treatment tool unit 1 with respect to the through-hole portion 3*d* in a circumferential direction of the treatment tool unit 1 is formed at least one of the connecting section 1A and the shaft-shaped section 1B.

As shown in FIG. 3, an inner edge of a drape hole 7*c* is sandwiched between the drape ring 6A (a shielding member, a frame member) joined with a surface 7*a* (one surface) of the drape 7 and the drape ring 6B (a shielding member, a frame member) joined with a surface 7*b* (the other surface), which is a rear surface of the surface 7*a*. Inner circumferential surfaces 6*a* and 6*b* having a shape into which the tubular section 2B can be inserted and fitted are formed in the drape rings 6A and 6B at coaxial positions, respectively.

In addition, an inner edge of a drape hole 7*d* is sandwiched between the drape ring 6C (a shielding member, a frame member) joined with the surface 7*a* and the drape ring 6D (a shielding member, a frame member) joined with the surface 7*b*. Inner circumferential surfaces 6*c* and 6*d* having a shape into which the tubular section 2B can be inserted and fitted are formed in the drape rings 6C and 6D at coaxial positions, respectively.

The drape rings 6A, 6B, 6C and 6D are formed of a material having a higher stiffness than that of the drape 7, for example, a metal, a synthetic resin, or the like. The drape rings 6A, 6B, 6C and 6D are joined with the drape 7 by, for example, adhesion, fusion, or the like.

According to the above-mentioned configuration, the hole portion 7C is formed by the inner circumferential surfaces 6*a* and 6*b* of the drape rings 6A and 6B. The hole portion 7C is a portion having an inner diameter smaller than a hole diameter of the drape hole 7*c* and into which the tubular section 2B can be inserted and fitted.

In addition, the hole portion 7D is formed by the inner circumferential surfaces 6*c* and 6*d* of the drape rings 6C and 6D. The hole portion 7D is a portion having an inner diameter smaller than a hole diameter of the drape hole 7*d* and into which the tubular section 2B can be inserted in fitted.

Hereinafter, the drape 7 to which the drape rings 6A, 6B, 6C and 6D are joined and in which the hole portions 7C and 7D are formed is referred to as a drape assembly 8 (a shielding member).

In the present embodiment, the sterilization treatment is performed on the drape assembly 8 as a whole.

In the drape assembly 8, surfaces other than the inner circumferential surfaces 6*a* and 6*c* of the drape rings 6A and 6C form a surface continued into the surface 7*a* of the drape 7.

In addition, surfaces other than the inner circumferential surfaces 6*b* and 6*d* of the drape rings 6B and 6D form a surface continued into the surface 7*b* of the drape 7.

The drape rings 6A, 6B, 6C and 6D cover the drape holes 7*c* and 7*d* that are formed in the drape 7 having flexibility and can be easily deformed, and configure frame members forming the hole portions 7C and 7D having a more stable shape.

As shown in FIG. 1, a distance between the hole portions 7C and 7D is set to a dimension such that, when the surgical instrument unit support section 101 is covered by the drape 7, about the hole portions 7C and 7D can be aligned with the central axis $O_3$ of the shaft rotating member 3*c*, with the surgical instrument driving unit 3 interposed therebetween.

An assembly method of the operation support device 100 having the above-mentioned configuration will be described.

Figure 4A:
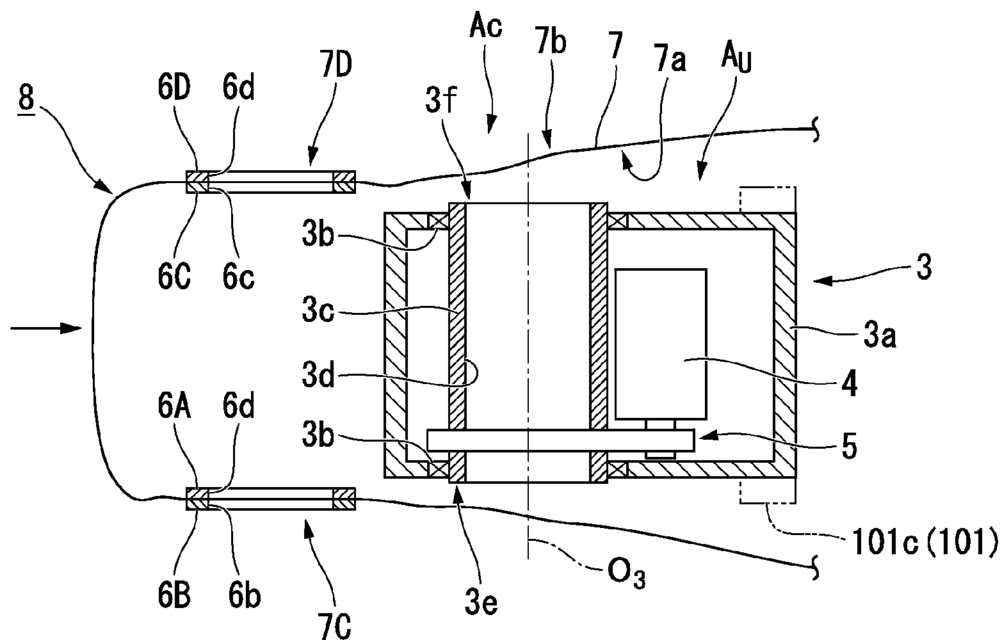
FIG. 4A is a schematic process view for describing a driving force supply unit installing process in an assembly method of the operation support device according to the first embodiment of the present invention.
Figure 4B:
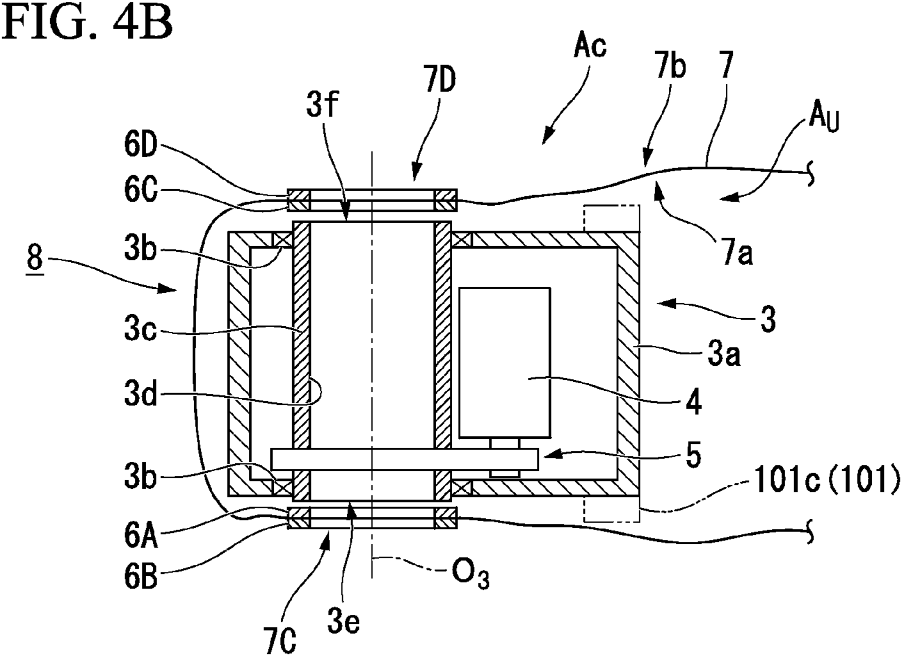
FIG. 4B is a schematic process view for describing a shielding member disposing process in the assembly method of the operation support device according to the first embodiment of the present invention.
Figure 5A:
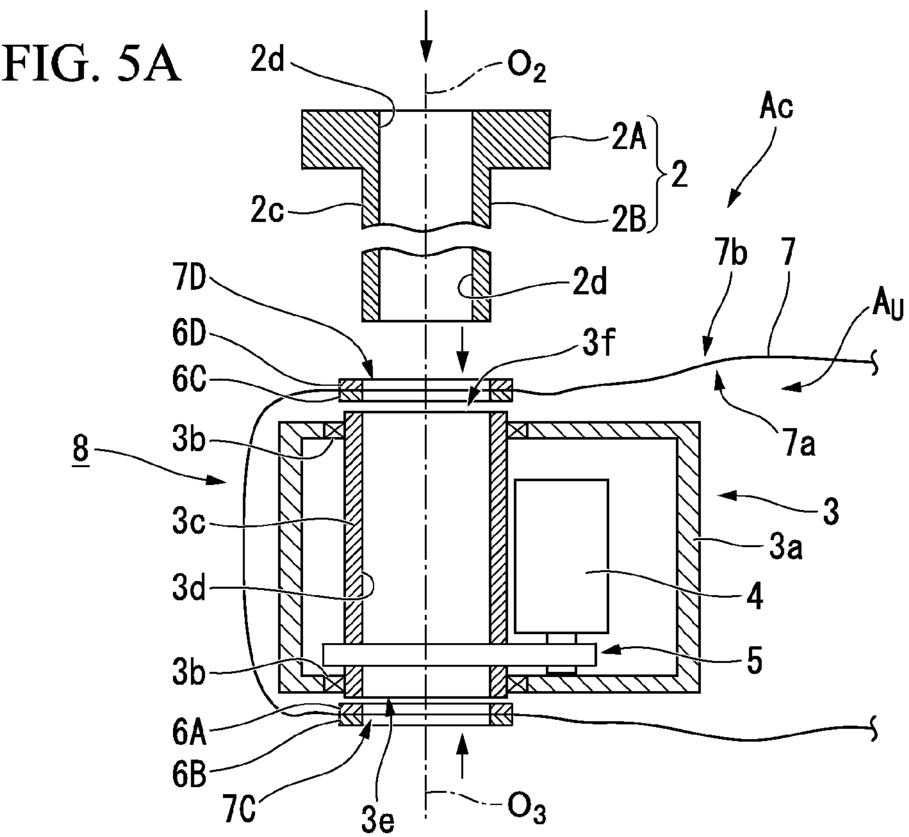
FIG. 5A a schematic process view for describing a first connecting process in the assembly method of the operation support device according to the first embodiment of the present invention.
Figure 5B:
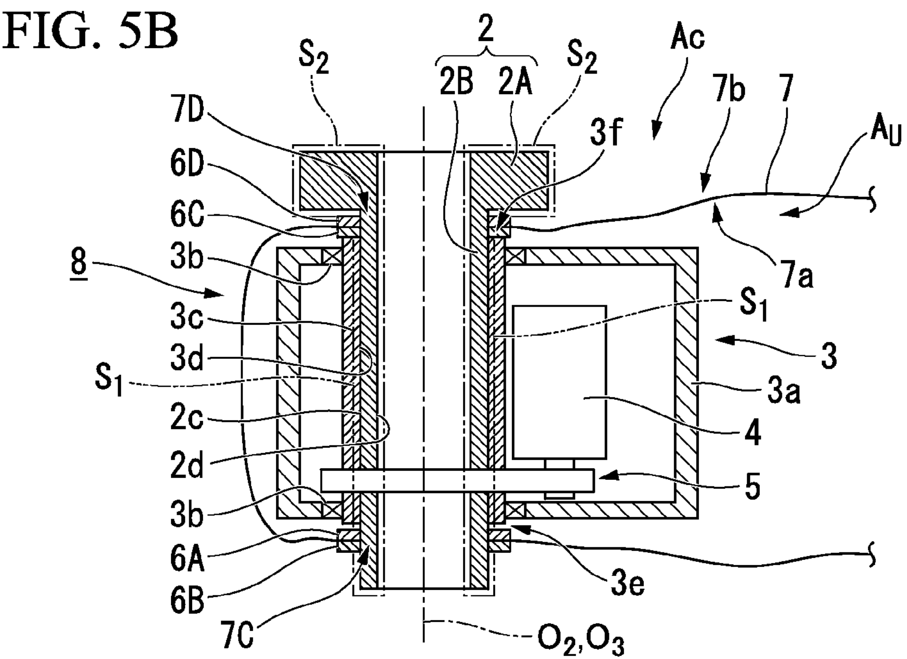
FIG. 5B is a schematic process view for describing the first connecting process in the assembly method of the operation support device according to the first embodiment of the present invention.
Figure 6:
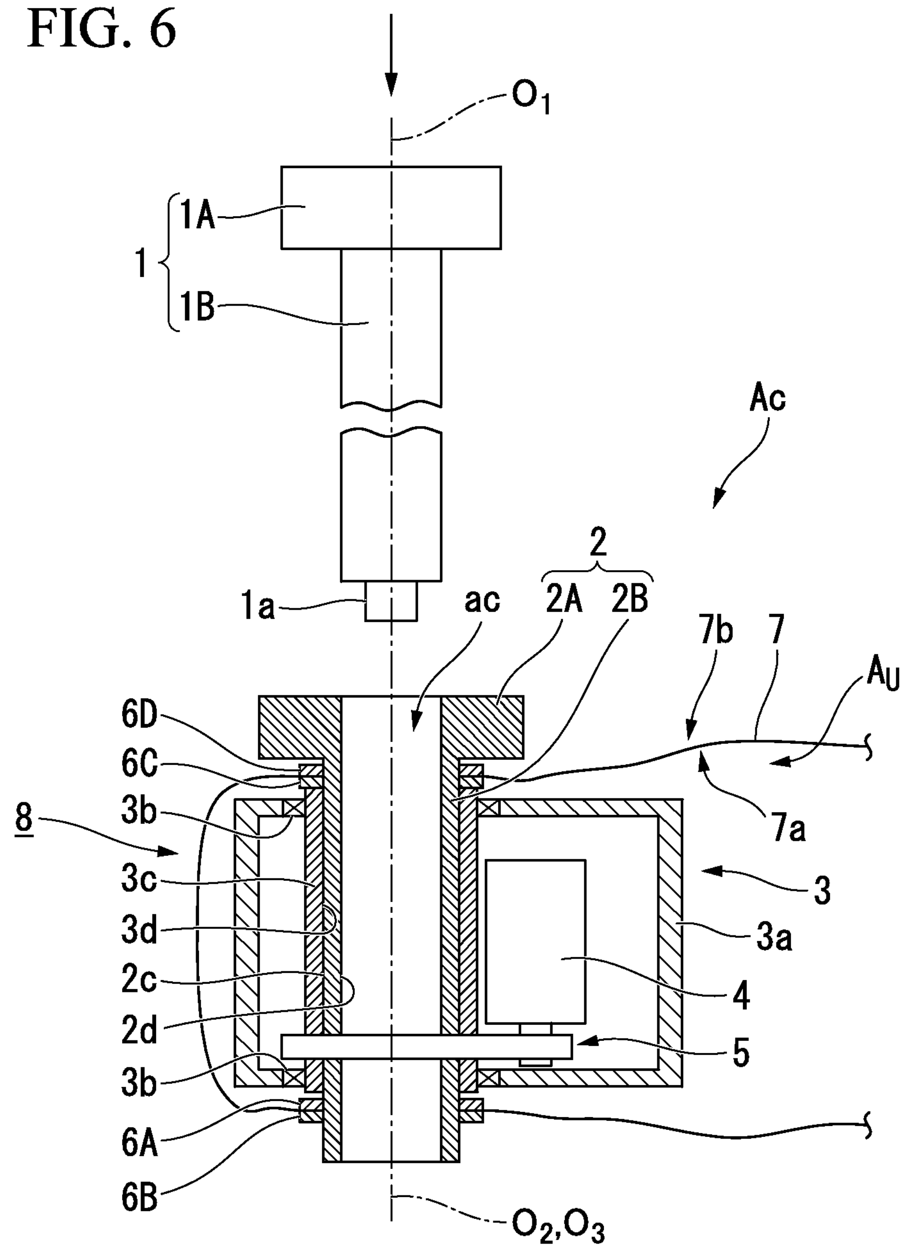
FIG. 6 is a schematic process view for describing a second connecting process in the assembly method of the operation support device according to the first embodiment of the present invention.

FIGS. 4A and 4B are schematic process views for describing a driving force supply unit installation process and a shielding member disposition process in the assembly method of the operation support device according to the first embodiment of the present invention. FIGS. 5A and 5B are schematic process views for describing a first connecting process in the assembly method of the operation support device according to the first embodiment of the present invention. FIG. 6 is a schematic process view for describing a second connecting process in the assembly method of the operation support device according to the first embodiment of the present invention.

In order to assemble the operation support device 100, as shown in FIG. 4A, the drape assembly 8 is previously formed. After that, a driving force supply unit installation process, a shielding member disposition process, a first connecting process, and a second connecting process are sequentially performed.

The driving force supply unit installation process is a process of positioning the surgical instrument driving unit 3, which is a driving force supply unit, using the surgical instrument unit support section 101.

Here, the surgical instrument driving unit 3 can be installed in an appropriate orientation in accordance with a stopped state of the surgical instrument unit support section 101. In the present embodiment, a stopped state of the surgical instrument unit support section 101 is previously adjusted, such that the surgical instrument driving unit 3 is set to be in an orientation in a substantially vertical direction (including a vertical direction) in a state in which the distal end portion 3*e* of the shaft rotating member 3*c* is directed downward.

As described above, the driving force supply unit installation process is finished.

Next, the shielding member disposition process is performed. This process is a process of disposing the surface 7*a*, which is one surface of the drape assembly 8 having the hole portions 7C and 7D, toward the surgical instrument unit support section 101 and the surgical instrument driving unit 3.

In the present embodiment, as shown in FIG. 4A, the surface 7*a* is directed to the surgical instrument driving unit 3 and the surgical instrument unit support section 101, and disposed at a position to cover the surgical instrument driving unit 3 and the surgical instrument unit support section 101.

Next, as shown in FIG. 4B, the drape assembly 8 is moved, and the drape rings 6A and 6C are moved such that the drape ring 6C approaches and faces the proximal end portion 3*f* of the shaft rotating member 3*c*, the drape ring 6A approaches and opposes the distal end portion 3*e* of the shaft rotating member 3*c*, and centers of the hole portions 7C and 7D are aligned with the central axis $O_3$ (including an aligned case), and the state is maintained.

Accordingly, the hole portion 7C, the through-hole portion 3*d* and the hole portion 7D are sequentially and serially disposed in a substantially vertical direction. Then, an outer circumferential section of the surgical instrument driving unit 3 is covered by the drape assembly 8 so as to form a C shape in a longitudinal cross-section.

As described above, the shielding member disposition process is finished.

Since the drape assembly 8 is disposed as described above, the surgical instrument driving unit 3, on which the sterilization treatment is not performed, is disposed in a region surrounded by the surface 7*a* of the drape assembly 8. Hereinafter, the region is referred to as an unclean area $A_U$ (a first space).

In addition, a region facing the surface 7*b* at a rear surface side of the drape assembly 8 is referred to as a clean area $A_C$ (a second space).

Upon finishing the process, the unclean area $A_U$ and the clean area $A_C$ are partitioned by the drape 7, and are communicated with each other by the hole portions 7C and 7D.

Next, the first connecting process is performed. This process is a process of attaching by inserting the intermediate member 2 into the hole portions 7C and 7D of the drape assembly 8 and attaching by inserting the intermediate member 2 into the surgical instrument driving unit 3 and connecting the intermediate member 2 to the surgical instrument driving unit 3. After the intermediate member 2 is connected to the surgical instrument driving unit 3, a first surface section of the intermediate member 2 is continued into the surface 7*a* of the drape assembly 8, a second surface section of the intermediate member 2 is continued into the surface 7*b* of the drape assembly 8, and a first surface section of the intermediate member 2 is set to face the surgical instrument driving unit 3.

In the present embodiment, as shown in FIG. 5A, in a state in which the drape assembly 8 is disposed, the tubular section 2B of the intermediate member 2 directed downward is disposed on the hole portion 7D, and the intermediate member 2 is inserted into the hole portion 7D, the through-hole portion 3*d* of the shaft rotating member 3*c* and the hole portion 7C from the distal end side.

Accordingly, the drape rings 6C and 6D are fitted to the tubular section 2B in a state in which the drape rings 6C and 6D are sandwiched between the proximal end portion 2A and the proximal end portion 3*f* of the shaft rotating member 3*c* at the proximal end side of the tubular section 2B.

In addition, the drape rings 6A and 6B are fitted to the tubular section 2B in a state in which the drape rings 6A and 6B are opposite to the distal end portion 3*e* of the shaft rotating member 3*c* at the distal end side of the tubular section 2B.

As described above, the tubular section 2B of the intermediate member 2 and the through-hole portion 3*d* of the shaft rotating member 3*c* are engaged with each other to be rotated together by a key and a groove (not shown). For this reason, the shaft rotating member 3*c* is not dropped downward in the vertical direction by the proximal end portion 2A of the intermediate member 2 in the axial direction, and is not extracted upward due to gravity and a frictional force unless a person intentionally pulls the member.

As described above, the first connecting process is finished.

After the first connecting process is finished, as shown in FIG. 5B, in the intermediate member 2, a surface of the insertion outer circumferential section 2*c* sandwiched between the drape rings 6C and 6A constitutes a first surface section $S_1$ continued into the surface 7*a* of the drape 7. In addition, the first surface section $S_1$ faces the shaft rotating member 3*c* of the surgical instrument driving unit 3 in the through-hole portion 3*d*.

In the intermediate member 2, surfaces of the proximal end portion 2A other than the drape ring 6D and the insertion outer circumferential section 2*c* of the proximal end side, an inner circumferential surface of the surgical instrument unit insertion hole 2*d*, and a surface of the shaft rotating member 3*c* of the distal end side other than the drape ring 6B of the tubular section 2B constitute a second surface section $S_2$ continued into the surface 7*b* of the drape 7.

As described above, in the present embodiment, the drape assembly 8 attached by insertion to the intermediate member 2 divides a surface region of intermediate member 2 into the first surface section $S_1$ and the second surface section $S_2$, which are two different regions.

Then, the surface 7*a* and the first surface section $S_1$ constitute a surface configured to cover the unclean area $A_U$. The surface 7*b* and the second surface section $S_2$ constitute a surface configured to cover the clean area $A_C$.

For this reason, after the first connecting process is finished, as the intermediate member 2 is mounted on the hole portions 7C and 7D, the unclean area $A_U$ and the clean area $A_C$ in communication with each other via the hole portions 7C and 7D are partitioned into two regions not in communication with each other, except for the outermost circumferential surface of the drape 7. Accordingly, as the drape 7 is formed to have substantially a large size to correspond to the surgical instrument driving unit 3 and the surgical instrument unit support section 101, the surgical instrument driving unit 3 and the surgical instrument unit support section 101 can be isolated from the unclean area $A_U$ to be shielded from the clean area $A_C$.

Accordingly, this process is a process of engaging the hole portions 7C and 7D of the drape assembly 8 and the intermediate member 2 to form an assembly constituted by the drape assembly 8 and the intermediate member 2, positioning the surgical instrument driving unit 3 and surgical instrument support section 101 in the first space using the assembly as a boundary, and detachably connecting the intermediate member 2 and surgical instrument support section 101 in a side of the first space.

Next, the second connecting process is performed. This process is a process of connecting the clean treatment tool unit 1 to the intermediate member 2 in the second surface section $S_2$ of the intermediate member 2.

After the first connecting process is finished, the surgical instrument unit insertion hole 2*d* of the intermediate member 2 is passed through in the state which does not communicate with the unclean area $A_U$ in the unclean area $A_U$ protruding in the clean area $A_C$ and forms a clean area $a_C$ (see FIG. 6) having a wide cylindrical shape constituting a part of the clean area $A_C$.

In this process, first, as shown in FIG. 6, the treatment tool unit 1 is held over the intermediate member 2 such that the surgical instrument 1*a* is directed downward. Here, the treatment tool unit 1, on which the sterilization treatment has been performed, is positioned in the clean area $A_C$ over the surgical instrument driving unit 3.

Next, the shaft-shaped section 1B of the treatment tool unit 1 is inserted into the surgical instrument unit insertion hole 2*d* of the proximal end side (an upper side of FIG. 6) of the intermediate member 2 from a side of the surgical instrument 1*a* to pass the surgical instrument 1*a* to the distal end side. Here, the surgical instrument 1*a* and the shaft-shaped section 1B are moved to the clean area $A_C$ under a side of the surgical instrument driving unit 3 from the clean area $A_C$ over the surgical instrument driving unit 3 via the clean area $a_C$.

Then, as shown in FIG. 1, the connecting section 1A is connected to the proximal end portion 2A of the intermediate member 2. Here, the shaft-shaped section 1B is in contact with the surgical instrument unit insertion hole 2*d*, and slides and moves. However, since the sterilization treatment is performed on the surgical instrument unit insertion hole 2*d*, the treatment tool unit 1 is not contaminated by the intermediate member 2.

As described above, the second connecting process is finished.

Accordingly, this process is a process of detachably holding the intermediate member 2 and the treatment tool unit 11 in a side of a second space opposite to the first space using the assembly constituted by the drape assembly 8 and the intermediate member 2 as a boundary.

As described above, the operation support device 100 can be assembled.

In addition, in the operation support device 100, as the above-mentioned second connecting process is reversely performed, connection to the treatment tool unit 1 is released, the treatment tool unit 1 is extracted from an upper side (the proximal end side of the shaft rotating member 3*c* and the intermediate member 2) of the surgical instrument driving unit 3 and the intermediate member 2, and the treatment tool unit 1 can be removed from the surgical instrument driving unit 3 and the intermediate member 2.

As described above, in the present embodiment, the treatment tool unit 1 is connected from the upper side of the intermediate member 2. Since the treatment tool unit 1 is connected to the proximal end side by the proximal end portion 2A having a diameter larger than the surgical instrument unit insertion hole 2*d*, even when connection to the intermediate member 2 is released, the treatment tool unit 1 does not fall downward. For this reason, even in a state in which the surgical instrument driving unit 3 is positioned over the patient P, the treatment tool unit 1 can be easily attached and detached effectively using a space over the surgical instrument driving unit 3.

Next, a motion of the operation support device 100 will be described.

In the operation support device 100, the position and orientation of the linear driving moving section 101*c* are varied by the multi-joint arm 101*b*, and the surgical instrument driving unit 3 can be held in an appropriate orientation with respect to the patient P.

In addition, in this orientation, as the linear driving moving section 101*c* is driven, the surgical instrument driving unit 3 can be performed linear driving movement. In the present embodiment, the surgical instrument driving unit 3 can be moved in a direction parallel to the central axis $O_3$. For this reason, for example, as the surgical instrument 1*a* is positioned in a direction toward the patient P by the surgical instrument unit support section 101 to drive the linear driving moving section 101*c*, the surgical instrument 1*a* supported by the surgical instrument driving unit 3 can advance and retract with respect to the patient P.

Further, as the surgical instrument unit support section 101 is driven, the surgical instrument 1*a* can perform movement having multiple degrees of freedom on the patient P and the body cavity of the patient P. Accordingly, for example, when the surgical instrument 1*a* is a high frequency knife, as the surgical instrument 1*a* is relatively moved with respect to the patient P, the biological tissue can be excised.

In addition, the surgical instrument driving unit 3 transmits a rotary driving force of the motor 4 to the shaft rotating member 3*c* by the transmission mechanism 5. For this reason, the shaft rotating member 3*c*, the intermediate member 2 connected to the shaft rotating member 3*c*, and the treatment tool unit 1 connected to the intermediate member 2 can be rotatably driven about the central axis $O_3$ and the central axes $O_2$ and $O_1$ coaxial with the central axis $O_3$.

For this reason, an angle about the central axis $O_1$ of the surgical instrument 1*a* is appropriately varied, and a direction of the surgical instrument 1*a* can be varied.

In addition, since the intermediate member 2 and the drape rings 6D, 6C, 6B and 6A are configured to be freely rotated about the axis $O_1$ upon this rotation, there is no influence on the drape assembly 8. Further, even when the drape rings 6D, 6C, 6B and 6A are rotated together with the intermediate member 2 due to the friction, the drape 7 formed of a soft material is accordingly deformed with almost no resistance against the rotation. For this reason, there is no obstacle to rotation and the task of the surgical instrument 1*a*.

According to the above-mentioned operation support device 100, the surgical instrument driving unit 3 and the surgical instrument unit support section 101, on which the sterilization treatment is not performed, are blocked by the drape assembly 8, and the surgical instrument driving unit 3 and the surgical instrument unit support section 101 can be isolated in the unclean area $A_U$ not in communication with the clean area $A_C$. For this reason, even when the sterilization treatment is not performed, the operation support device 100 can be used in an operating room, or the like.

For this reason, as components of the surgical instrument driving unit 3 and the surgical instrument unit support section 101, movable parts, electric parts, or the like, on which the sterilization treatment cannot be easily performed or the sterilization treatment may be likely to cause deterioration, can be employed. For this reason, costs of the surgical instrument driving unit 3 and the surgical instrument unit support section 101 can be reduced, and lifespan thereof can be increased.

For example, the bearing 3*b* may not be an expensive bearing having high durability with respect to the sterilization treatment. In addition, there is no deterioration on the bearing 3*b* due to the sterilization treatment. For this reason, there is no need to frequently exchange the bearing 3*b* with a new one, and the surgical instrument driving unit 3 can be configured at a low cost.

Further, in general, since a soft drape 7, which is disposal member in general, and an intermediate member for power transmission are separated from each other and the sterilization treatment can be repeatedly performed on the intermediate member, cost of the disposable parts is reduced.

In addition, as an example, in the surgical instrument driving unit 3, a configuration that the motor 4 and the transmission mechanism 5 are covered by the support section 3*a* having a box shape has been described. However, since there is no need to perform the sterilization treatment on the entire surgical instrument driving unit 3, there is no need to form the support section 3*a* in a box shape in order to protect the motor 4 or the transmission mechanism 5 from the sterilization treatment. For this reason, as the support section 3*a*, a plate-shaped member or a block-shaped member, by which the motor 4 or the transmission mechanism 5 is not covered, may be used.

In addition, according to the assembly method of the operation support device 100 of the present embodiment, in a state in which the treatment tool unit 1 is disposed in the clean area $A_C$, the treatment tool unit 1 can be attached to and detached from the intermediate member 2, on which the sterilization treatment has been performed, with no contact with the surgical instrument driving unit 3. For this reason, exchange of the treatment tool unit 1 in the operating room can be rapidly and easily performed.

For example, when a plurality of operations are performed in the operating room, there is a need to exchange the treatment tool unit 1 in accordance with a kind of operation or a patient P. However, since the surgical instrument driving unit 3 and the surgical instrument unit support section 101 are isolated in the clean area $A_C$ and are not in contact with the treatment tool unit 1, the surgical instrument driving unit 3 and the surgical instrument unit support section 101 can be continuously used with no need to perform exchange or movement.

First Modified Example

Next, an operation support device according to a modified example (a first modified example) of the present embodiment will be described.

Figure 7:
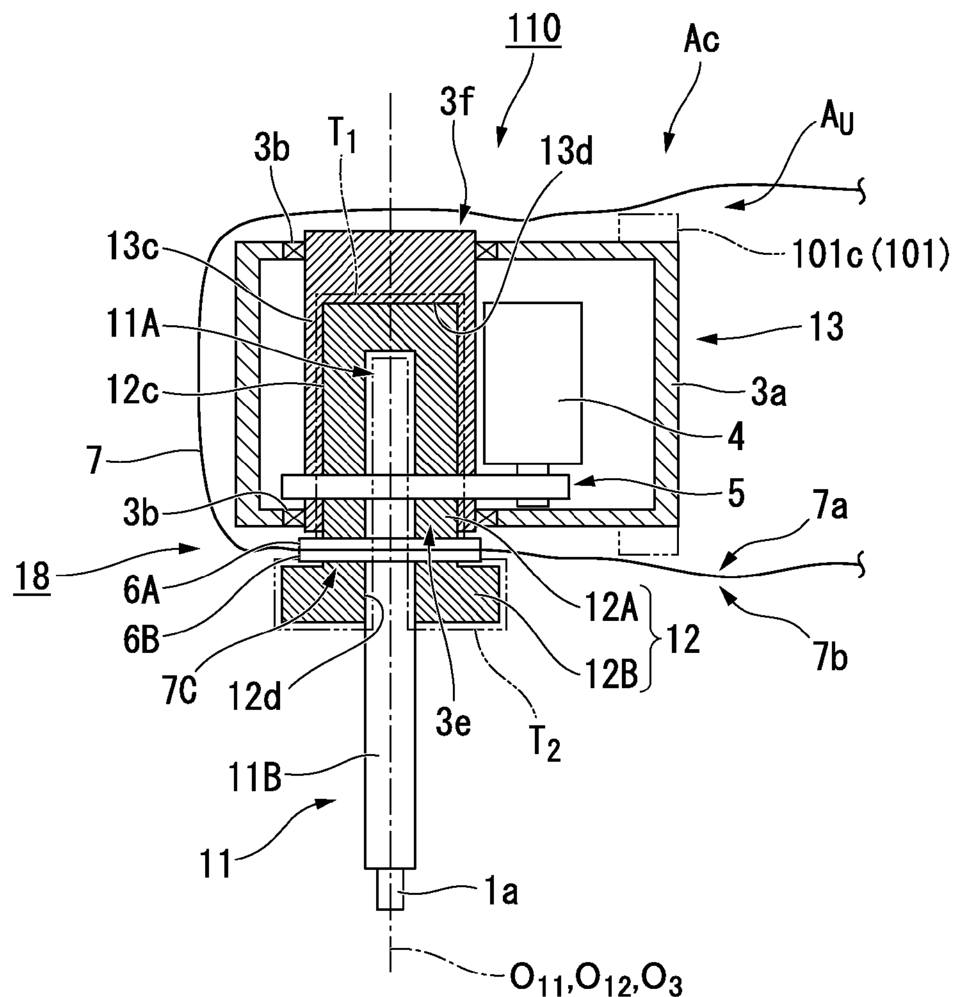
FIG. 7 is a schematic partial cross-sectional view showing a configuration of main parts of an operation support device of a present modified example (a first modified example) of the first embodiment of the present invention.

FIG. 7 is a schematic partial cross-sectional view showing a configuration of main parts of the operation support device according to the modified example (the first modified example) of the first embodiment of the present invention.

As shown in FIG. 7, an operation support device 110 according to the present modified example includes a drape assembly 18 (a shielding member), a surgical instrument driving unit 13 (a driving force supply unit), an intermediate member 12, and a treatment tool unit 11 (a surgical instrument unit), instead of the drape assembly 8, the surgical instrument driving unit 3, the intermediate member 2, and the treatment tool unit 1 included in the operation support device 100 according to the first embodiment, respectively.

The surgical instrument driving unit 13 includes a shaft rotating member 13*c*, instead of the shaft rotating member 3*c* included in the surgical instrument driving unit 3 according to the first embodiment.

In addition, the sterilization treatment is performed on the drape assembly 18, the intermediate member 12, and the treatment tool unit 11. The sterilization treatment is not performed on the surgical instrument driving unit 13.

Hereinafter, the first modified example will be described focusing on differences from the first embodiment.

The drape assembly 18 does not include the drape rings 6C and 6D, and the hole portion 7D of the drape assembly 8 according to the first embodiment. For this reason, as hole portions, the drape assembly 18 has only the hole portion 7C.

In the shaft rotating member 13*c*, an opening of the proximal end portion 3*f* of the shaft rotating member 3*c* according to the first embodiment is closed. The shaft rotating member 13*c* is a cylindrical member having a bottom opened at the distal end portion 3*e* only. For this reason, instead of the through-hole portion 3*d*, an insertion hole portion 13*d* coaxial with the central axis $O_3$ is formed at a center portion of the distal end portion 3*e*.

The intermediate member 12 is a member configured to detachably connect the surgical instrument driving unit 13 and the treatment tool unit 11 and to transmit a driving force from the surgical instrument driving unit 13 to the treatment tool unit 11. In addition, the intermediate member 12 connects the treatment tool unit 11, on which the sterilization treatment has been performed, to the surgical instrument driving unit 3, on which the sterilization treatment is not performed, with no contact.

As shown in FIG. 7, the intermediate member 12 is a substantially tubular member about a central axis $O_{12}$. In the intermediate member 12, an insertion connecting section 12A and a distal end portion 12B are disposed from the proximal end side toward the distal end side.

The insertion connecting section 12A is a section detachably connecting the treatment tool unit 11 described later. In the present modified example, the insertion connecting section 12A is a section having a cylindrical appearance inserted into the insertion hole portion 13*d* of the shaft rotating member 13*c* from the distal end side (a lower side of FIG. 7). The insertion connecting section 12A includes an insertion outer circumferential section 12*c* formed at an outer circumferential section thereof and having a shape detachably fitted to the insertion hole portion 13*d*.

The insertion outer circumferential insertion section 12*c* and the insertion hole portion 13*d* are configured to be detachably attached to each other. The insertion outer circumferential insertion section 12*c* may be constituted by a connecting structure (not shown) configured to fix relative positions in the axial direction and the circumferential direction, for example, a snap fit, a magnet, or the like.

The distal end portion 12B is an annular section faces the distal end portion 3*e* of the shaft rotating member 3*c* in the distal end side of the insertion connecting section 12A connected to the shaft rotating member 13*c*.

A surgical instrument unit insertion hole 12*d* is formed in the center portion of the distal end portion 12B such that the proximal end portion of the treatment tool unit 11 is inserted and held in the center portion. In the present modified example, the surgical instrument unit insertion hole 12*d* is constituted by a hole portion coaxial with the central axis $O_{12}$ of the insertion outer circumferential section 12*c* from the distal end side of the distal end portion 12B toward an inner side of the insertion connecting section 12A.

For this reason, the intermediate member 12 has a cylindrical shape having a bottom, in which the surgical instrument unit insertion hole 12*d* is opened at the distal end side and closed at the proximal end side.

A drape ring fixing section (not shown) configured to fix the drape rings 6A and 6B between the distal end portion 3*e* of the shaft rotating member 13*c* and the drape ring fixing section upon connection to the shaft rotating member 13*c* is formed at the proximal end side of the distal end portion 12B. As the drape ring fixing section, the same configuration as in the first embodiment may be employed.

In addition, a connecting section (not shown) configured to detachably connect and fix positions in the axial direction and the circumferential direction of the treatment tool unit 11 inserted into the surgical instrument unit insertion hole 12*d* is formed at the distal end side of the distal end portion 12B. As the connecting section, for example, a collet chuck, or the like may be employed.

The treatment tool unit 11 is configured to have the surgical instrument 1*a* at the distal end thereof and configured to receive a driving force transmitted from the surgical instrument driving unit 13 via the intermediate member 12. The treatment tool unit 11 is detachably installed with respect to the intermediate member 12 in the axial direction.

The treatment tool unit 11 has substantially a shaft shape as a whole. A proximal end side insertion section 11A inserted into the surgical instrument unit insertion hole 12*d* of the intermediate member 12 is formed at the proximal end side of the treatment tool unit 11, and a shaft-shaped section 11B is installed between the proximal end side insertion section 11A and the surgical instrument 1*a*.

In the shaft-shaped section 11B, a connecting section (not shown) configured to fix positions with respect to the intermediate member 12 in the axial direction and the circumferential direction is installed at a position adjacent to the distal end portion 12B of the intermediate member 12 upon connection to the intermediate member 12.

The operation support device 110 having the above-mentioned configuration can be assembled in substantially the same manner as in the first embodiment.

That is, in a state in which the drape assembly 18 is previously formed, a driving force supply unit installation process, a shielding member disposition process, a first connecting process, and a second connecting process are sequentially performed. Hereinafter, the present modified example will be described focusing on differences from the first embodiment.

The driving force supply unit installation process according to the present modified example is a process of installing the surgical instrument driving unit 13, instead of the surgical instrument driving unit 3, at the surgical instrument unit support section 101, which is the same process as in the first embodiment.

The shielding member disposition process according to the present modified example is distinguished from the shielding member disposition process according to the first embodiment in that, since the hole portion 7D is not formed in the drape assembly 18, when the drape assembly 18 is moved toward the surgical instrument driving unit 13, the drape ring 6A is disposed adjacent to the distal end portion 3*e* of the shaft rotating member 13*c*, and a center of the hole portion 7C is substantially aligned with the central axis $O_3$.

The first connecting process according to the present modified example is a process of inserting the intermediate member 12 into the hole portion 7C of the drape assembly 18, attaching the intermediate member 12 to the drape assembly 18, and connecting the intermediate member 12 to the surgical instrument driving unit 13. After the intermediate member 12 is connected to the surgical instrument driving unit 13, the intermediate member 12 is set such that the first surface section of the intermediate member 12 is continued into the surface 7*a* of the drape assembly 18, the second surface section of the intermediate member 12 is continued into the surface 7*b* of the drape assembly 18, and the first surface section of the intermediate member 12 faces the surgical instrument driving unit 13.

In the present modified example, in a state in which the drape assembly 18 is disposed during the previous process, the insertion connecting section 12A of the intermediate member 12 directed upward is disposed under the hole portion 7C, and the intermediate member 12 is inserted into the hole portion 7C and the insertion hole portion 13*d* of the shaft rotating member 13*c* from the proximal end side.

Accordingly, as shown in FIG. 7, the drape rings 6A and 6B are fitted to the distal end side of the insertion connecting section 12A while facing the distal end portion 3*e* of the shaft rotating member 13*c* in the proximal end side of the distal end portion 12B.

In this state, the intermediate member 12 and the surgical instrument driving unit 13 are connected to each other, and the intermediate member 12 and the drape rings 6A and 6B are connected to each other.

As described above, the first connecting process according to the present modified example is finished.

After the above-mentioned first connecting process is finished, as shown in FIG. 7, in the intermediate member 12, a surface of the insertion outer circumferential section 12*c* of the proximal end side rather than the drape ring 6A constitutes a first surface section $T_1$ continued into the surface 7*a* of the drape 7. In addition, the first surface section $T_1$ faces the shaft rotating member 13*c* of the surgical instrument driving unit 13 in the insertion hole portion 13*d*.

In the intermediate member 12, the distal end portion 12B of the distal end side other than the drape ring 6A and an inner surface of the surgical instrument unit insertion hole 12*d* constitute a second surface section $T_2$ continued into the surface 7*b* of the drape 7.

In the present modified example, the drape assembly 18 attached by insertion to the intermediate member 12 divides a surface region of the intermediate member 12 into the first surface section $T_1$ and the second surface section $T_2$, which are two different regions.

Then, the surface 7*a* and the first surface section $T_1$ constitute a surface covering the unclean area $A_U$. The surface 7*b* and the second surface section $T_2$ constitute a surface covering the clean area $A_C$.

For this reason, similar to the first embodiment, the drape assembly 18 isolates the surgical instrument driving unit 13 and the surgical instrument unit support section 101 in the unclean area $A_U$, and shields the surgical instrument driving unit 13 and the surgical instrument unit support section 101 from the clean area $A_C$.

The second connecting process according to the present modified example is a process of connecting the treatment tool unit 11 to the intermediate member 12 in the second surface section $T_2$ of the intermediate member 12.

After the first connecting process is finished, the surgical instrument unit insertion hole 12*d* of the intermediate member 12 protrudes in a state not in communication with the unclean area $A_U$ to constitute a part of the clean area $A_U$ in the unclean area $A_U$ protruding into the clean area $A_C$.

In this process, the treatment tool unit 11 is held under the intermediate member 12 such that the surgical instrument 1*a* is directed downward. Here, the treatment tool unit 11 in which the sterilization treatment is performed is disposed in the clean area $A_C$ under the surgical instrument driving unit 13.

Next, the proximal end side insertion section 11A of the treatment tool unit 11 is inserted into the surgical instrument unit insertion hole 12*d* of the intermediate member 12. Then, in the distal end portion 12B, the proximal end side insertion section 11A of the treatment tool unit 11 is connected to the treatment tool unit 11 (see FIG. 7).

Here, the proximal end side insertion section 11A is in contact with the surgical instrument unit insertion hole 12*d*, and slides and moves. However, since the sterilization treatment is performed on the surgical instrument unit insertion hole 12*d*, the treatment tool unit 11 is not contaminated by the intermediate member 12.

As described above, the second connecting process is finished.

In this way, the operation support device 110 can be assembled.

According to the operation support device 110 as described above, similar to the first embodiment, the surgical instrument driving unit 13 and the surgical instrument unit support section 101, on which the sterilization treatment is not performed, are blocked by the drape assembly 18, and the surgical instrument driving unit 13 and the surgical instrument unit support section 101 can be isolated in the unclean area $A_U$ not in contact with the clean area $A_C$. For this reason, even when the sterilization treatment is not performed, the operation support device 110 can be used in an operating room, or the like.

In addition, costs of the surgical instrument driving unit 13 and the surgical instrument unit support section 101 can be reduced, and lifespan thereof can be increased.

Further, according to the assembly method of the operation support device 110 according to the present modified example, in a state in which the treatment tool unit 11 is disposed in the clean area $A_C$, the treatment tool unit 11 can be detachably attached to the intermediate member 12, on which the sterilization treatment has been performed, with no contact with the surgical instrument driving unit 13. For this reason, exchange of the treatment tool unit 11 in the operating room can be rapidly and easily performed.

Second Embodiment

Next, the operation support device according to a second embodiment of the present invention will be described. The present embodiment is an embodiment of a case in which a force for driving a surgical instrument distal end of a treatment tool unit is transmitted from a surgical instrument driving unit via an intermediate member.

Figure 8:
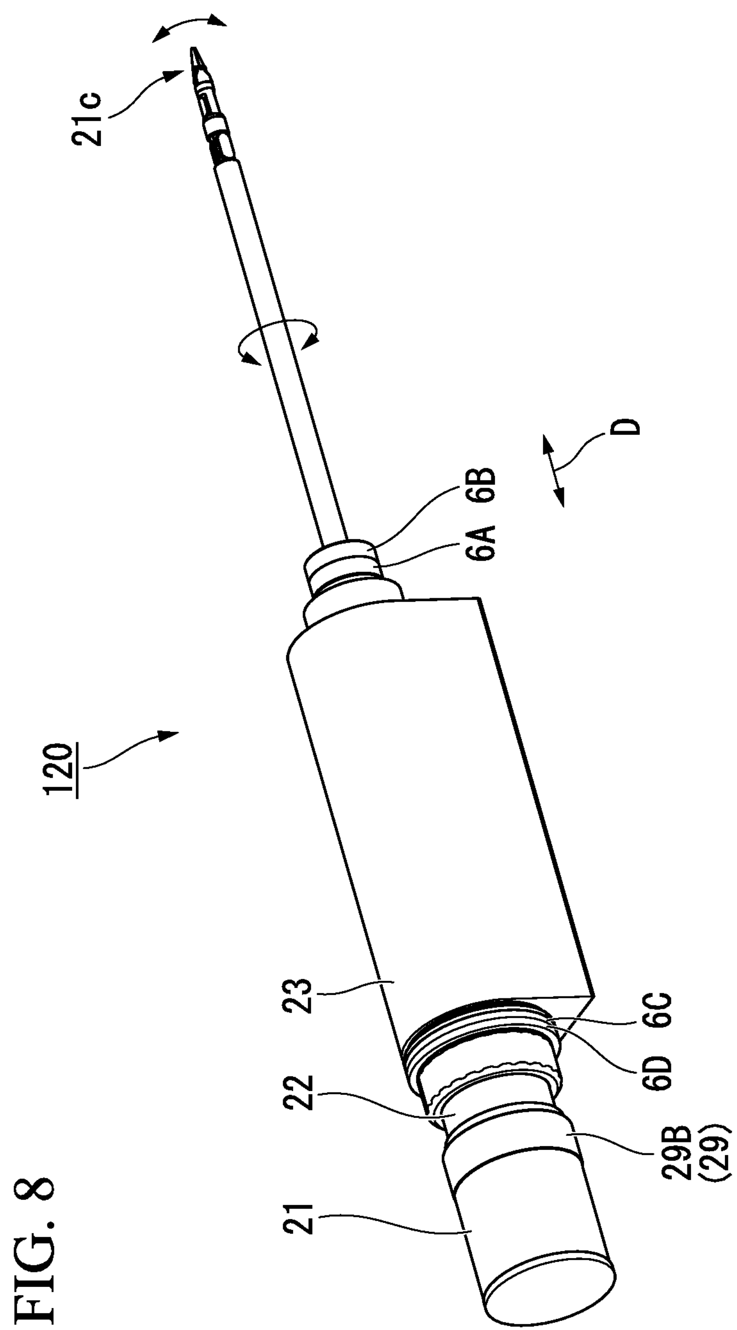
FIG. 8 is a schematic perspective view showing an appearance of main parts of an operation support device according to a second embodiment of the present invention.
Figure 9:
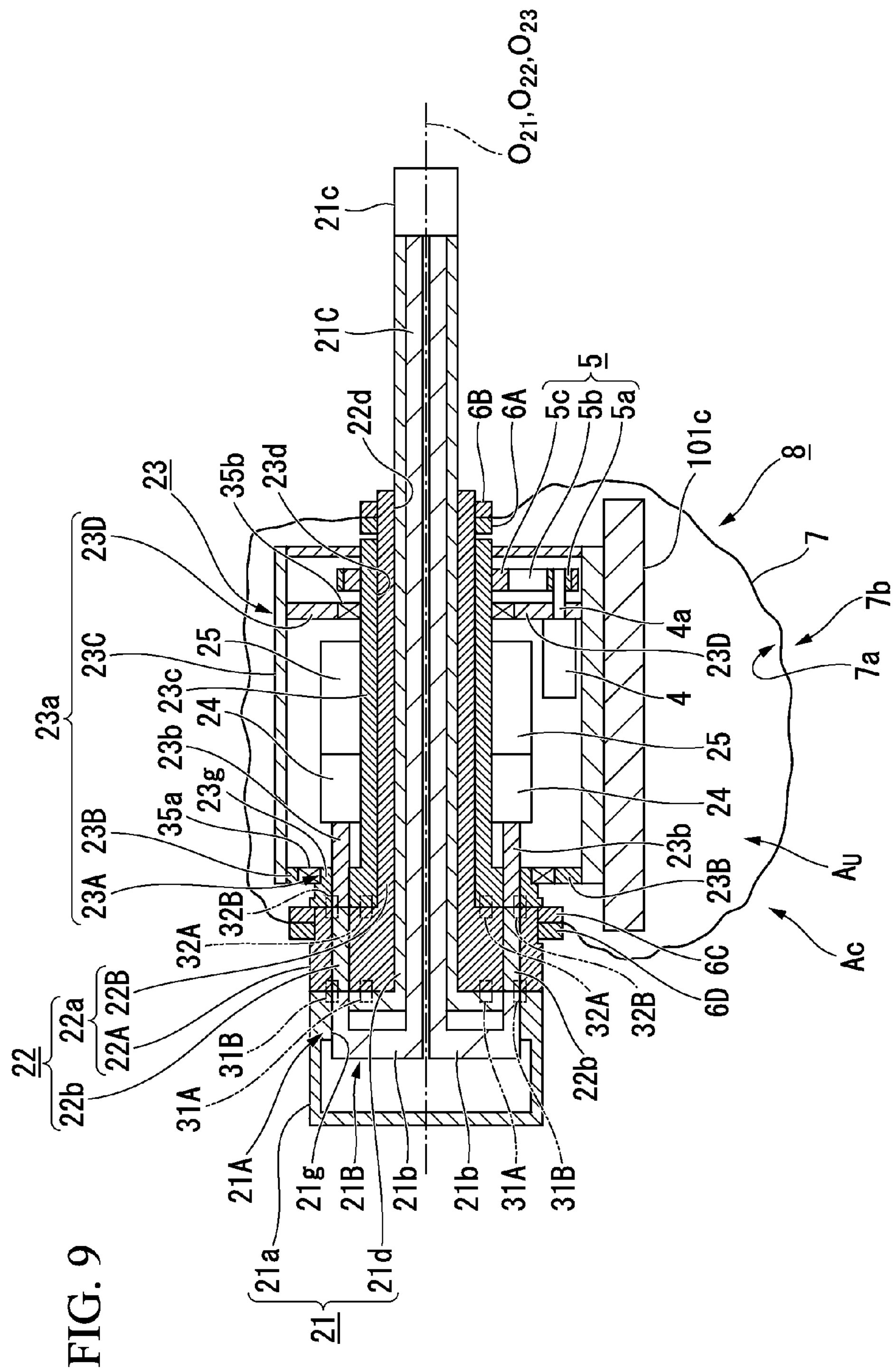
FIG. 9 is a schematic cross-sectional view of the main parts of the operation support device according to the second embodiment of the present invention upon connection in an axial direction.
Figure 10:
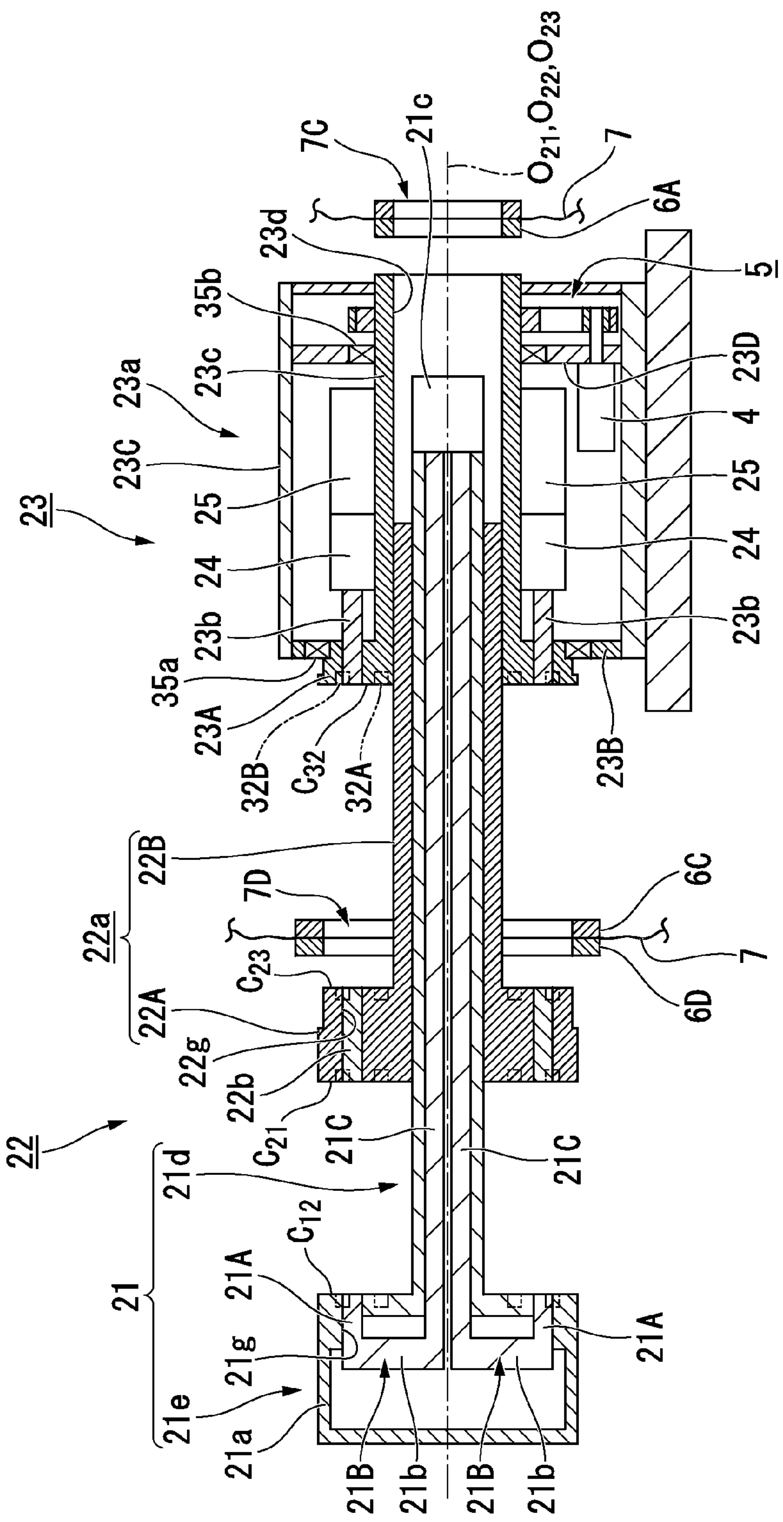
FIG. 10 is a schematic cross-sectional view of the main parts of the operation support device according to the second embodiment of the present invention upon deconcatenation in the axial direction.
Figure 11:
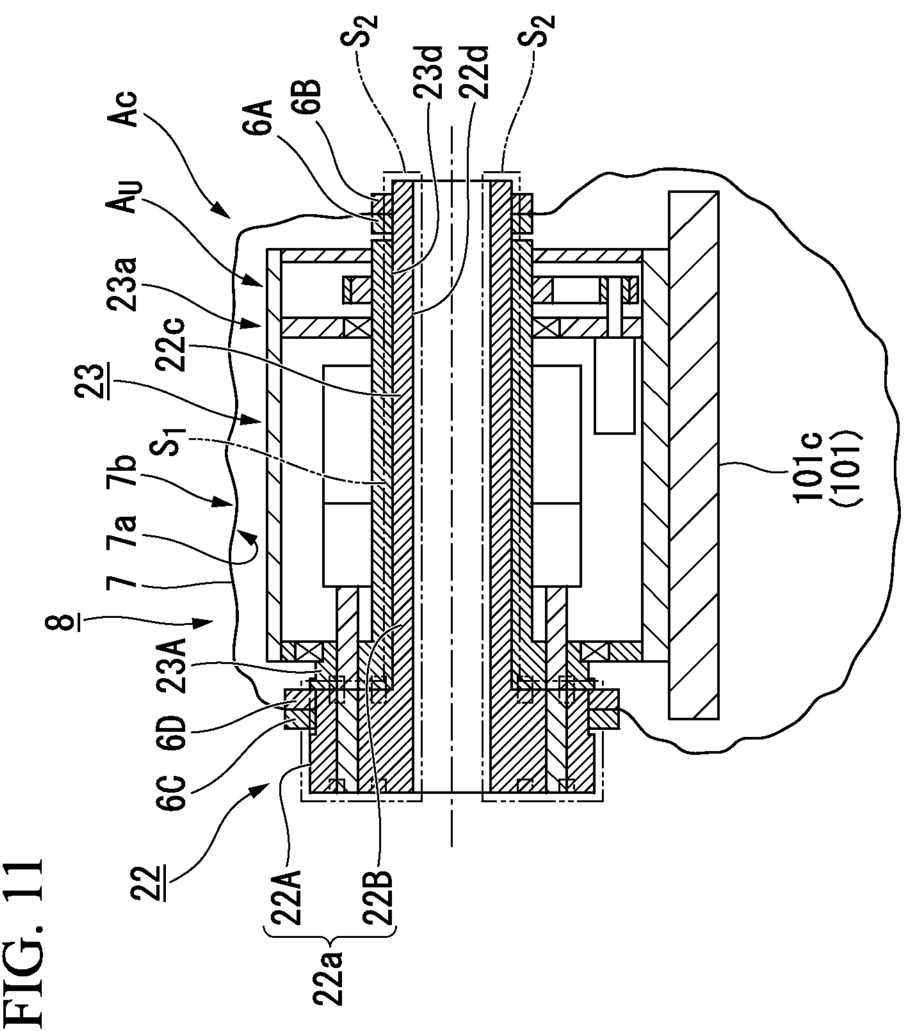
FIG. 11 is a schematic cross-sectional view of a surgical instrument unit drive unit and an intermediate member of the operation support device according to the second embodiment of the present invention upon connection in the axial direction.
Figure 12:
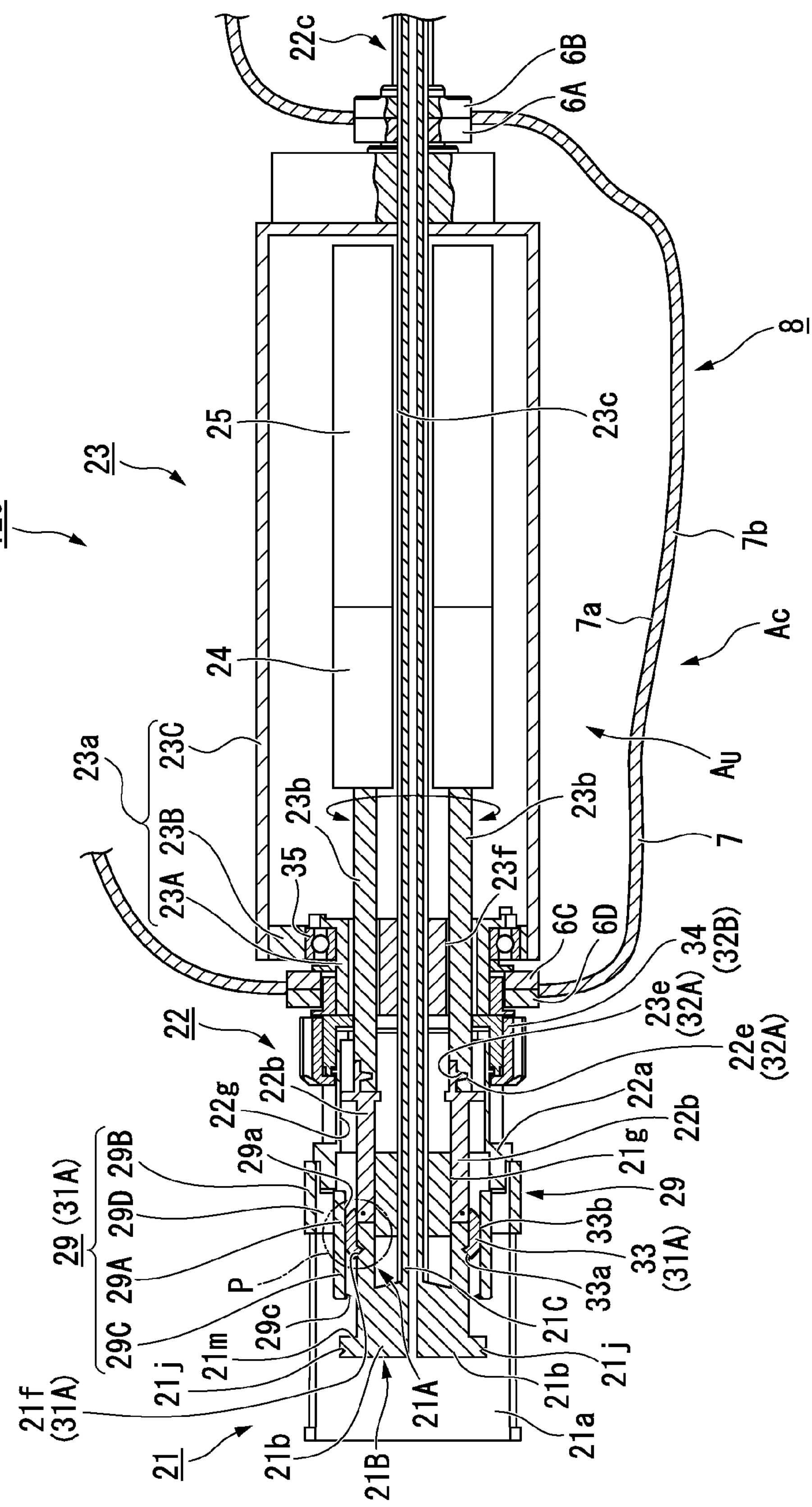
FIG. 12 is a schematic cross-sectional view showing a specific configuration of the operation support device according to the second embodiment of the present invention in the axial direction.
Figure 13:
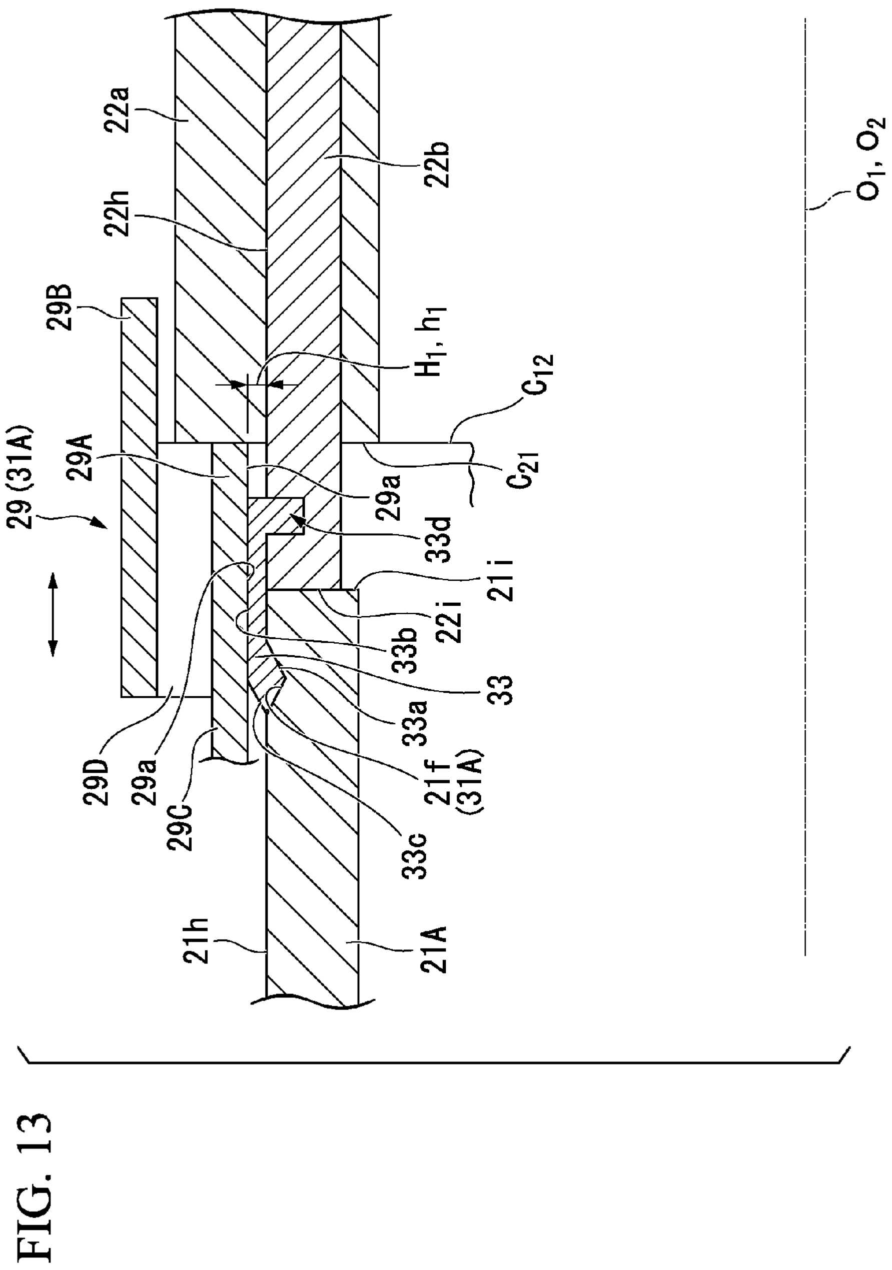
FIG. 13 is a partially enlarged view showing a portion P of FIG. 12.
Figure 14:
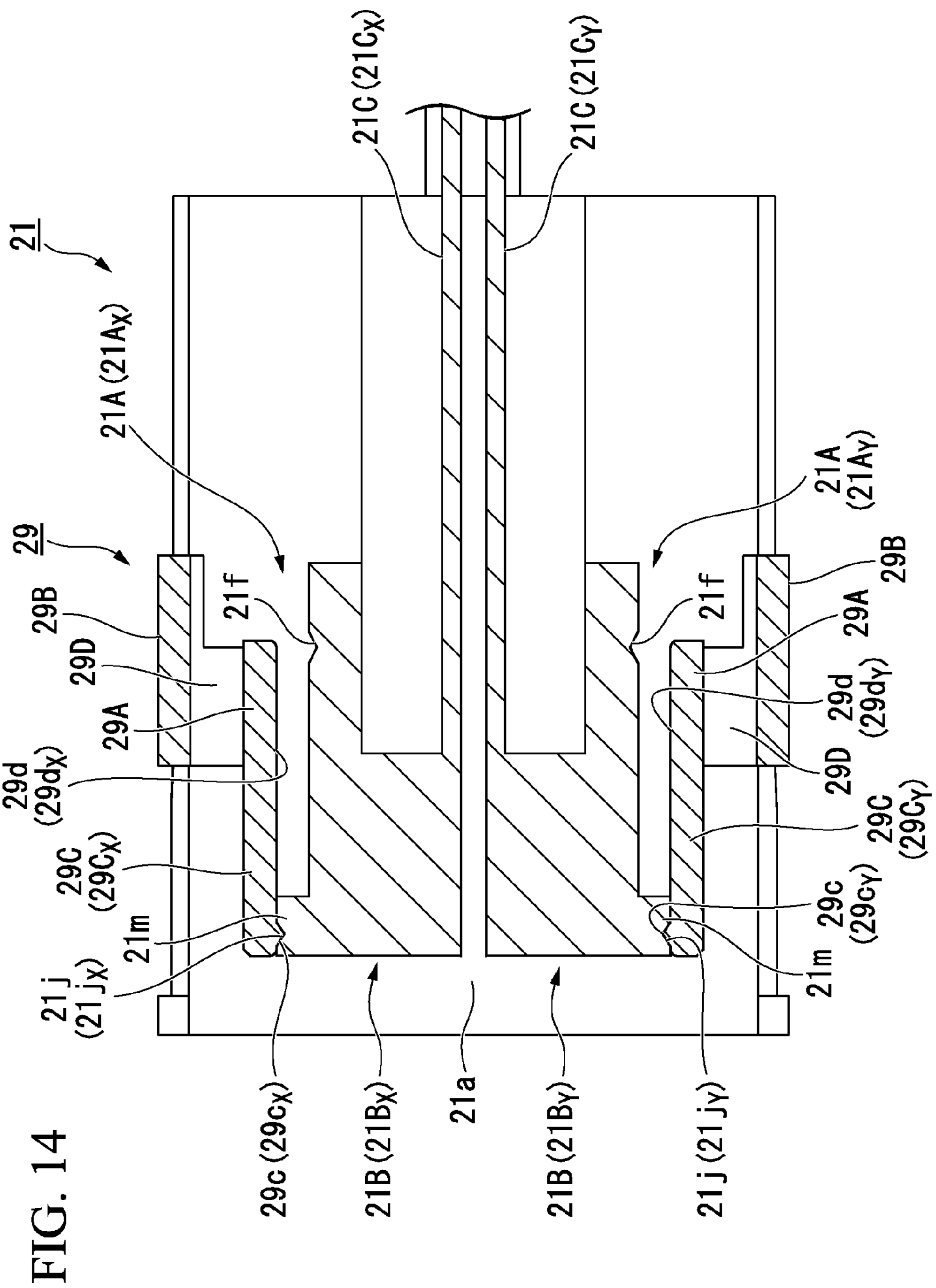
FIG. 14 is a schematic cross-sectional view showing an engaged state of a shaft fixing member engaging section and a second shaft engaging section of the operation support device according to the second embodiment of the present invention in the axial direction.
Figure 15A:
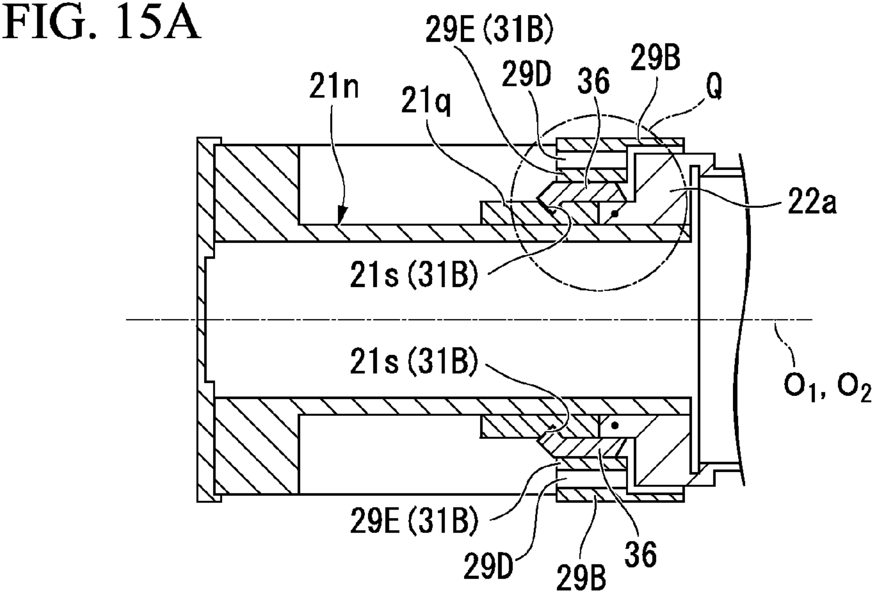
FIG. 15A is a schematic cross-sectional view showing a configuration of main parts of a surgical instrument unit and an intermediate member of the operation support device according to the second embodiment of the present invention in the axial direction.
Figure 15B:
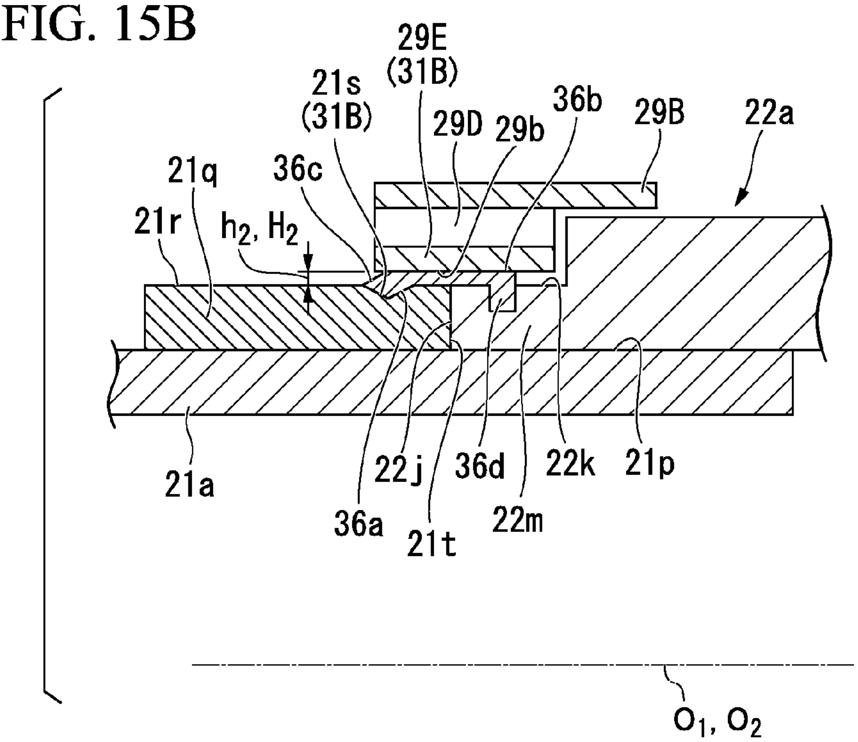
FIG. 15B is a partially enlarged view of a portion Q of FIG. 15A.

FIG. 8 is a schematic perspective view showing an appearance of main parts of an operation support device according to the second embodiment of the present invention. FIG. 9 is a schematic cross-sectional view of the main parts of the operation support device according to the second embodiment of the present invention upon connection in an axial direction. FIG. 10 is a schematic cross-sectional view of the main parts of the operation support device according to the second embodiment of the present invention upon disconnection in the axial direction. FIG. 11 is a schematic cross-sectional view of a surgical instrument unit drive unit and an intermediate member of the operation support device according to the second embodiment of the present invention upon connection in the axial direction. FIG. 12 is a schematic cross-sectional view showing a specific configuration of the operation support device according to the second embodiment of the present invention in the axial direction. FIG. 13 is a partially enlarged view showing a portion P of FIG. 12. FIG. 14 is a schematic cross-sectional view showing an engaged state of a shaft fixing member engaging section and a second shaft engaging section of the operation support device according to the second embodiment of the present invention in the axial direction. FIG. 15A is a schematic cross-sectional view showing a configuration of main parts of a surgical instrument unit and an intermediate member of the operation support device according to the second embodiment of the present invention in the axial direction. FIG. 15B is a partially enlarged view of a portion Q of FIG. 15A.

An operation support device 120 according to the present embodiment includes a surgical instrument driving unit 23 (a driving force supply unit), an intermediate member 22, and a surgical instrument unit 21, instead of the surgical instrument driving unit 3, the intermediate member 2, and the treatment tool unit 1 included in the operation support device 100 according to the first embodiment as shown in FIG. 1, respectively.

In addition, the sterilization treatment is performed on the intermediate member 22 and the surgical instrument unit 21. Further, the sterilization treatment is not performed on the surgical instrument driving unit 23.

Hereinafter, the second embodiment will be described focusing on differences from the first embodiment.

As shown in FIG. 8, in the operation support device 120, the surgical instrument driving unit 23 and the intermediate member 22, the intermediate member 22 and the surgical instrument unit 21 are detachably connected to each other in the axial direction shown by an arrow D. Accordingly, the operation support device 120 has substantially a shaft-shaped appearance extending from the proximal end side to the distal end side as a whole.

Hereinafter, a schematic shape and a positional relation of respective components will be described, and then a connecting structure thereof will be described.

The surgical instrument driving unit 23 is configured to generate displacement or a force (hereinafter, simply referred to as "a driving force") for operating the surgical instrument unit 21 based on a control signal from a drive control unit (not shown) and transmitting the displacement or force to the surgical instrument unit 21. The driving force may be indirectly or directly transmitted. In the present embodiment, as will be described below, the driving force is indirectly transmitted via an intermediate shaft 22*b* of the intermediate member 22.

As shown in FIGS. 9 and 10, the surgical instrument driving unit 23 includes a surgical instrument driving unit support 23*a*. A motor unit 25, a linear driving conversion unit 24, and a driving force transmission shaft 23*b* are installed in the surgical instrument driving unit support 23*a*. Moreover, the surgical instrument driving unit 23 includes the motor 4 and the transmission mechanism 5, similar to the first embodiment.

In addition, FIGS. 9 and 10 are schematic views showing a simplified connection relation, and specific shapes are appropriately omitted or exaggerated. For example, an end portion of the driving force transmission shaft 23*b* is shown at a position aligned with a connection end portion $C_{32}$. However, in an actual connecting motion, as will be described below, an end portion of the driving force transmission shaft 23*b* protrudes toward a side of the intermediate member 22.

The surgical instrument driving unit support 23*a* includes a tubular section 23*c* having a through-hole portion 23*d* through which the intermediate member 22 can pass, a shaft rotating member 23A having an annular portion 23*g* projecting in the radial direction toward the proximal end side of the tubular section 23*c*, a side plate portion 23B configured to rotatably hold the shaft rotating member 23A via a bearing 35*a* in an outer circumferential section of the annular portion 23*g*, a side plate portion 23D configured to rotatably hold the shaft rotating member 23A via a bearing 35*b* in a distal end side of the tubular section 23*c*, and a housing 23C joined with an outer circumferential side of the side plate portions 23B and 23D and covering an outer circumferential side of the surgical instrument driving unit support 23*a*.

The bearings 35*a* and 35*b* in the side plate portions 23B and 23D define a rotation central axis of the shaft rotating member 23A, similar to the bearing 3*b* according to the first embodiment. Hereinafter, the rotation central axis is referred to as a central axis $O_{23}$.

In the surgical instrument driving unit support 23*a*, each of the linear driving conversion units 24 and the motor units 25 is fixed in the surgical instrument driving unit support 23*a* surrounded by the outer circumferential section of the shaft rotating member 23A, the side plate portions 23B and 23D, and the housing 23C.

The motor 4 is installed at the side plate portion 23D. The shaft rotating member 23A is configured to rotate about the central axis $O_{23}$ via the driven pulley 5*c* fixed to the outer circumferential section of the tubular section 23*c* of the shaft rotating member 23A.

As shown in FIG. 10, the connection end portion $C_{32}$ in contact with the intermediate member 22 upon connection is formed at the proximal end side of the annular portion 23*g* of the shaft rotating member 23A.

The motor unit 25 is a motor rotated based on a control signal from a drive control unit (not shown). An output shaft (not shown) is connected to the linear driving conversion unit 24. As a specific configuration of the motor unit 25, for example, a DC motor, or the like may be employed.

The linear driving conversion unit 24 is a member for converting a rotation output of the motor unit 25 into linear driving movement in a direction along the central axis $O_{23}$ of the through-hole portion 23*d*. A configuration of the linear driving conversion unit 24 is not particularly limited as long as the rotation can be converted into the linear driving movement. As the linear driving conversion unit 24, for example, a lead screw mechanism, or the like may be used.

The driving force transmission shaft 23*b* is a shaft member linearly driven by the linear driving conversion unit 24. The driving force transmission shaft 23*b* is movably supported to a direction parallel to the central axis $O_{23}$ at a position spaced apart from the central axis $O_{23}$ in the radial direction in the surgical instrument driving unit support 23*a*.

In addition, the driving force transmission shaft 23*b* is disposed adjacent to the connection end portion $C_{32}$, and according to necessity, can protrude toward a side of the intermediate member 22 rather than the connection end portion $C_{32}$ or retract toward a side of the surgical instrument driving unit 23. In the present embodiment, as shown in FIG. 12, the driving force transmission shaft 23*b* is connected in a state in which the end portion of the driving force transmission shaft 23*b* protrudes toward a side of the intermediate member 22.

While a shape of a cross-section perpendicular to the axial direction of the driving force transmission shaft 23*b* is not particularly limited, for example, a rectangular cross-section can be used.

Each number of the driving force transmission shafts 23*b*, the linear driving conversion units 24, and the motor units 25 can be set to an appropriate number of one or more in accordance with the number of drive inputs necessary for driving of the surgical instrument unit 21.

Hereinafter, as shown in FIG. 10, as an example, a case in which pairs of the driving force transmission shafts 23*b*, the linear driving conversion units 24, and the motor units 25 having the same configuration and having a positional relation in which the pairs of the driving force transmission shafts 23*b*, the linear driving conversion units 24, and the motor units 25 are symmetrical with respect to the central axis $O_{23}$ are provided will be described.

For this reason, in the respective drawings, when the members having the same shape are clearly installed symmetrically with respect to a central axis such as the central axis $O_{23}$, for the convenience of illustration, reference numerals of one side may be omitted, or reference numerals included in one member may be divided to designate two members that are symmetrical with respect to each other.

The intermediate member 22 is a member configured to detachably connect the surgical instrument driving unit 23 and the surgical instrument unit 21 and to transmit a driving force from the surgical instrument driving unit 23 toward a side of the surgical instrument unit 21. In addition, the intermediate member 22 connects the surgical instrument unit 21, on which the sterilization treatment has been performed, to the surgical instrument driving unit 23, on which the sterilization treatment is not performed, with no contact.

As shown in FIG. 10, the intermediate member 22 is a substantially tubular member in which a central axis $O_{22}$ is a central axis. The intermediate member 22 includes an intermediate member support 22*a* (a first support) having a connecting section 22A and a tubular section 22B disposed from the proximal end side to the distal end side, and the intermediate shafts 22*b* (intermediate shaft sections, first shaft sections) in which the number thereof is same as the number of the driving force transmission shafts 23*b*, which are detachably engaged with the respective driving force transmission shafts 23*b* of the surgical instrument driving unit 23 and receive driving forces from the respective driving force transmission shafts 23*b* to transmit the driving forces toward the surgical instrument unit 21 upon engagement.

The connecting section 22A is a support section spread in an annular region sandwiched between a connection end portion $C_{23}$ in contact with the connection end portion $C_{32}$ of the surgical instrument driving unit 23 in the axial direction upon connection, and a connection end portion $C_{21}$ formed at the proximal end portion opposite to the connection end portion $C_{23}$ and in contact with the surgical instrument unit 21 in the axial direction upon connection.

A guide groove 22*g* configured to position and hold the respective intermediate shafts 22*b* at positions in the circumferential direction and the radial direction, and to slidably hold them in the axial direction is formed in the connecting section 22A. The guide groove 22*g* is formed to penetrate from the connection end portion $C_{23}$ toward the connection end portion $C_{21}$.

The respective intermediate shafts 22*b* can be positioned to face the respective intermediate shafts 22*b* of the surgical instrument unit 21 and also to face the respective driving force transmission shafts 23*b* of the surgical instrument driving unit 23 by the guide groove 22*g* upon connection.

In addition, while not shown, in order to perform the positioning in the circumferential direction of the intermediate member 22 with respect to the surgical instrument driving unit 23 and the surgical instrument unit 21, an appropriate positioning section is formed in the connecting section 22A.

The tubular section 22B is a tubular support section inserted into and passing through the through-hole portion 23*d* of the surgical instrument driving unit support 23*a*. The tubular section 22B includes an insertion outer circumferential section 22*c* having a shape fitted into the through-hole portion 23*d*.

A surgical instrument unit insertion hole 22*d* into which the surgical instrument unit 21 can be inserted is formed to pass through a center portion of the connecting section 22A and the tubular section 22B in the axial direction.

A shape of a cross-section perpendicular to the axial direction of the intermediate shaft 22*b* is not particularly limited. In the present embodiment, as an example, a rectangular cross-section having two sides facing each other in the radial direction of the intermediate member 22 is employed.

As shown in FIG. 9, a support attachment/detachment mechanism unit 32B detachably engaged with the intermediate member support 22*a* and the surgical instrument driving unit support 23*a*, and a shaft attachment/detachment mechanism unit 32A detachably engaged with the intermediate shaft 22*b* and the driving force transmission shaft 23*b* are installed between the intermediate member 22 and the surgical instrument driving unit 23.

In the present embodiment, as shown in FIG. 12, in the support attachment/detachment mechanism unit 32B, a configuration in which in a state in which the intermediate member support 22*a* abuts the proximal end portion of the shaft rotating member 23A, they are engaged with an engaging section (not shown) to be fixed by a well-known fixing ring 34 is employed.

However, when the engagement by the fixing ring 34 is fixed, the drape rings 6C and 6D of the drape assembly 8 are fitted onto the outer circumferential section of the end portion of the distal end side of the intermediate member support 22*a*, and engagement is fixed in a state in which the drape rings 6C and 6D are interposed between the surgical instrument driving unit 23 and the outer circumferential section.

In addition, the drape rings 6A and 6B of the drape assembly 8 are fixed to the distal end side of the tubular section 22B of the intermediate member 22.

For this reason, as shown in FIG. 11, even in the intermediate member 22, similar to the first embodiment, a surface of the outer circumferential insertion section 22*c* sandwiched between the drape rings 6D and 6A constitutes the first surface section $S_1$ continued into the surface 7*a* of the drape 7. For this reason, upon connection, the first surface section $S_1$ fronts the shaft rotating member 23A in the through-hole portion 23*d*.

In the intermediate member 22, surfaces of the connecting section 22A and the outer circumferential insertion section 22*c* of the proximal end side other than the drape ring 6D, an inner circumferential surface of the surgical instrument unit insertion hole 22*d*, and a surface of the tubular section 22B of the distal end side other than the drape ring 6B constitute the second surface section $S_2$ continued into the surface 7*b* of the drape 7.

That is, in the operation support device 120, the surgical instrument driving unit 23 is disposed in the unclean area $A_U$ covered by the surface 7*a* of one side of the drape 7. In addition, the surgical instrument unit 21 fronts the surface 7*b* which is a rear face of the surface 7*a*, and is disposed in the clean area $A_U$ spaced apart from the unclean area $A_U$ using the drape 7 and the intermediate member 22 as a boundary.

In the present embodiment, as shown in FIG. 12, the shaft attachment/detachment mechanism unit 32A is constituted by a shaft engaging section 23*e* and a shaft engaging section 22*e*.

The shaft engaging section 23*e* is formed at the end portion of the driving force transmission shaft 23*b* constituting the proximal end side in the surgical instrument driving unit 23.

The shaft engaging section 22*e* is formed at the end portion of the intermediate shaft 22*b* constituting the distal end side in the intermediate member 22, and configured to be detachably engaged with the shaft engaging section 23*e*.

As the shaft engaging sections 23*e* and 22*e*, a well-known configuration constituted by concave and convex sections detachably engaged with each other may be appropriately employed.

As shown in FIG. 10, the surgical instrument unit 21 has an operating unit 21*c*, which is a surgical instrument configured to manipulate a manipulated subject at the distal end side. The surgical instrument unit 21 is configured to drive the operating unit 21*c* by the driving force transmitted from the surgical instrument driving unit 23 via the intermediate member 22 to manipulate the manipulation subject. The surgical instrument unit 21 is detachably installed with respect to the intermediate member 22 in the axial direction.

The operating unit 21*c* of the surgical instrument unit 21 can use an appropriate configuration as long as the operating unit can be moved by one or more driving forces in one axial direction. For example, as the operating unit of the surgical instrument unit, a configuration such as forceps constituted by two forceps pieces, a joint for changing a direction of the forceps, a stapler, and a curved section of an endoscope that can be curved in one or two directions or the like may be used.

As shown in FIG. 10, the surgical instrument unit 21 has substantially a shaft shape as a whole. The surgical instrument unit 21 includes a surgical instrument unit support 21*a* (a second support) connected to the intermediate member 22, and the driving force transmission members 21*b* in which the number thereof is same as the number of the intermediate shafts 22*b*, which are detachably engaged with the intermediate shafts 22*b* of the intermediate member 22 and receiving driving forces from the intermediate shafts 22*b* to transmit the driving forces toward a side of the operating unit 21*c* upon engagement.

The surgical instrument unit support 21*a* has a connection end portion $C_{12}$ in contact with the connection end portion $C_{21}$ of the intermediate member 22 upon connection. A box-shaped section 21*e* movably supporting a part of the driving force transmission member 21*b* in the same direction as the moving direction of the intermediate shaft 22*b* upon connection and a tubular section 21*d* extending toward the distal end side coaxial with a central axis $O_{21}$ of the box-shaped section 21*e* are formed in the surgical instrument unit support 21*a*.

A guide groove 21*g* slidably holding one end portion of the respective driving force transmission members 21*b* in the axial direction is formed in the connection end portion $C_{12}$ side of the box-shaped section 21*e*.

The respective driving force transmission members 21*b* are positioned at positions in the circumferential direction and radial direction that can face the intermediate shafts 22*b* of the intermediate member 22 upon connection by the guide groove 21*g*.

The tubular section 21*d* has an outer diameter such that the tubular section 21*d* can be inserted into the surgical instrument unit insertion hole 22*d* of the intermediate member 22 and a length larger than the surgical instrument unit insertion hole 22*d*. The operating unit 21*c* is connected to the distal end portion of the tubular section 21*d*.

The driving force transmission member 21*b* is a shaft-shaped member having a shape which is curved in substantially J shape. The driving force transmission member 21*b* includes an input side transmission shaft section 21A (a surgical instrument unit shaft section, a second shaft section), a connecting section 21B, and an output side transmission shaft section 21C.

The input side transmission shaft section 21A is installed so as to be able to engage with the intermediate shaft 22*b*. The input side transmission shaft section 21A is a shaft section configured to receive a driving force from the intermediate shaft 22*b* upon engagement with the intermediate shaft 22*b*. The input side transmission shaft section 21A is movably held in the axial direction parallel to the central axis $O_{21}$ by the guide groove 21*g* of the box-shaped section 21*e*.

A shape of a cross-section perpendicular to the axial direction of the input side transmission shaft section 21A is not particularly limited. In the present embodiment, as an example, a rectangular cross-section having two sides facing each other in the radial direction of the surgical instrument unit 21 is used.

The connecting section 21B is a section formed from the end portion of the proximal end side of the input side transmission shaft section 21A toward the central axis $O_{21}$. The connecting section 21B connects the end portion of the proximal end side of the output side transmission shaft section 21C to the end portion of the proximal end side of the input side transmission shaft section 21A.

In the present embodiment, as shown in FIG. 12 (not shown in FIGS. 9 and 10), a step-shaped protrusion section 21*m* protruding outward in the radial direction is formed at the proximal end side of the connecting section 21B. An engaging concave section 21*j* (a second shaft engaging section) engaged with an engaging protrusion 29*c* of a rod-shaped portion 29C described later is formed at the end portion in the radial direction of the step-shaped protrusion section 21*m*.

The output side transmission shaft section 21C is a shaft section extending from the connecting section 21B toward the distal end side of the surgical instrument unit 21 in an orientation parallel to the central axis $O_{21}$. The output side transmission shaft section 21C is housed in the box-shaped section 21*e* and the tubular section 21*d*, and the distal end portion thereof is connected to the operating unit 21*c*.

As the output side transmission shaft section 21C, an appropriate member that can manipulate the operating unit 21*c*, for example, a rod, a wire, or the like, may be used. When the operating unit 21*c* is a curved section of an endoscope, or the like, as the output side transmission shaft section 21C, a shaft section having flexibility and can be curved may be used.

The driving force transmission member 21*b* can be formed by appropriately joining a plurality of members formed of separate materials appropriate for the input side transmission shaft section 21A, the connecting section 21B, and the output side transmission shaft section 21C, respectively. Meanwhile, the driving force transmission member 21*b* may be integrally formed.

As shown in FIG. 9, a shaft attachment/detachment mechanism unit 31A configured to detachably engage the input side transmission shaft section 21A and the intermediate shaft 22*b*, and a support attachment/detachment mechanism unit 31B configured to detachably engage the surgical instrument unit support 21*a* and the intermediate member support 22*a* are installed between the surgical instrument unit 21 and the intermediate member 22.

Here, the shaft attachment/detachment mechanism units 31A are installed in which the number of the shaft attachment/detachment mechanism units is same as the number of the input side transmission shaft sections 21A and the intermediate shafts 22*b* are installed. The shaft attachment/detachment mechanism units 31A are configured by members having the same configuration.

In addition, the support attachment/detachment mechanism unit 31B may be installed at least one place. The support attachment/detachment mechanism unit 31B is preferably formed at a plurality of places spaced apart from each other in the circumferential direction. Hereinafter, as an example, a case in which a pair of support attachment/detachment mechanism units 31B are installed to face each other with the central axes $O_{21}$ and $O_{22}$ interposed therebetween will be described.

In addition, since FIGS. 9 and 10 are schematic views, the support attachment/detachment mechanism unit 31B and the shaft attachment/detachment mechanism unit 31A are shown on the same cross-section. However, in actuality, in order to avoid interference with each other, the support attachment/detachment mechanism unit 31B and the shaft attachment/detachment mechanism unit 31A are formed on different cross-sections. However, if disposition is possible, the support attachment/detachment mechanism unit 31B and the shaft attachment/detachment mechanism unit 31A may be disposed on the same cross-section.

In the present embodiment, as shown in FIG. 12, the shaft attachment/detachment mechanism unit 31A includes an engaging concave section 21*f* (a first shaft engaging section), a hook portion 33 (a shaft connecting member), and an attachment/detachment ring 29 (a shaft fixing member, support fixing member).

The engaging concave section 21*f* is a shaft engaging section for engaging the input side transmission shaft section 21A with the intermediate shaft 22*b*. As shown in FIG. 13, the engaging concave section 21*f* is installed at an outer circumferential side surface 21*h* outside in the radial direction (an upper side of FIG. 13) in the distal end side (a right side of FIG. 13) of the input side transmission shaft section 21A. In the present embodiment, the engaging concave section 21*f* has a cross-section with a V-shaped groove in the axial direction.

In the present embodiment, the engaging concave section 21*f* is formed at a position such that a distal end surface 21*i* of the input side transmission shaft section 21A upon engagement of the hook portion 33 described later abuts a proximal end surface 22*i* of the intermediate shaft 22*b* in the axial direction. However, when there is no obstacle to transmission of the driving force due to a shape or strength of the hook portion 33, the engaging concave section 21*f* may be formed at a position for engagement in a state in which the distal end surface 21*i* and the proximal end surface 22*i* are spaced apart from each other.

The hook portion 33 is a rod-shaped member having a width (a width in a depth direction of FIG. 13) which is substantially the same as the width of the intermediate shaft 22*b* and the input side transmission shaft section 21A. One end side of the hook portion 33 is turnably fixed to the proximal end portion of the intermediate shaft 22*b* via a hinge portion 33*d*. The hook portion 33 is disposed on an outer circumferential side surface 22*h* outside in the radial direction of the intermediate shaft 22*b*.

However, a turning range of the hook portion 33 may be set to a small angular range such that an engaging protrusion 33*a* described later is moved to a position which is substantially the same as the outer circumferential side surface 22*h*.

In addition, the hinge portion 33*d* may be configured to bias the hook portion 33 including, for example, an elastic member or a spring, in a direction to be in close contact with the outer circumferential side surface 22*h*.

Further, the hook portion 33 has a length such that the other end portion protrudes toward the proximal end side rather than the proximal end surface 22*i* of the intermediate shaft 22*b* in an orientation parallel to the intermediate shaft 22*b* as shown in FIG. 13. In the other end portion, the engaging protrusion 33*a* (the shaft connection engaging section) having a mount shape cross-section engaged with the engaging concave section 21*f* is formed inside in the radial direction.

The engaging protrusion 33*a* is formed at a position such that the distal end surface 21*i* of the input side transmission shaft section 21A abuts the proximal end surface 22*i* of the intermediate shaft 22*b*, and the outer circumferential side surfaces 21*h* and 22*h* are perfectly engaged with the engaging concave section 21*f* in a state in which the outer side surfaces are aligned with each other.

In addition, a thickness of an intermediate section, other than the engaging protrusion 33*a* and the hinge portion 33*d* in the hook portion 33, is set to $h_1$. For this reason, in the engagement state shown in FIG. 13, an outer circumferential surface 33*b* of the hook portion 33 configures a flat surface protruding outward in the radial direction by the height $h_1$ from the outer circumferential side surfaces 21*h* and 22*h*.

Further, a taper 33*c* inclined from one end side of the outer circumferential surface 33*b* toward the other end is formed at a rear side of the engaging protrusion 33*a* in the other end side of the engaging protrusion 33*a*.

The attachment/detachment ring 29 includes an outer circumferential ring section 29B movably supported on the outer circumferential section of the box-shaped section 21*e* in the axial direction, an inner circumference pressing section 29A (a shaft fixing member) movably supported in the box-shaped section 21*e* in the axial direction, and a connecting section 29D configured to connect the outer circumferential ring section 29B and the inner circumference pressing section 29A in the radial direction to interlock movement thereof.

The connecting section 29D is inserted into a through-hole (not shown) in a housing section constituting the outer circumferential section of the box-shaped section 21*e*.

The inner circumferential surface of the inner circumference pressing section 29A is configured to have a size so as to be able to cover at least the hook portion 33 in the circumferential direction. A position restricting surface 29*a* spaced apart outward in the radial direction by $H_1$ with respect to the outer circumferential side surface 21*h* is formed at the inner circumferential surface of the inner circumference pressing section 29A. A length in the axial direction of the position restricting surface 29*a* is set to be larger than a length of an allowable moving amount of the input side transmission shaft section 21A in use of the surgical instrument unit 21 added to the length of the hook portion 33.

A height $H_1$ of the position restricting surface 29*a* is set to a dimension such that the hook portion 33 is sandwiched between the outer circumferential side surfaces 21*h* and 22*h* and the position restricting surface 29*a* in a state in which engagement between the engaging concave section 21*f* and the engaging protrusion 33*a* is maintained, and the hook portion 33 is slidable in the axial direction. In the present embodiment, the height $H_1$ of the position restricting surface 29*a* is a dimension in which a margin with respect to a manufacturing error or an assembly error of the hook portion 33 and the inner circumference pressing section 29A is added to $h_1$, and is set such that the hook portion 33 is sandwiched therebetween with almost no gap.

In addition, the inner circumference pressing section 29A can move in the axial direction between a shaft engagement fixing position of the distal end side in which the inner circumference pressing section 29A moves upon connection to fix the engagement state between the engaging concave section 21*f* and the hook portion 33, and a released position, which is a position of the lowermost proximal end side in which the inner circumference pressing section 29A moves upon disconnection.

The inner circumference pressing section 29A at the shaft engagement fixing position is shown in FIG. 12. In addition, the inner circumference pressing section 29A at the released position is shown in FIG. 14.

The rod-shaped portion 29C having the engaging protrusion 29*c* (the shaft fixing member engaging section) detachably engaged with the engaging concave section 21*j* of the connecting section 21B is formed at the end portion of the proximal end side of the inner circumference pressing section 29A such that further extending toward the proximal end side.

The rod-shaped portion 29C is a section having elasticity to enable elastic deformation in the radial direction. An inner circumferential side surface 29*d* inside in the radial direction is aligned to the same height as the step-shaped protrusion section 21*m* of the connecting section 21B.

For this reason, when the inner circumference pressing section 29A is moved to the proximal end side, the engaging protrusion 29*c* abuts the step-shaped protrusion section 21*m*, and the connecting section 21B is pressed against the proximal end side. Accordingly, the connecting section 21B is moved together with the rod-shaped portion 29C to the proximal end side to some extent. However, as shown in FIG. 14, when the connecting section 21B arrives at a moving limit of the proximal end side, as the rod-shaped portion 29C is bent outward in the radial direction, the engaging concave section 21*j* is engaged with the engaging protrusion 29*c*.

A length of the rod-shaped portion 29C is a length such that, in a state in which the engaging protrusion 29*c* and the engaging concave section 21*j* are engaged with each other, the position restricting surface 29*a* is released to the proximal end side rather than the engaging concave section 21*f*, and an outside in the radial direction of the engaging concave section 21*f* is opened.

In addition, the attachment/detachment ring 29 of the present embodiment includes an inner circumference pressing section 29E constituting a part of the support attachment/detachment mechanism unit 31B as shown in FIG. 15A in a cross-section having different positions in the circumferential direction from FIG. 13. The inner circumference pressing section 29E will be described below in detail.

In the present embodiment, as shown in FIGS. 15A and 15B, the support attachment/detachment mechanism unit 31B includes an engaging concave section 21*s* (a support engaging section), a hook portion 36 (a support connecting member), and the inner circumference pressing section 29E (a support fixing member).

In addition, the support attachment/detachment mechanism unit 31B may be disposed on the same cross-section as the cross-section in which the shaft attachment/detachment mechanism unit 31A is installed. In the present embodiment, the support attachment/detachment mechanism unit 31B is disposed on a cross-section different from the cross-section in which the shaft attachment/detachment mechanism unit 31A is installed, for example, a cross-section in which an angle is moved in the circumferential direction is moved.

The engaging concave section 21*s* is a support engaging section configured to engage the intermediate member support 22*a* with the surgical instrument unit support 21*a*. As shown in FIG. 15B, the engaging concave section 21*s* is formed on a step-shaped section 21*q* installed to extend in the axial direction toward a bottom portion of a groove section 21*n* formed at the distal end side of the surgical instrument unit support 21*a*. In the present embodiment, the engaging concave section 21*s* is configured by a groove section having a V-shaped cross-section in the axial direction.

An insertion guide section 21*p* installed parallel to the central axis $O_1$ to guide movement in the axial direction of an insertion section 22*m* protruding toward the proximal end portion of the intermediate member support 22*a* is formed at the distal end side of the step-shaped section 21*q*.

A thickness in the radial direction of the insertion section 22*m* is equal to a height of the step-shaped section 21*q* from the insertion guide section 21*p*. For this reason, an outer circumferential side surface 22*k* of the insertion section 22*m* and an upper surface 21*r* of the step-shaped section 21*q* are aligned in the engagement state as shown in FIG. 15B.

In the present embodiment, the engaging concave section 21*s* is formed at a position such that a distal end surface 21*t* of the step-shaped section 21*q* abuts a proximal end surface 22*j* of the insertion section 22*m* of the intermediate member support 22*a* upon engagement of the hook portion 36 be described later in the axial direction. However, when there is no obstacle to engagement force due to a shape or strength of the hook portion 36, the engaging concave section 21*s* may be formed at a position such that the distal end surface 21*t* and the proximal end surface 22*i* are spaced apart from each other.

The hook portion 36 is a rod-shaped member having a width (a width in the depth direction of FIG. 15B) such that the hook portion 36 can be engaged with the engaging concave section 21*s*. One end side of the hook portion 36 is turnably fixed to the insertion section 22*m* of the intermediate member support 22*a* via a hinge portion 36*d*. The hook portion 36 is disposed on the outer circumferential side surface 22*k* of the insertion section 22*m*. However, a turning range of the hook portion 36 is preferably set to a small angular range such that an engaging protrusion 36*a* described later is moved to the same position as the outer circumferential side surface 22*k*.

In addition, the hinge portion 36*d* may be configured so as to include, for example, an elastic member or a spring, and to bias the hook portion 36 in a direction to be in close contact with the outer circumferential side surface 22*k*.

Further, the hook portion 36 has a length such that the other end portion protrudes toward the proximal end side rather than the proximal end surface 22*j* in an orientation parallel to the insertion section 22*m* as shown in FIG. 15B. The engaging protrusion 36*a* (the support connection engaging section) having a mount shape cross-section engaged with the engaging concave section 21*s* is formed at the other end portion inside in the radial direction.

The engaging protrusion 36*a* is formed at a position such that the distal end surface 21*t* abuts the proximal end surface 22*j*, and in a state in which the upper surface 21*r* is aligned with the outer circumferential side surface 22*k*, the engaging protrusion 36*a* can be perfectly engaged with the engaging concave section 21*f*.

In addition, a thickness of an intermediate section, other than the engaging protrusion 36*a* and the hinge portion 36*d* in the hook portion 36, is set to $h_2$. For this reason, in the engagement state shown in FIG. 15B, an outer circumferential surface 36*b* of the hook portion 36 constitutes a flat surface protruding outward in the radial direction by the height $h_2$ from the upper surface 21*r* and the outer circumferential side surface 22*k*.

Further, a taper 36*c* inclined from one end side of the outer circumferential surface 36*b* toward the other end is formed at a rear side of the engaging protrusion 36*a* in the other end side of the engaging protrusion 36*a*.

The inner circumferential surface of the inner circumference pressing section 29E is configured to have a size to cover at least the hook portion 36 in the circumferential direction. A position restricting surface 29*b* spaced apart from the upper surface 21*r* outward in the radial direction by $H_2$ is formed at the inner circumferential surface of the inner circumference pressing section 29E. A length in the axial direction of the position restricting surface 29*b* is set to a length such that the hook portion 36 is pressed in the radial direction from the outside when the attachment/detachment ring 29 is moved to the shaft engagement fixing position.

The hook portion 36 is not moved in the axial direction when the engagement state is fixed. For this reason, a length in the axial direction of the position restricting surface 29*b* may be set to a dimension smaller than the entire length of the hook portion 36.

The height $H_2$ of the position restricting surface 29*b* is set to a dimension such that the hook portion 36 is sandwiched between the upper surface 21*r*, the outer circumferential side surface 22*k* and the position restricting surface 29*b* in a state in which engagement between the engaging concave section 21*s* and the engaging protrusion 36*a* is maintained, and the hook portion 36 is slidable in the axial direction. In the present embodiment, the height $H_2$ of the position restricting surface 29*b* is a dimension in which a margin with respect to a manufacturing error or an assembly error of the hook portion 36 and the inner circumference pressing section 29E is added to $h_2$, and the hook portion 36 is sandwiched therebetween with almost no gap.

As described above, the support attachment/detachment mechanism unit 31B of the present embodiment has a configuration housed in the groove section 21*n* upon mounting. For this reason, an example in which the support attachment/detachment mechanism unit 31B according to the present embodiment is installed in the surgical instrument unit support 21*a* and the intermediate member support 22*a* will be described.

Next, an action of the operation support device 120 having the above-mentioned configuration will be described focusing on an assembly method and an attachment/detachment method.

Figure 16A:
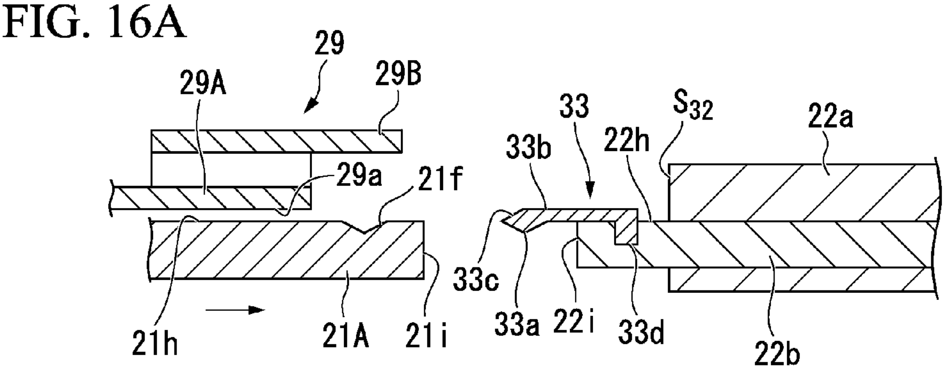
FIG. 16A is a schematic view for describing an engagement motion of an intermediate shaft section and a surgical instrument unit shaft section of the operation support device according to the second embodiment of the present invention.

FIGS. 16A, 16B, 16C and 16D are schematic views for describing an engagement motion of the intermediate shaft section and the surgical instrument unit shaft section of the operation support device according to the second embodiment of the present invention. FIGS. 17A and 17B are schematic views for describing a motion of the intermediate shaft section and the surgical instrument unit shaft section of the operation support device according to the second embodiment of the present invention upon engagement. FIGS. 18A, 18B, 18C and 18D are schematic views for describing an engagement motion of the intermediate member support and the surgical instrument unit support of the operation support device according to the second embodiment of the present invention.

The surgical instrument driving unit 23, the intermediate member 22, and the surgical instrument unit 21 of the operation support device 120 are different from the first embodiment in that, after connection thereof, the rotary driving force about the central axis $O_{23}$ is transmitted by the surgical instrument driving unit 23, and further, the linear driving force by the respective motor units 25 and the respective linear driving conversion units 24 is transmitted to the surgical instrument unit 21 to drive the operating unit 21c.

For this reason, in connection of the surgical instrument driving unit 23, the intermediate member 22, and the surgical instrument unit 21, in addition to connection of the respective supports, connection of the driving force transmission shaft 23b, the intermediate shaft 22b and the input side transmission shaft section 21A is needed.

However, in the present embodiment, in particular, upon connection of the intermediate member 22 and the surgical instrument unit 21, since the shaft attachment/detachment mechanism unit 31A and the support attachment/detachment mechanism unit 31B are used, the assembly can be performed similar to the first embodiment in which only the support is connected.

Hereinafter, the second embodiment will be described focusing on differences from the first embodiment.

In assembly of the operation support device 120, the drape assembly 8 is previously formed. After that, a driving force supply unit installation process, a shielding member disposition process, a first connecting process, and a second connecting process are sequentially performed. Among these, descriptions of the driving force supply unit installation process and the shielding member disposition process will be omitted, because only members of an assembly subject are different and these processes can be easily understood.

In the first connecting process according to the present embodiment, a connecting body of the surgical instrument driving unit 23 and the intermediate member 22 is formed.

Since the connection state of the surgical instrument driving unit 23 and the intermediate member 22 is not released in principal during the operation once the surgical instrument driving unit 23 and the intermediate member 22 are connected to each other, even when attachment/detachment is time-consuming, time loss during the operation does not occur. For this reason, a well-known mechanism (see FIG. 9) is used in the shaft attachment/detachment mechanism unit 32A and the support attachment/detachment mechanism unit 32B according to the present embodiment.

In the shaft attachment/detachment mechanism unit 32A and the support attachment/detachment mechanism unit 32B, first, in a state in which each of the driving force transmission shafts 23b protrudes from the connection end portion $C_{32}$ of the surgical instrument driving unit 23, the intermediate member 22 is inserted into the through-hole portion 23d of the surgical instrument driving unit 23 from the proximal end side. Then, the shaft engaging section 22e and the shaft engaging section 23e are engaged with each other, and the connection end portion $C_{23}$ abuts the connection end portion $C_{32}$. Here, the drape rings 6C and 6D are fitted to the proximal end side of the intermediate member support 22a of the intermediate member 22.

Next, the intermediate member support 22a and the surgical instrument driving unit support 23a are engaged and fixed using the fixing ring 34.

Accordingly, the distal end portion of the tubular section 22B of the intermediate member 22 is exposed to the distal end side of the surgical instrument driving unit 23. For this reason, the drape rings 6A and 6B are fitted onto and fixed to an outer circumference of the distal end portion of the tubular section 22B.

As described above, when the intermediate member 22 is connected to the surgical instrument driving unit 23, as shown in FIG. 11, the surgical instrument driving unit 23 is surrounded by the surface 7a of the drape 7. Then, the unclean area $A_U$ and the clean area $A_U$ are partitioned using the drape 7 and the intermediate member 22 as a boundary. The inside of the surgical instrument unit insertion hole 22d becomes the clean area $A_C$.

Next, the second connecting process is performed.

In this process, the operating unit 21c and the tubular section 21d of the surgical instrument unit 21 are inserted from the proximal end side of the surgical instrument unit insertion hole 22d of the intermediate member 22 connected to the surgical instrument driving unit 23, and a connecting body in which the surgical instrument unit 21 is connected to the intermediate member 22 is formed.

In the present embodiment, connection between the supports and connection between the shaft sections can be performed in parallel by the shaft attachment/detachment mechanism unit 31A and the support attachment/detachment mechanism unit 31B moving in the axial direction.

Hereinafter, first, the attachment/detachment method of the shaft attachment/detachment mechanism unit 31A and the support attachment/detachment mechanism unit 31B will be partially described. After that, the entire attachment/detachment motion will be described.

An attachment/detachment motion of the shaft attachment/detachment mechanism unit 31A will be described with the attachment/detachment method thereof.

In the present method, a shaft engagement process and a shaft engagement fixing process are sequentially performed upon mounting. The shaft engagement fixing release process and a shaft disengagement process are sequentially performed upon dismounting.

The shaft engagement process is a process of engaging the engaging concave section 21f with the engaging protrusion 33a by causing the intermediate member support 22a, which is a first support, and the surgical instrument unit support 21a, which is a second support, to approach each other in a moving direction of the intermediate shaft 22b and the input side transmission shaft section 21A.

The intermediate member support 22a and the surgical instrument unit support 21a have a positioning section (not shown) configured to perform positioning in the circumferential direction. For this reason, the surgical instrument unit support 21a is inserted into the intermediate member support 22a to correspond to the positioning section. Accordingly, as shown in FIG. 16A, the proximal end surface 22i of each of the intermediate shafts 22b and the distal end surface 21i of each of the driving force transmission members 21b approach each other in a state in which the proximal end surface 22i of each of the intermediate shafts 22b and the distal end surface 21i each of the driving force transmission members 21b are faced each other.

Here, the inner circumference pressing section 29A of the attachment/detachment ring 29 is moved with the surgical instrument unit support 21a in a state in which the inner circumference pressing section 29A is disposed at a released position in the surgical instrument unit 21. For this reason, an upper section of the engaging concave section 21f is opened.

Figure 16B:
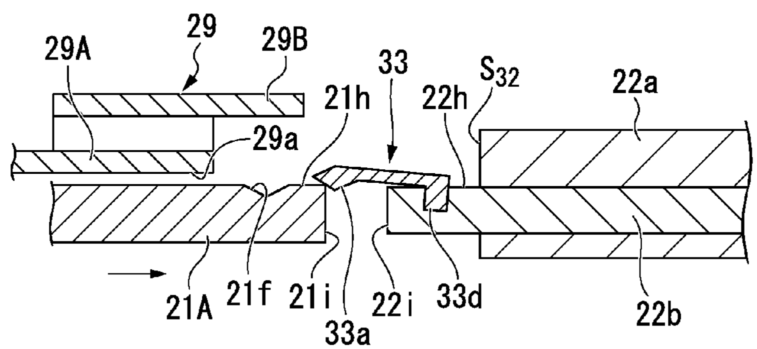
FIG. 16B is a schematic view for describing the engagement motion of the intermediate shaft section and the surgical instrument unit shaft section of the operation support device according to the second embodiment of the present invention.
Figure 17A:
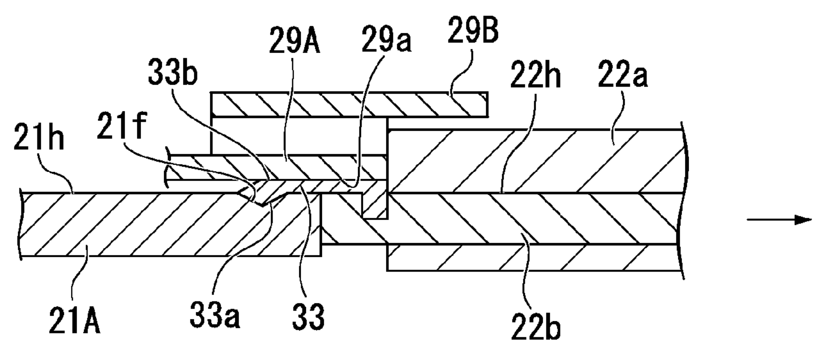
FIG. 17A is a schematic view for describing a motion of the intermediate shaft section and the surgical instrument unit shaft section of the operation support device according to the second embodiment of the present invention upon engagement.
Figure 17B:
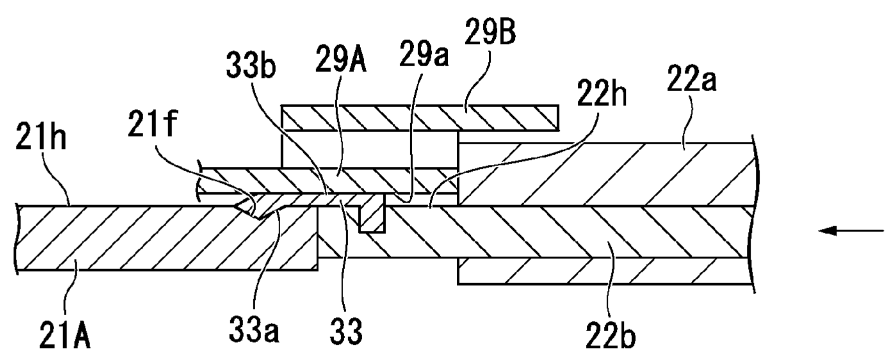
FIG. 17B is a schematic view for describing a motion of the intermediate shaft section and the surgical instrument unit shaft section of the operation support device according to the second embodiment of the present invention upon engagement.

As shown in FIG. 16B, when a distance between the distal end surface 21i and the proximal end surface 22i is reduced, the distal end portion of the input side transmission shaft section 21A abuts the engaging protrusion 33a of the hook portion 33 to rotate the hook portion 33. Further, when the distance between the distal end surface 21i and the proximal end surface 22i is reduced, the engaging protrusion 33a advances a state in which it is riding on the outer circumferential side surface 21h.

Figure 16C:
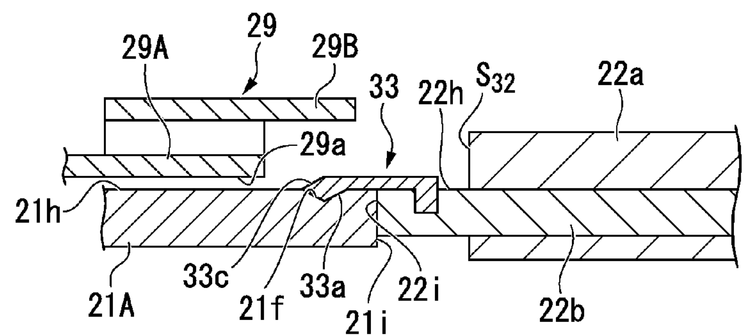
FIG. 16C is a schematic view for describing the engagement motion of the intermediate shaft section and the surgical instrument unit shaft section of the operation support device according to the second embodiment of the present invention.

As shown in FIG. 16C, when the engaging protrusion 33*a* is disposed on the engaging concave section 21*f*, the engaging protrusion 33*a* enters into the engaging concave section 21*f*. Then, the engaging protrusion 33*a* is engaged with the engaging concave section 21*f*.

As described above, the shaft engagement process is finished.

In addition, in this process, the engaging protrusion 33*a* is preferably inserted perfectly into the engaging concave section 21*f* and engaged therewith. Further, a portion of the engaging protrusion 33*a* may enter the inside of the engaging concave section 21*f*. In the present embodiment, a case in which a portion of the engaging protrusion 33*a* enters the inside of the engaging concave section 21*f* is shown. That is, in this process, when the engaging concave section 21*f* and the engaging protrusion 33*a* are spaced apart from each other in the axial direction, a state in which the engaging concave section 21*f* and the engaging protrusion 33*a* are in contact with each other to generate a resistance in the spacing motion is considered as in engagement. However, in this engagement state, when an external force for spacing motion is increased to some extent, the engagement state is released.

In addition, such an engagement state is formed even before the distal end surface 21*i* abuts the proximal end surface 22*i*.

Further, when the hinge portion 33*d* includes a configuration of biasing the hook portion 33 against the outer circumferential side surface 22*h*, in this process, the engaging protrusion 33*a* may securely enter the inside of the engaging concave section 21*f* to obtain a good engagement state.

Next, the shaft engagement fixing process is performed. This process is a process of moving the inner circumference pressing section 29A, which is a shaft fixing member, to press the hook portion 33, and forming a shaft engagement fixing state in which an engagement state with the engaging concave section 21*f* is maintained.

Figure 16D:
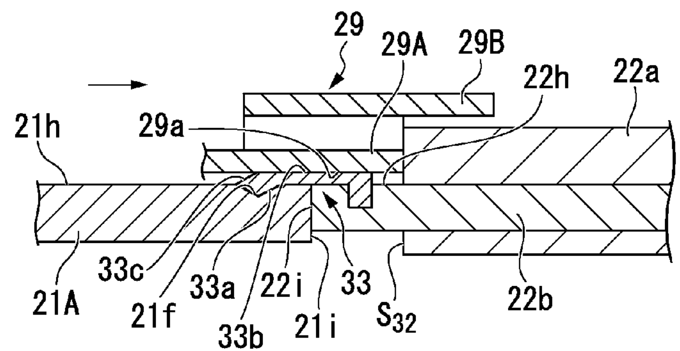
FIG. 16D is a schematic view for describing the engagement motion of the intermediate shaft section and the surgical instrument unit shaft section of the operation support device according to the second embodiment of the present invention.

In this process, as shown in FIG. 16D, the inner circumference pressing section 29A is moved toward the hook portion 33 in the axial direction. In the present embodiment, the outer circumferential ring section 29B of the attachment/detachment ring 29 is slid toward the shaft engagement fixing position in the axial direction. Accordingly, the inner circumference pressing section 29A connected to the outer circumferential ring section 29B is moved.

Here, even when the hook portion 33 is in the engagement state to be raised from the outer circumferential side surface 21*h* in the previous process, as the distal end portion of the inner circumference pressing section 29A abuts the taper 33*c*, a force of pressing down the hook portion 33 toward the outer circumferential side surface 21*h* is applied. For this reason, the hook portion 33 can be pressed toward the outer circumferential side surface 21*h*, and the entire engaging protrusion 33*a* is fitted into the engaging concave section 21*f*.

As described above, when the inner circumference pressing section 29A rides on the outer circumferential surface 33*b* of the hook portion 33, the hook portion 33 is sandwiched between the outer circumferential side surfaces 21*h* and 22*h* and the position restricting surface 29*a* to be pressed in the radial direction from the outside. As a result, the engaging protrusion 33*a* is prevented from being spaced and disengaged from the engaging concave section 21*f*. That is, the shaft engagement state is maintained and the shaft engagement fixing state is formed.

As described above, the shaft engagement fixing process is finished.

In addition, the fact that the hook portion 33 is pressed by the position restricting surface 29*a* means that position restriction in the radial direction is performed within a range in which the hook portion 33 is moved in the radial direction not to release the engagement. For this reason, there is no need to maintain constant contact between the position restricting surface 29*a* and the outer circumferential surface 33*b*.

In this way, the intermediate shaft 22*b* and the driving force transmission member 21*b* are engaged and integrated with each other via the hook portion 33. In the present embodiment, since a distance between the position restricting surface 29*a* and the outer circumferential side surface 21*h* is $H_1$, the hook portion 33 can be slidingly moved with respect to the position restricting surface 29*a* in the axial direction.

For this reason, when the driving force is transmitted from the surgical instrument driving unit 23 to the intermediate shaft 22*b*, as shown in FIGS. 17A and 17B, the hook portion 33 and the input side transmission shaft section 21A engaged with the hook portion 33 advance and retract in the axial direction with the intermediate shaft 22*b*. The position restricting surface 29*a* functions as a moving guide of the driving force transmission member 21*b* and the intermediate shaft 22*b* via the hook portion 33.

Since a gap between the position restricting surface 29*a* and the outer circumferential side surfaces 21*h* and 22*h* is a certain vale of $H_1$, the engaging protrusion 33*a* is not spaced apart from the engaging concave section 21*f* in the radial direction during movement. For this reason, even when a force of spacing the driving force transmission member 21*b* and the surgical instrument unit support 21*a* from each other in the axial direction is applied, a shaft engagement state between the driving force transmission member 21*b* and the intermediate member support 22*a* is maintained.

A length of the position restricting surface 29*a* in the axial direction is set more than a length in which an allowable moving amount of the input side transmission shaft section 21A in use of the surgical instrument unit 21 and a length of the hook portion 33 are added. For this reason, the shaft engagement fixing state can be formed in the entire moving range in which the hook portion 33 is moved.

To release the above-mentioned shaft engagement fixing state, the shaft engagement fixing release process and the shaft disengagement process may be performed in sequence.

The shaft engagement fixing release process is a process of moving the shaft fixing member to a position of the shaft engagement fixing state and forming a shaft disengagement state in which compression against the connection engaging section is released.

The shaft disengagement process is a process of spacing the first support and the second support from each other in the moving direction of the first shaft section and the second shaft section and disengaging the first shaft section and the second shaft section from each other.

Specifically, the shaft engagement fixing process and the shaft engagement process, which are described above, may be performed in reverse sequence. For this reason, description thereof will be omitted.

The attachment/detachment motion of the support attachment/detachment mechanism unit 31B will be described, with the attachment/detachment method thereof.

In this method, upon mounting, a support engaging process and a support engagement fixing process are sequentially performed. Upon dismounting, a support engagement fixing release process and a support disengagement process are sequentially performed.

In addition, in the present embodiment, these processes are performed in parallel with the above-mentioned attachment/detachment motion of the shaft attachment/detachment mechanism unit 31A.

The attachment/detachment motion of the support attachment/detachment mechanism unit 31B is the same motion as in the case in which the engaging concave section 21*f*, the hook portion 33 and the inner circumference pressing section 29A are replaced with the engaging concave section 21*s*, the hook portion 36 and the inner circumference pressing section 29E in the attachment/detachment motion of the shaft attachment/detachment mechanism unit 31A.

The support engaging process is a process of causing the intermediate member support 22*a* and the surgical instrument unit support 21*a* to approach each other in the moving direction of the intermediate shaft 22*b* and the input side transmission shaft section 21A and engaging the engaging concave section 21*s* and the engaging protrusion 36*a*.

Figure 18A:
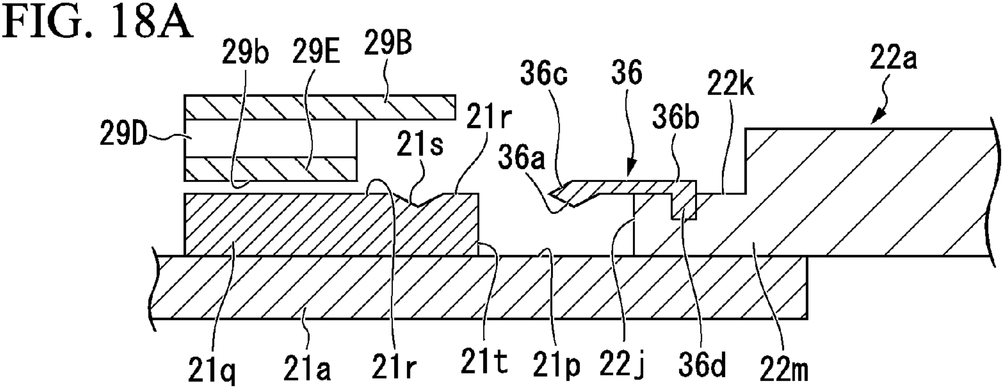
FIG. 18A is a schematic view for describing an engagement motion of an intermediate member support and a surgical instrument unit support of the operation support device according to the second embodiment of the present invention.

As shown in FIG. 18A, in accordance with relative movement of the surgical instrument unit support 21*a* and the intermediate member support 22*a* by the mounting motion of the shaft attachment/detachment mechanism unit 31A, the distal end surface 21*t* of each of the step-shaped sections 21*q* and the proximal end surface 22*j* of each of the insertion sections 22*m* approach each other in a state in which the distal end surface 21*t* and the proximal end surface 22*j* face each other.

Here, the inner circumference pressing section 29E is moved with the surgical instrument unit support 21*a* in a state in which the inner circumference pressing section 29E is disposed at the proximal end side similar to the inner circumference pressing section 29A disposed at the released position. For this reason, an upper section of the engaging concave section 21*s* is opened.

Figure 18B:
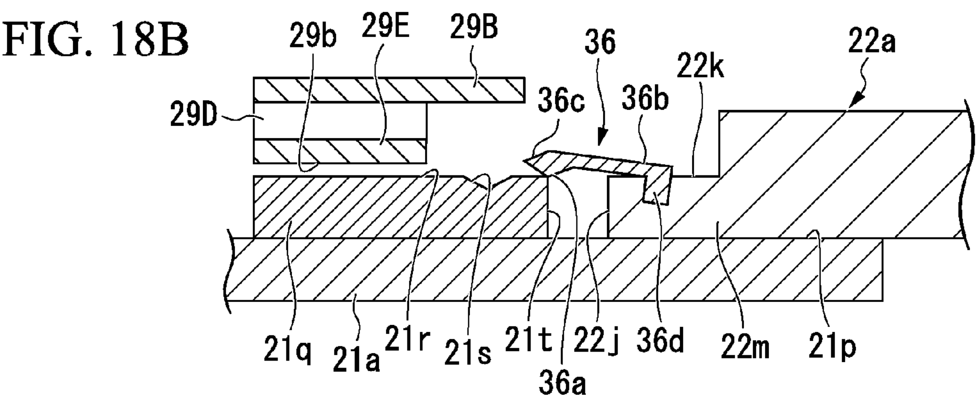
FIG. 18B is a schematic view for describing the engagement motion of the intermediate member support and the surgical instrument unit support of the operation support device according to the second embodiment of the present invention.

As shown in FIG. 18B, when a distance between the distal end surface 21*t* and the proximal end surface 22*j* is reduced, the distal end portion of the step-shaped section 21*q* abuts the engaging protrusion 36*a* of the hook portion 36 to rotate the hook portion 36.

Further, when a distance between the distal end surface 21*t* and the proximal end surface 22*j* is reduced, the engaging protrusion 36*a* rides on the upper surface 21*r* and moves forward.

Figure 18C:
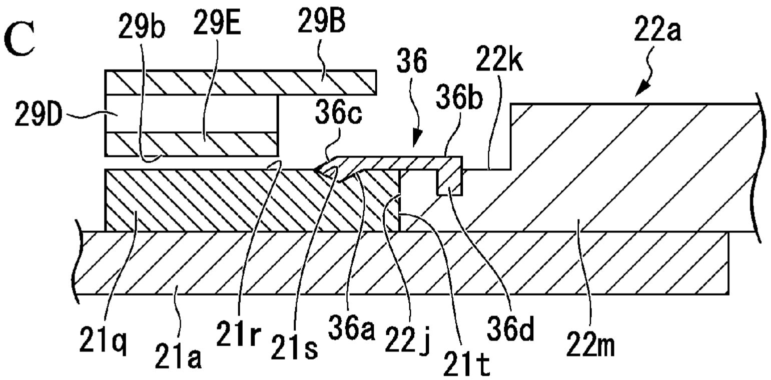
FIG. 18C is a schematic view for describing the engagement motion of the intermediate member support and the surgical instrument unit support of the operation support device according to the second embodiment of the present invention.

As shown in FIG. 18C, when the engaging protrusion 36*a* is disposed on the engaging concave section 21*s*, the engaging protrusion 36*a* enters the inside of the engaging concave section 21*s*. Then, the engaging protrusion 36*a* is engaged with the engaging concave section 21*s*.

As described above, the support engaging process is finished.

In addition, in this process, the same engagement state as the engagement state in the shaft engagement process is obtained. Further, when the hinge portion 36*d* is configured to bias the hook portion 36 against the outer circumferential side surface 22*k*, in this process, the engaging protrusion 36*a* preferably more securely enters the inside of the engaging concave section 21*s* to obtain a good engagement state.

Next, a support engagement fixing process is performed. This process is a process of moving the inner circumference pressing section 29E, which is a support fixing member, to press the hook portion 36, and forming a support engagement fixing state in which an engagement state with the engaging concave section 21*s* is maintained.

Figure 18D:
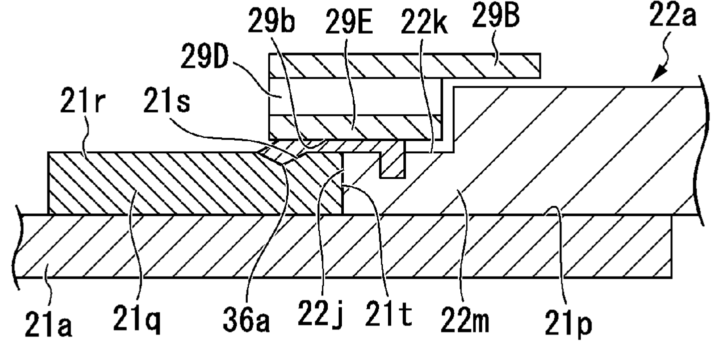
FIG. 18D is a schematic view for describing the engagement motion of the intermediate member support and the surgical instrument unit support of the operation support device according to the second embodiment of the present invention.

In this process, as shown in FIG. 18D, the inner circumference pressing section 29E is moved toward the hook portion 36 in the axial direction. However, in the present embodiment, since the inner circumference pressing section 29E is connected to the outer circumferential ring section 29B, the shaft engagement fixing process is started and this process is also performed.

In this process, even when the engagement state of the previous process is an imperfect engagement state and the hook portion 36 is in the engagement state to be raised from the outer circumferential side surface 22*k*, as the distal end portion of the inner circumference pressing section 29E abuts the taper 36*c*, a force of pressing down the hook portion 36 toward a side of the outer circumferential side surface 22*k* is applied. For this reason, the hook portion 36 is pressed toward the outer circumferential side surface 22*k*, and the entire engaging protrusion 36*a* is fitted into the engaging concave section 21*s*.

As described above, when the inner circumference pressing section 29E rides on the outer circumferential surface 36*b* of the hook portion 36, the hook portion 36 is sandwiched between the upper surface 21*r* and the outer circumferential side surface 22*k* and the position restricting surface 29*b* to be pressed in the radial direction from the outside. As a result, the engaging protrusion 36*a* can be prevented from being spaced and disengaged from the engaging concave section 21*s*. That is, the support engagement state is maintained, and the support engagement fixing state is formed.

As described above, the support engagement fixing process is finished.

In this way, the intermediate member support 22*a* and the surgical instrument unit support 21*a* are engaged and integrated with each other via the hook portion 36.

To release the support engagement fixing state, the support engagement fixing release process and the support disengagement process may be performed in sequence.

The support engagement fixing release process is a process of moving the support fixing member from a position of the support engagement fixing state and forming a support disengagement state in which compression against the support connection engaging section is released.

The support disengagement process is a process of spacing the first support and the second support from each other in the moving direction of the first shaft section and the second shaft section and disconnecting the first support and the second support.

Specifically, the support engagement fixing process and the support engaging process, which are described above, may be performed in reverse sequence. For this reason, description thereof will be omitted.

Next, the entire attachment/detachment motion will be described focusing on an action in which the respective processes are performed in parallel.

However, in the following description, a case in which a pair of shaft attachment/detachment mechanism units 31A and a pair of support attachment/detachment mechanism units 31B are installed on the same cross-section will be described so that the entire attachment/detachment motion can be readily understood. Here, since the description of the specific configuration makes the drawings complicated, the support attachment/detachment mechanism unit 31B will be described using the drawing related to a modified example (a second modified example).

Figure 19:
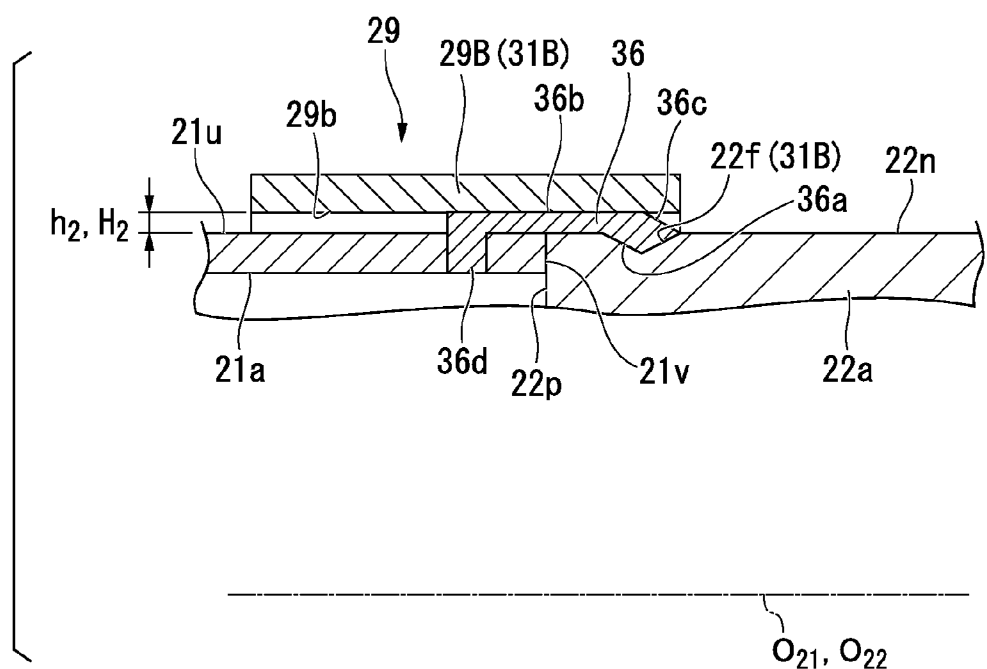
FIG. 19 is a schematic cross-sectional view showing a modified example (a second modified example) of main parts of a support attachment/detachment mechanism unit of the operation support device according to the second embodiment of the present invention.
Figure 20A:
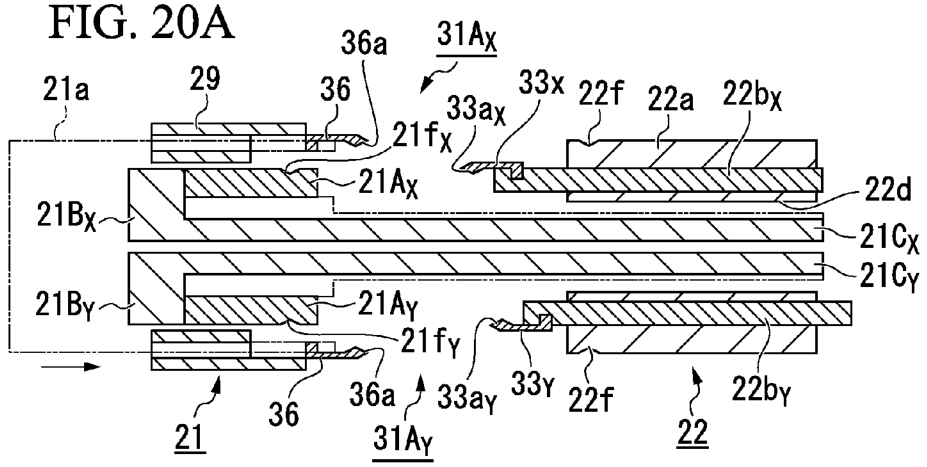
FIG. 20A is a schematic view for describing a mounting motion of the surgical instrument unit with respect to the intermediate member of the operation support device according to the second embodiment of the present invention.
Figure 20B:
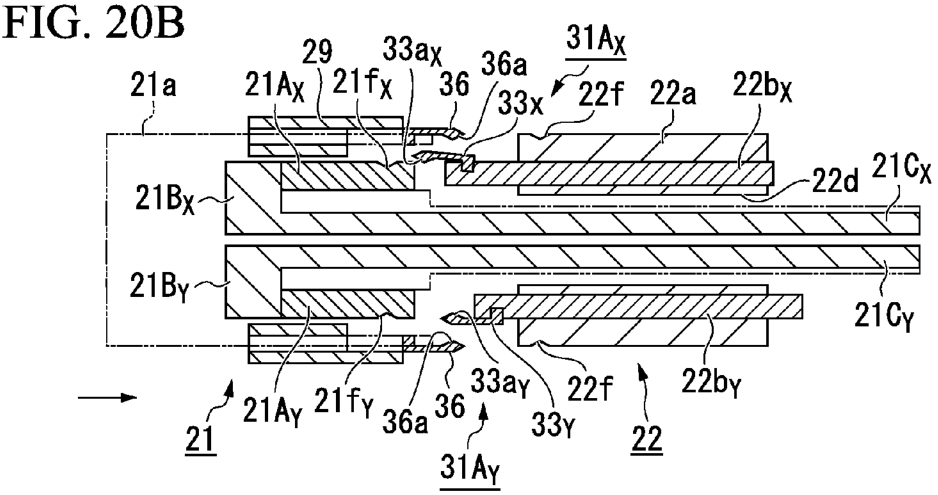
FIG. 20B is a schematic view for describing the mounting motion of the surgical instrument unit with respect to the intermediate member of the operation support device according to the second embodiment of the present invention.
Figure 20C:
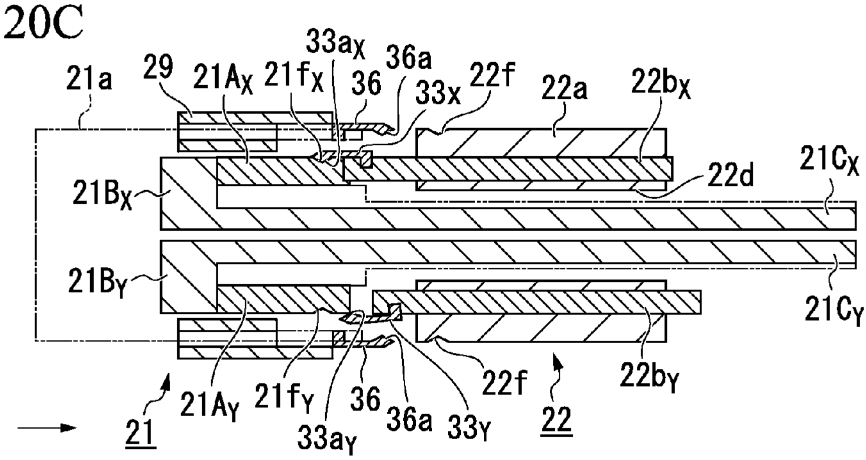
FIG. 20C is a schematic view for describing the mounting motion of the surgical instrument unit with respect to the intermediate member of the operation support device according to the second embodiment of the present invention.
Figure 21A:
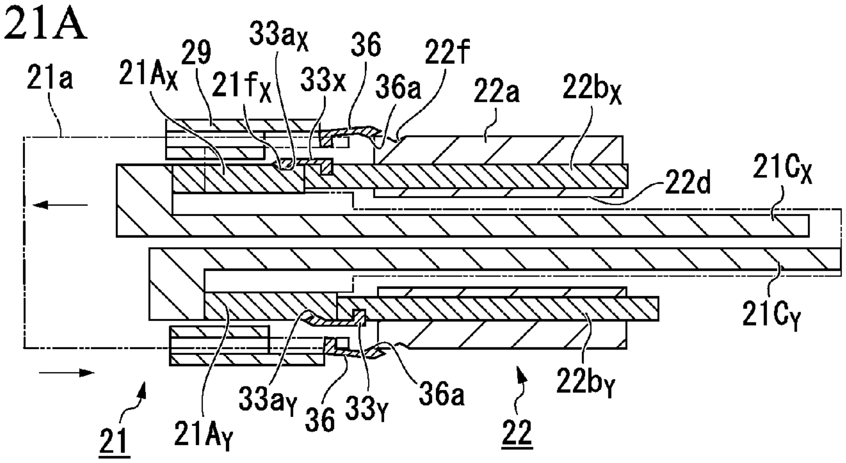
FIG. 21A is a view for describing a motion continued from FIGS. 20A, 20B and 20C.
Figure 21B:
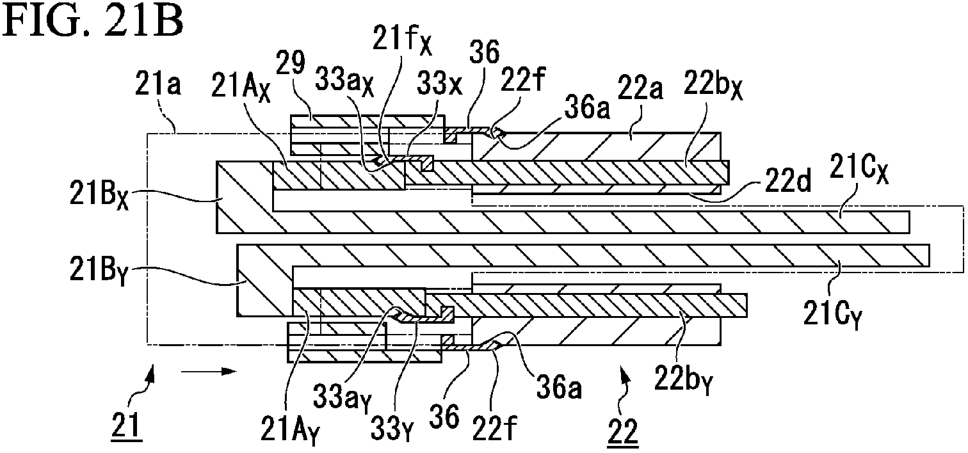
FIG. 21B is a view for describing the motion continued from FIGS. 20A, 20B and 20C.
Figure 21C:
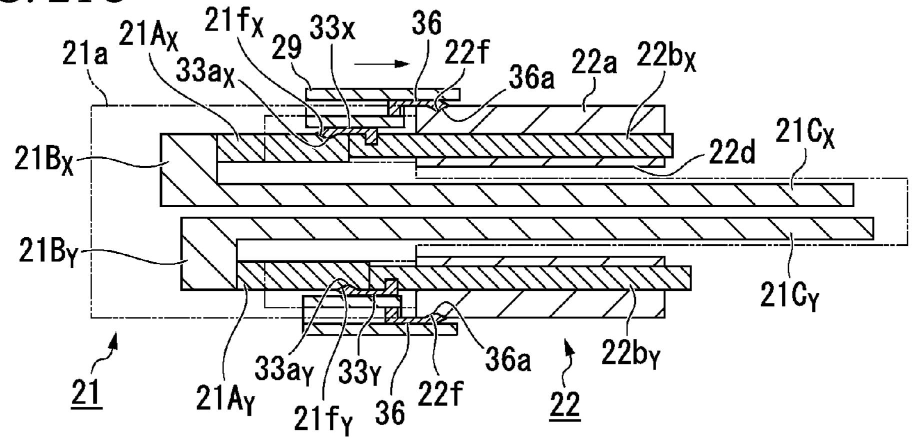
FIG. 21C is a view for describing the motion continued from FIGS. 20A, 20B and 20C.

FIG. 19 is a schematic cross-sectional view showing a modified example (a second modified example) of main parts of a support attachment/detachment mechanism unit of the operation support device according to the second embodiment of the present invention. FIGS. 20A, 20B and 20C are schematic views for describing a connecting motion of a surgical instrument unit with respect to an intermediate member of the operation support device according to the second embodiment of the present invention. FIGS. 21A, 21B and 21C are views for describing a motion continued from FIG. 20C. FIGS. 22A, 22B, 22C and 22D are schematic views for describing an engagement motion of a shaft fixing member and a second shaft engaging section of the operation support device according to the second embodiment of the present invention.

First, a configuration according to the modified example (the second modified example) of the support attachment/detachment mechanism unit 31B will be described in brief.

In the present modified example, as shown in FIG. 19, the hook portion 36 is formed at the outer circumferential section of the surgical instrument unit support 21*a*. In addition, an engaging concave section 22*f* configured to engage the engaging protrusion 36*a* is formed at an outer circumferential side surface 22*n* of the intermediate shaft 22*b* in the outer circumferential section of the intermediate member support 22*a*. In addition, the position restricting surface 29*b* is formed at a rear surface side of the outer circumferential ring section 29B. The position restricting surface 29*b* is formed at a position of a height $H_2$ from an outer circumferential surface 21*u* of the surgical instrument unit support 21*a* at which the hook portion 36 is installed.

The surgical instrument unit support 21*a* and the intermediate member support 22*a* abut a distal end surface 21*v* of the surgical instrument unit support 21*a* and a proximal end surface 22*p* of the intermediate member support 22*a* in the engagement state.

In the present modified example, in the support engaging process, as the surgical instrument unit support 21*a* and the intermediate member support 22*a* are relatively moved in the axial direction to cause the distal end surface 21*v* and the proximal end surface 22*p* to approach each other, the engaging protrusion 36*a* of the hook portion 36 rides on the intermediate member support 22*a* to be engaged with the engaging concave section 22*f*.

In the support engagement fixing process, as the outer circumferential ring section 29B is moved to the distal end side, the hook portion 36 is pressed toward a side of the outer circumferential surface 21*u* and sandwiched between the position restricting surface 29*b* and the outer circumferential surface 21*u* to form a support engagement fixing state.

As described above, even when the support connecting member is installed at the second support and the support engaging section is installed at the first support, similar to the first embodiment, the supports can be moved in the axial direction to move the support fixing member in the axial direction, performing engagement of the supports.

In the present embodiment and the present modified example, the support attachment/detachment mechanism unit 31B is installed at the intermediate member support 22*a* and the surgical instrument unit support 21*a*. In addition, since the attachment/detachment ring 29 used in the support attachment/detachment mechanism unit 31B is one, even when a plurality of support attachment/detachment mechanism units 31B having the same configuration are provided, the motions of the support attachment/detachment mechanism units 31B are the same.

On the other hand, when the plurality of shaft attachment/detachment mechanism units 31A are provided, stopping places in the axial direction of the driving force transmission shafts 23*b* in accordance with a stopping situation of the surgical instrument driving unit 23 upon attachment/detachment may differ. For example, as shown in FIG. 20A, two systems of shaft attachment/detachment mechanism units 31$A_X$ and 31$A_Y$ are considered. Hereinafter, in order to separately describe motions of the two systems of shaft attachment/detachment mechanism units 31$A_X$ and 31$A_Y$, subscripts X and Y are added to reference numerals of the respective members.

For example, an intermediate shaft 22$b_X$ belonging to the shaft attachment/detachment mechanism unit 31$A_X$ may protrude toward and stop at the proximal end side rather than an intermediate shaft 22$b_Y$ belonging to the shaft attachment/detachment mechanism unit 31$A_Y$.

In this case, according to the conventional art, since engagement positions in the axial direction of the intermediate shafts 22$b_X$ and 22$b_Y$ are different, an operation of coinciding protrusion amounts of the intermediate shafts 22$b_X$ and 22$b_Y$ (initialization of positioning for attachment/detachment) is needed. When the positioning initialization is not performed, an operation of aligning and engaging the positions of the input side transmission shaft sections 21$A_X$ and 21$A_Y$ to/with the protrusion positions of the intermediate shafts 22$b_X$ and 22$b_Y$ is needed. In any case, the attachment/detachment operation is complicated.

In the present embodiment, since the attachment/detachment motion is performed as will be described below, the attachment/detachment can be easily performed even in this case.

In addition, in connection of the surgical instrument unit 21 and the intermediate member 22, any one may be moved. Hereinafter, a case in which the intermediate member 22 is fixed and the surgical instrument unit 21 is inserted will be described.

When the surgical instrument unit 21 is inserted into the surgical instrument unit insertion hole 22*d* and approaches the intermediate member 22 in the axial direction, as shown in FIG. 20B, a hook portion 33$_X$ abuts a distal end of the input side transmission shaft section 21$A_X$ (corresponding to a state of FIG. 16B). Here, a hook portion 33$_Y$ is spaced apart from the input side transmission shaft section 21$A_Y$ (corresponding to a state of FIG. 16A).

Here, as shown in FIG. 14 (not shown in FIG. 20A), engaging protrusion 29$c_X$ and 29$c_Y$ of rod-shaped portions 29$C_X$ and 29$C_Y$ are engaged with engaging concave sections 21$j_X$ and 21$j_Y$ of connecting sections 21$B_X$ and 21$B_Y$.

When the surgical instrument unit 21 is further inserted into the surgical instrument unit insertion hole 22*d*, as shown in FIG. 20C, an engaging protrusion 33$a_X$ is engaged with an engaging concave section 21$f_X$ (corresponding to a state of FIG. 16C). In addition, the hook portion 33$_Y$ abuts the distal end of the input side transmission shaft section 21$A_Y$ (corresponding to a state of FIG. 16B).

Here, the hook portion 36 does not abut the intermediate member support 22*a*. For this reason, the support engagement state is still not formed. For this reason, the surgical instrument unit support 21*a* and the intermediate member support 22*a* can further approach each other. However, the input side transmission shaft section 21$A_X$ abuts the intermediate shaft 22$b_X$ in the axial direction. For this reason, while not specifically shown, engagement between the connecting section 21$B_X$ and the engaging protrusion 29$c_X$ is deviated, and movement of the connecting section 21$B_X$ and the input side transmission shaft section 21$A_X$ is stopped.

Meanwhile, since engagement of the connecting section 21$B_Y$ and the engaging protrusion 29$c_Y$ is not deviated, the connecting section 21$B_Y$ and the input side transmission shaft section 21$A_Y$ further move toward the distal end side, and as shown in FIG. 21A, the engaging protrusion 33$a_Y$ is engaged with the engaging concave section 21$f_Y$ (corresponding to a state of FIG. 16C).

When the surgical instrument unit 21 is further inserted into the surgical instrument unit insertion hole 22*d*, as shown in FIG. 21B, the input side transmission shaft section 21$A_Y$ also abuts the intermediate shaft 22$b_Y$. For this reason, while not specifically shown, engagement of the connecting section 21$B_Y$ and the engaging protrusion 29$c_Y$ is deviated, and movement of the connecting section 21$B_Y$ and the input side transmission shaft section 21$A_Y$ is stopped.

In this way, until the surgical instrument unit support 21*a* is brought in contact with the intermediate member support 22*a* not to move, the surgical instrument unit 21 is inserted into the surgical instrument unit insertion hole 22*d*. Here, after the hook portion 36 abuts the end portion of the intermediate member support 22*a* (see FIG. 21A) and rides thereon, as shown in FIG. 21B, each of the engaging protrusions 36*a* is engaged with each of the engaging concave sections 22*f*.

As described above, the shaft engagement process and the support engaging process are finished.

Next, the attachment/detachment ring 29 is slid to a shaft engagement fixing position of the distal end side of the surgical instrument unit support 21*a* in the axial direction, and as shown in FIG. 21C, the shaft engagement fixing process and the support engagement fixing process are performed in parallel.

In the present embodiment, the attachment/detachment ring 29 is installed at the outer circumferential section of the surgical instrument unit support 21*a*. For this reason, an operator may slide the attachment/detachment ring 29 in the same direction as the moving direction of the surgical instrument unit 21 while holding the surgical instrument unit 21 in his or her hands. For this reason, the motion can be extremely easily and rapidly performed.

In addition, manipulation of the attachment/detachment ring 29 can be continuously performed from the inserting motion of the surgical instrument unit 21 into the intermediate member 22. For this reason, the mounting motion can be performed by motion in one step. For example, from the beginning, when the surgical instrument unit 21 is inserted with holding the attachment/detachment ring 29, the surgical instrument unit 21 is brought in contact with the intermediate member 22 in the axial direction, and automatically, only the attachment/detachment ring 29 is moved in the axial direction. For this reason, there is no need for motion in two steps in which another hand is added to exchange the surgical instrument unit 21 or move the attachment/detachment ring 29.

As described above, the second connecting process is finished.

In addition, if the above-mentioned motion is reversely performed, the shaft engagement fixing release process, the support fixing release process, the shaft disengagement process, and the support disengagement process can be performed.

While the motion will be easily understood from the description, only the motion of the shaft attachment/detachment mechanism unit 31A will be simply described.

Figure 22A:
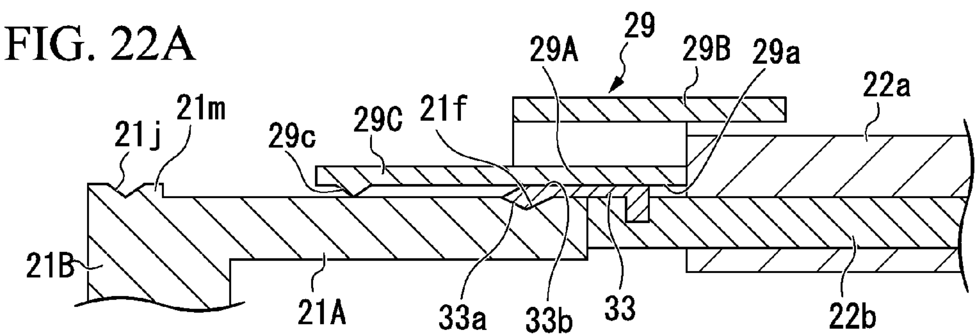
FIG. 22A is a schematic view for describing a dismounting motion of the surgical instrument unit with respect to the intermediate member of the operation support device according to the second embodiment of the present invention.
Figure 22B:
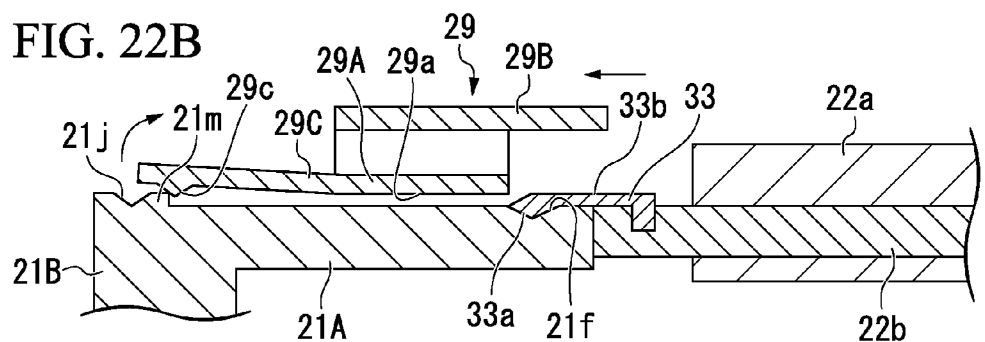
FIG. 22B is a schematic view for describing the dismounting motion of the surgical instrument unit with respect to the intermediate member of the operation support device according to the second embodiment of the present invention.
Figure 22C:
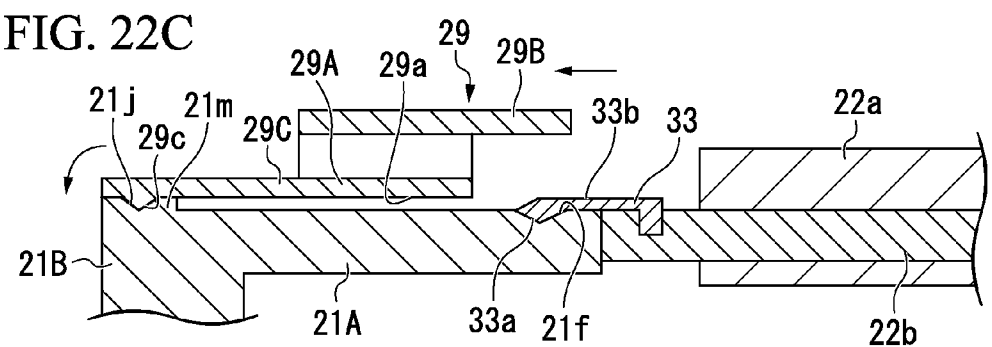
FIG. 22C is a schematic view for describing the dismounting motion of the surgical instrument unit with respect to the intermediate member of the operation support device according to the second embodiment of the present invention.

In order to perform the shaft engagement fixing release from the shaft engagement fixing state shown in FIG. 22A, the attachment/detachment ring 29 is slid to the proximal end side while holding the outer circumferential ring section 29B (see FIG. 22B).

Here, when the inner circumference pressing section 29A is moved to the proximal end side rather than the hook portion 33, compression against the hook portion 33 is removed. For this reason, the hook portion 33 can be pivoted, and the shaft engagement fixing state is released.

Further, when the attachment/detachment ring 29 is moved to the proximal end side, as shown in FIG. 22B, the engaging protrusion 29*c* abuts the step-shaped protrusion section 21*m*. Then, the rod-shaped portion 29C is bent, and the engaging protrusion 29*c* rides on the step-shaped protrusion section 21*m*. Here, the connecting section 21B is pressed to the proximal end side. However, because the engagement state of the hook portion 33 and the engaging concave section 21*f* is not released, the connecting section 21B and the input side transmission shaft section 21A do not move.

When the engaging protrusion 29*c* is disposed on the engaging concave section 21*j*, the engaging protrusion 29*c* is engaged with the engaging concave section 21*j*. Here, the engaging protrusion 29*c* is securely fitted into the engaging concave section 21*f* to be biased inside in the radial direction by an elastic recovering force of the rod-shaped portion 29C.

For this reason, the attachment/detachment ring 29 and the connecting section 21B are integrated, and manipulation for moving the attachment/detachment ring 29 to the proximal end side is securely transmitted to the connecting section 21B. For this reason, the connecting section 21B and the input side transmission shaft section 21A begin to move to the proximal end side.

Figure 22D:
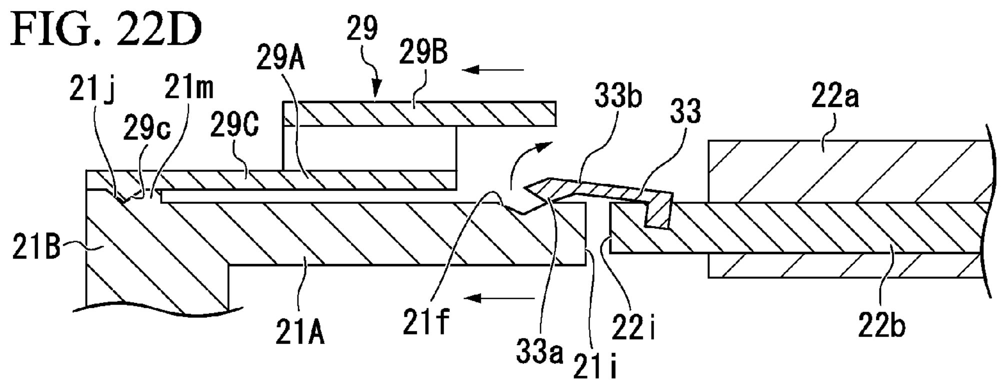
FIG. 22D is a schematic view for describing the dismounting motion of the surgical instrument unit with respect to the intermediate member of the operation support device according to the second embodiment of the present invention.

Here, as shown in FIG. 22D, since the hook portion 33 is in a turnable state, the input side transmission shaft section 21A begins to move to turn clockwise as shown, and engagement with the engaging concave section 21*f* is released. Accordingly, the input side transmission shaft section 21A is separated from the intermediate shaft 22*b*, and the distal end surface 21*i* and the proximal end surface 22*i* are spaced apart from each other.

In this way, the shaft engagement state is released, and the shaft disengagement process is finished.

When the attachment/detachment ring 29 is moved to the released position, the attachment/detachment ring 29 is moved with the surgical instrument unit support 21*a*. For this reason, when the attachment/detachment ring 29 is held and moved to the proximal end side, the surgical instrument unit 21 is also automatically moved to the proximal end side to be extracted from the intermediate member 22.

As described above, the dismounting is finished.

In this way, in the dismounting motion according to the present embodiment, an external force for moving the connecting section 21B to the proximal end side is hardly transmitted to the intermediate shaft 22*b*. For this reason, the shaft engagement state can be released with almost no resistance.

As described above, in the operation support device 120 according to the present embodiment, the first support and the second support can move in the moving direction of the first shaft section and the second shaft section to perform engagement or disengagement of the first shaft section and the second shaft section. In addition, as the shaft fixing member is moved, the attachment/detachment can be performed by a simple manipulation in which the shaft engagement fixing state and the shaft disengagement state are selectively formed. For this reason, the attachment/detachment of the surgical instrument unit with respect to the surgical instrument driving unit can be easily and rapidly performed.

Further, connection in the second connecting process and exchange of the surgical instrument unit 21 after the connection can be easily and rapidly performed.

In addition, in the present embodiment, the attachment/detachment motion can be performed by only movement in the axial direction. For this reason, upon mounting, the surgical instrument unit 21 is inserted into the intermediate member 22 to complete the attachment/detachment. That is, the mounting can be performed by one touch.

Further, upon attachment/detachment, even though protrusion positions of the intermediate shafts 22*b* are different, when the attachment/detachment motion is performed, in accordance with a position of each of the intermediate shafts 22*b*, since a position of each of the input side transmission shaft sections 21A follows that of the intermediate shaft 22*b*, the attachment/detachment can be performed regardless of the position of the intermediate shaft 22*b*.

In addition, even upon mounting or upon dismounting (upon separation), the attachment/detachment ring 29 may be manipulated in the same direction as the attachment/detachment direction with holding the outer circumferential surface of the surgical instrument unit 21 including the attachment/detachment ring 29. For this reason, the attachment/detachment manipulation can be intuitively performed, and the attachment/detachment manipulation can be easily performed.

For this reason, in particular, when the surgical instrument unit 21 is emergently separated, sure attachment/detachment can be performed.

In addition, in the present embodiment, the surgical instrument driving unit 23 is spaced apart from the surgical instrument unit 21 via the intermediate member 22 and the drape 7. For this reason, an assembly task of the surgical instrument unit 21 and the intermediate member 22 can be performed only in the clean area $A_C$. For this reason, exchange of the surgical instrument unit 21 during the operation can be rapidly and easily performed.

Further, in the present embodiment, the surgical instrument unit 21 is inserted into and connected to the intermediate member 22. For this reason, for example, the surgical instrument unit 21 can be attached and detached toward the connecting body of the intermediate member 22 and the surgical instrument driving unit 23, disposed over the patient and supported by an arm, or the like, from an upper side. For this reason, the attachment/detachment task can be efficiently performed.

Third Modified Example

Next, a third modified example of the present embodiment will be described.

Figure 23:
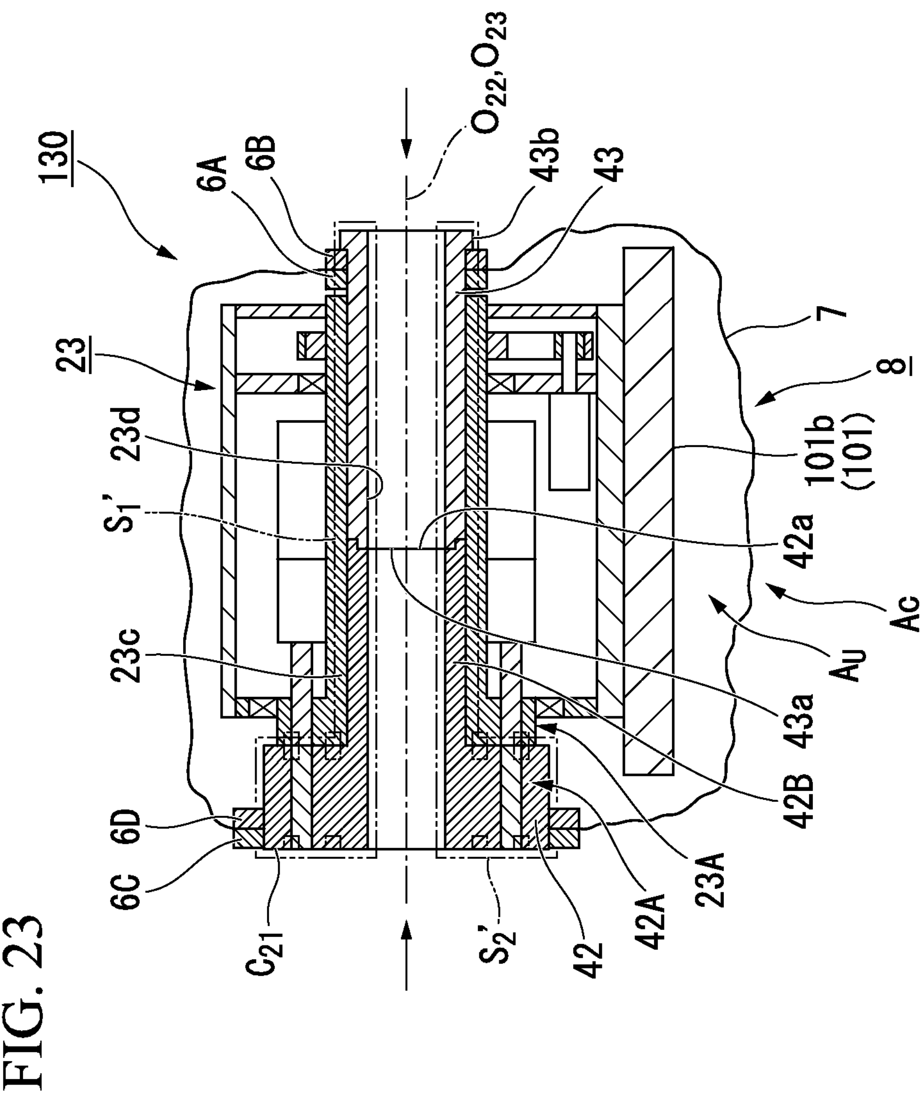
FIG. 23 is a schematic cross-sectional view showing a configuration of main parts of an operation support device according to a modified example (a third modified example) of the second embodiment of the present invention in the axial direction.

FIG. 23 is a schematic cross-sectional view showing a configuration of an operation support device according to a present modified example (a third modified example) of the second embodiment of the present invention in the axial direction.

As shown in FIG. 23, an operation support device 130 of the present modified example includes intermediate members 42 and 43, instead of the intermediate member 22 of the operation support device 120 according to the second embodiment. Hereinafter, the present modified example will be described focusing on differences from the second embodiment.

The intermediate member 42 includes a connecting section 42A and a tubular section 42B.

The connecting section 42A moves a connecting section of the connecting section 22A and the drape rings 6C and 6D of the intermediate member 22 according to the second embodiment to the vicinity of the connection end portion $C_{21}$ of the proximal end side of the connecting section 22A.

The tubular section 42B is configured to reduce a length of the tubular section 22B of the intermediate member 22. A fitting section 42*a* to the intermediate member 43 is formed at the end portion of the distal end side of the tubular section 42B.

The intermediate member 43 includes a fitting section 43*a* formed at the proximal end side and fitted to the fitting section 42*a* of the intermediate member 42. The intermediate member 43 is a tubular member configuring a tubular assembly having substantially the same shape as the intermediate member 22 by fitting to the intermediate member 42. However, an annular protrusion section 43*b* protruding outward in the radial direction is formed at the distal end side of the intermediate member 43. Accordingly, when the tubular assembly is constituted by the intermediate member 43 and the intermediate member 42, the drape ring 6B can be locked from the distal end side.

The fitting sections 42*a* and 43*a* are detachably fitted to each other. When there is no obstacle to movement of the through-hole portion 23*d* and the surgical instrument unit 21 of the shaft rotating member 23A with respect to the tubular section 21*d* in the axial direction, an appropriate configuration can be used as the fitting sections 42*a* and 43*a*. In FIG. 23, as an example, the fitting section 43*a* is constituted by a cylindrical protrusion section extending from the inner circumferential portion in the axial direction, and the fitting section 42*a* is constituted by a hole section fitted onto the protrusion section of the fitting section 43*a* at the inner circumference side.

According to the operation support device 130, the intermediate members 42 and 43 are configured to divide a shape of the intermediate member 22 according to the second embodiment into two parts in the axial direction. For this reason, a shape of the intermediate members 42 and 43 upon assembly is substantially the same as that of the intermediate member 22. Accordingly, the present modified example has the same effects as the second embodiment.

In particular, in the present modified example, when the intermediate members 42 and 43 are assembled to the shaft rotating member 23A, as shown by an arrow of FIG. 23, the intermediate member 42 is inserted from the proximal end side of the shaft rotating member 23A, and the intermediate member 43 is inserted from the distal end side of the shaft rotating member 23A. For this reason, assembly of the intermediate members 42 and 43 can be performed in the shaft rotating member 23A, and assembly with respect to the shaft rotating member 23A can be performed.

In addition, in the present modified example, a connecting position of the drape rings 6C and 6D is moved to the proximal end side in comparison with the second embodiment. For this reason, as shown in FIG. 23, the first surface section $S_1'$ extends to the proximal end side rather than the first surface section $S_1$. However, the present modified example has the same effect as the second embodiment in that the unclean area $A_U$ and the clean area $A_C$ are partitioned by the drape assembly 8.

In the present modified example, the drape ring enables connection of the intermediate member at an appropriate position.

In addition, the present modified example is an example of a case in which the intermediate member is divided into two parts. However, the intermediate member may be divided into three or more parts.

Third Embodiment

Next, a third embodiment of the present invention will be described.

Figure 24:
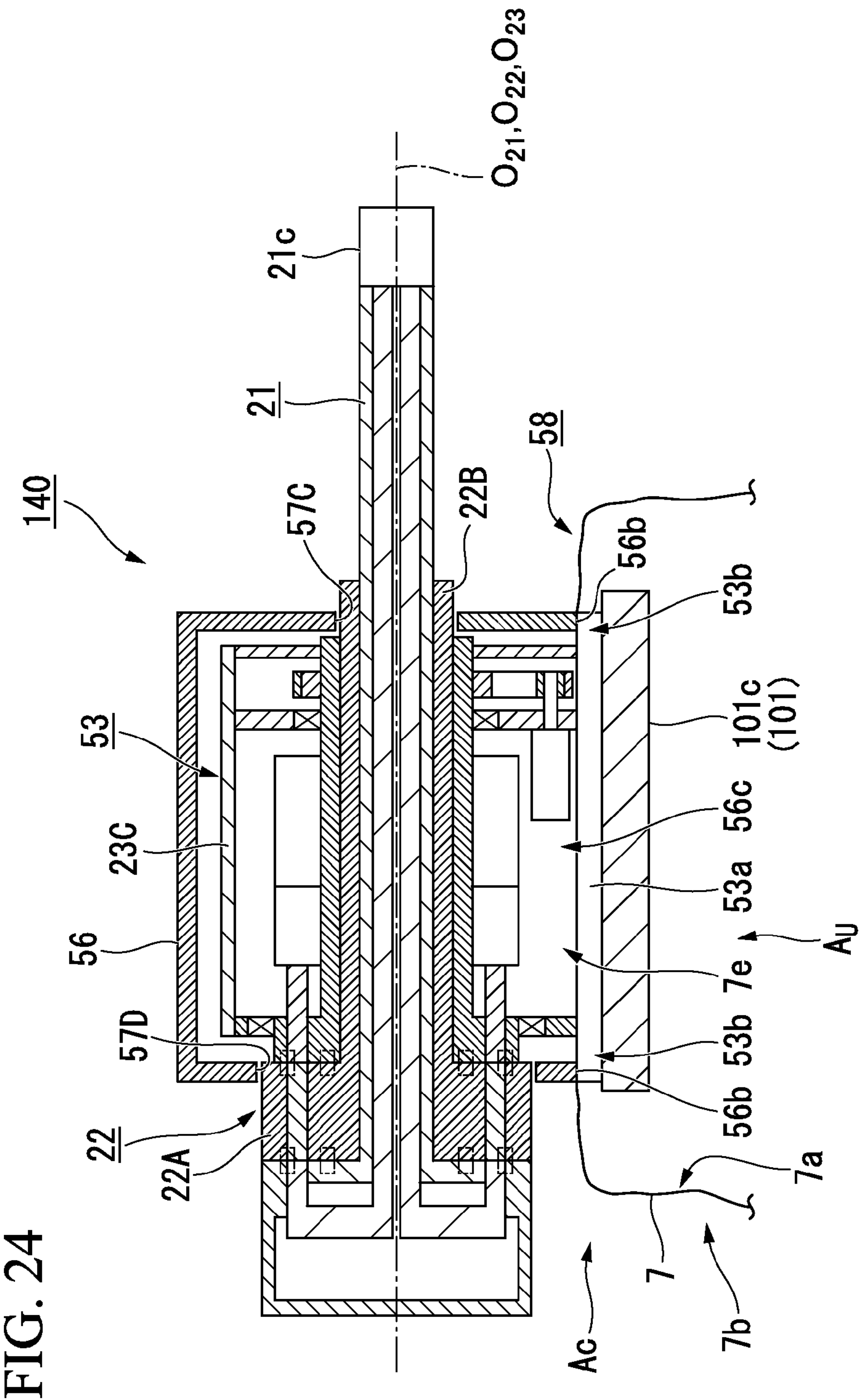
FIG. 24 is a schematic cross-sectional view showing a configuration of main parts of an operation support device according to a third embodiment of the present invention in an axial direction.
Figure 25A:
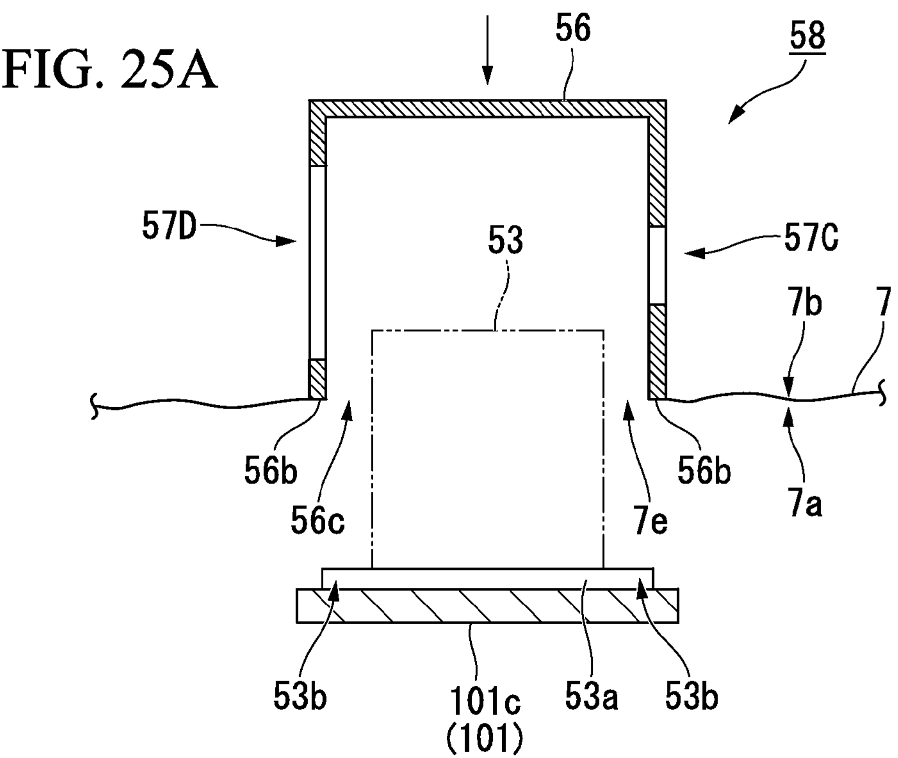
FIG. 25A is a schematic exploded view showing a relation between a coated housing and a drape used in an operation support device according to the third embodiment of the present invention and a modified example (a fourth modified example) thereof.

FIG. 24 is a schematic cross-sectional view showing a configuration of main parts of an operation support device according to the third embodiment of the present invention in an axial direction. FIG. 25A is a schematic exploded view showing a relation between a coated housing and a drape of the operation support device according to the third embodiment of the present invention.

As shown in FIG. 24, an operation support device 140 according to the present embodiment includes a surgical instrument driving unit 53 instead of the surgical instrument driving unit 23 of the operation support device 120 according to the second embodiment, and includes a drape assembly 58 (a shielding member) constituted by a sterilizable drive unit cover 56 and a drape 7 having a drape hole 7*e*, instead of the drape assembly 8. Hereinafter, the third embodiment will be described focusing on differences from the second embodiment.

The surgical instrument driving unit 53 is configured with a support plate 53*a* configured to support the housing 23C at a position joined with the linear driving moving section 101*c* in the surgical instrument driving unit 23 according to the second embodiment added thereto.

A drape attachment section 53*b* formed of a plate-shaped section extending outward from the entire circumference of the housing 23C rather than the housing 23C is formed at the support plate 53*a*.

In addition, while not specifically shown, an appropriate number of engaging sections, for example, snap fit, or the like, for fixing the drape hole 7*e* are formed at the drape attachment section 53*b*.

The drape assembly 58 includes the sterilizable drive unit cover 56 (a shielding member, a coated housing), instead of the drape rings 6A, 6B, 6C and 6D according to the second embodiment.

The drive unit cover 56 has an opening 56*c* formed at a position opposite to the drape attachment section 53*b* of the support plate 53*a*. The drive unit cover 56 is a box-shaped member surrounding the surgical instrument driving unit 53.

An opening end surface 56*b* in contact with the entire circumference of the drape attachment section 53*b* and the opening 56*c* is formed at the opening 56*c* of the drive unit cover 56.

In addition, while not specifically shown, an engaging section such as a snap fit, or the like engaged with the engaging section of the drape attachment section 53*b* is formed in the vicinity of the opening 56*c*.

Further, hole portions 57C and 57D that can pass through both end portions of the connecting section 22A and the tubular section 22B of the intermediate member 22 when the intermediate member 22 is connected to the surgical instrument driving unit 53 of the support plate 53*a* is formed at the side surface portion opposite to the drive unit cover 56.

A circular hole or the like that does not cause difficulty in rotation of the intermediate member 22 can be used as the hole portions 57C and 57D. In the present embodiment, as an example, the hole portions 57C and 57D may be formed to have a size of an inner diameter about 1 mm larger than the outer diameter of the tubular section 22B. Accordingly, the hole portions 57C and 57D are formed not to contact the tubular section 22B. However, a gap between the hole portions 57C and 57D and the tubular section 22B may be a small gap such that a finger or the like is not inserted.

In the present embodiment, a drape hole 7*e* having a size that can be joined with the opening end surface 56*b* of the drive unit cover 56 is formed in the drape 7.

Then, as shown in FIG. 25A, the drape assembly 58 is formed by joining an edge of the surface 7*b* of the drape hole 7*e* with the opening end surface 56*b*. As a joining method, for example, adhesion, fusion, or the like may be used.

In addition, the sterilization treatment is performed on the drape 7 and the drive unit cover 56.

Further, the drape assembly 58 may be formed by joining an end portion of the drape hole 7*e* with a frame member such as the drape ring according to the first and second embodiments and engaging the frame member, with which the drape 7 is joined, with the opening end surface 56*b* of the drive unit cover 56. As an engagement method, for example, a snap fit, a magnet, or the like may be used.

The operation support device 140 having the above-mentioned configuration may be assembled in substantially the same manner as in the second embodiment.

A driving force supply unit installation process, a shielding member disposition process, a first connecting process, and a second connecting process are sequentially performed. Hereinafter, the third embodiment will be described focusing on differences from the second embodiment.

The present embodiment is similar to the second embodiment, except for the blocking member disposition process.

As shown in FIG. 25A, in the shielding member disposition process according to the present embodiment, the drape assembly 58 is covered on the surgical instrument driving unit 53. Then, in the drape attachment section 53*b*, the drape assembly 58 is engaged with the surgical instrument driving unit 53. Accordingly, the hole portions 57C and 57D are disposed at a position coaxial with the central axis $O_{23}$ of the shaft rotating member 23A.

Accordingly, the surgical instrument driving unit 53 is surrounded by the drive unit cover 56, and the surgical instrument unit support section 101 is covered by the surface 7*a* of the drape 7.

Next, in the first connecting process according to the present embodiment, the intermediate member 22 is inserted into the hole portions 57C and 57D to be connected to the surgical instrument driving unit 53, similar to the second embodiment.

In addition, the second connecting process according to the present embodiment is the same process as in the second embodiment.

According to the present embodiment, the hole portions 57C and 57D are formed in the drive unit cover 56. For this reason, alignment of the shielding member disposition process can be easily performed, and close inserting of the intermediate member 22 can be easily performed.

In addition, the surgical instrument driving unit 53 is not covered by the drape 7, and the intermediate member 22 or surgical instrument unit 1 does not pass through the drape 7. For this reason, even when the intermediate member 22 or the surgical instrument unit 21 is rotated about the central axis $O_{23}$, the drape 7 is not rotated with the intermediate member 22 or the surgical instrument unit 21.

Fourth Modified Example

Next, a modified example (a fourth modified example) of the present embodiment will be described.

Figure 25B:
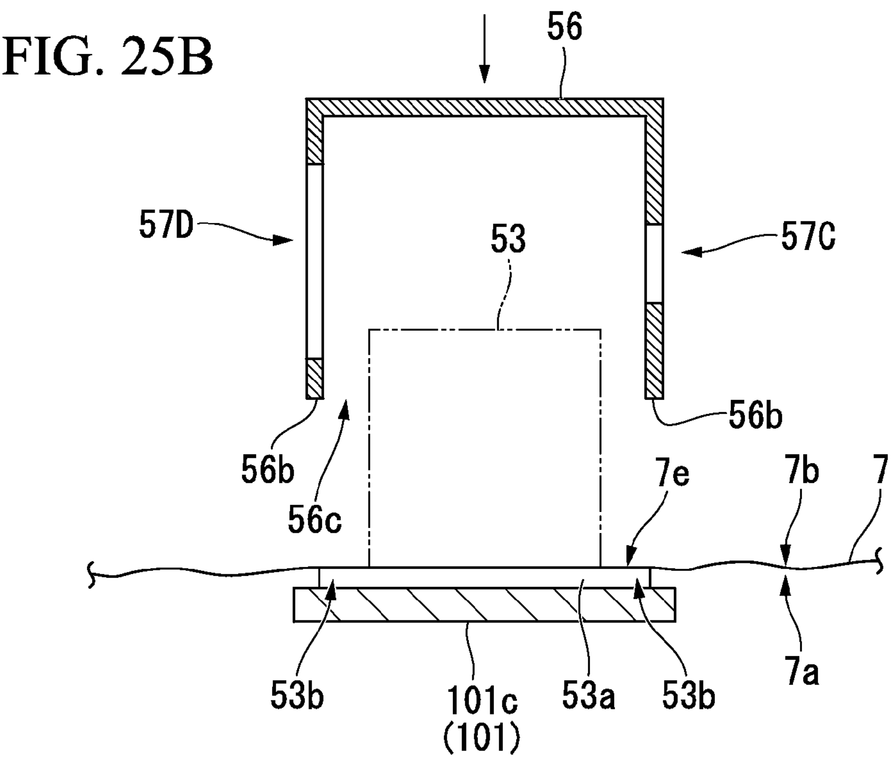
FIG. 25B is a schematic exploded view showing the relation between the coated housing and the drape used in the operation support device according to the third embodiment of the present invention and the modified example (the fourth modified example) thereof.

FIG. 25B is a schematic exploded view showing a relation between a coated housing and a drape used in an operation support device according to the present modified example (the fourth modified example) of the third embodiment of the present invention.

The present modified example is a modified example of the shielding member. In the present modified example, as shown in FIG. 25B, the drape hole 7*e* of the drape 7 according to the third embodiment is previously joined with the drape attachment section 53*b* of the support plate 53*a*, and further, only the drive unit cover 56 can be assembled to cover the surgical instrument driving unit 53.

Fourth Embodiment

Next, an operation support device of a fourth embodiment of the present invention will be described.

Figure 26:
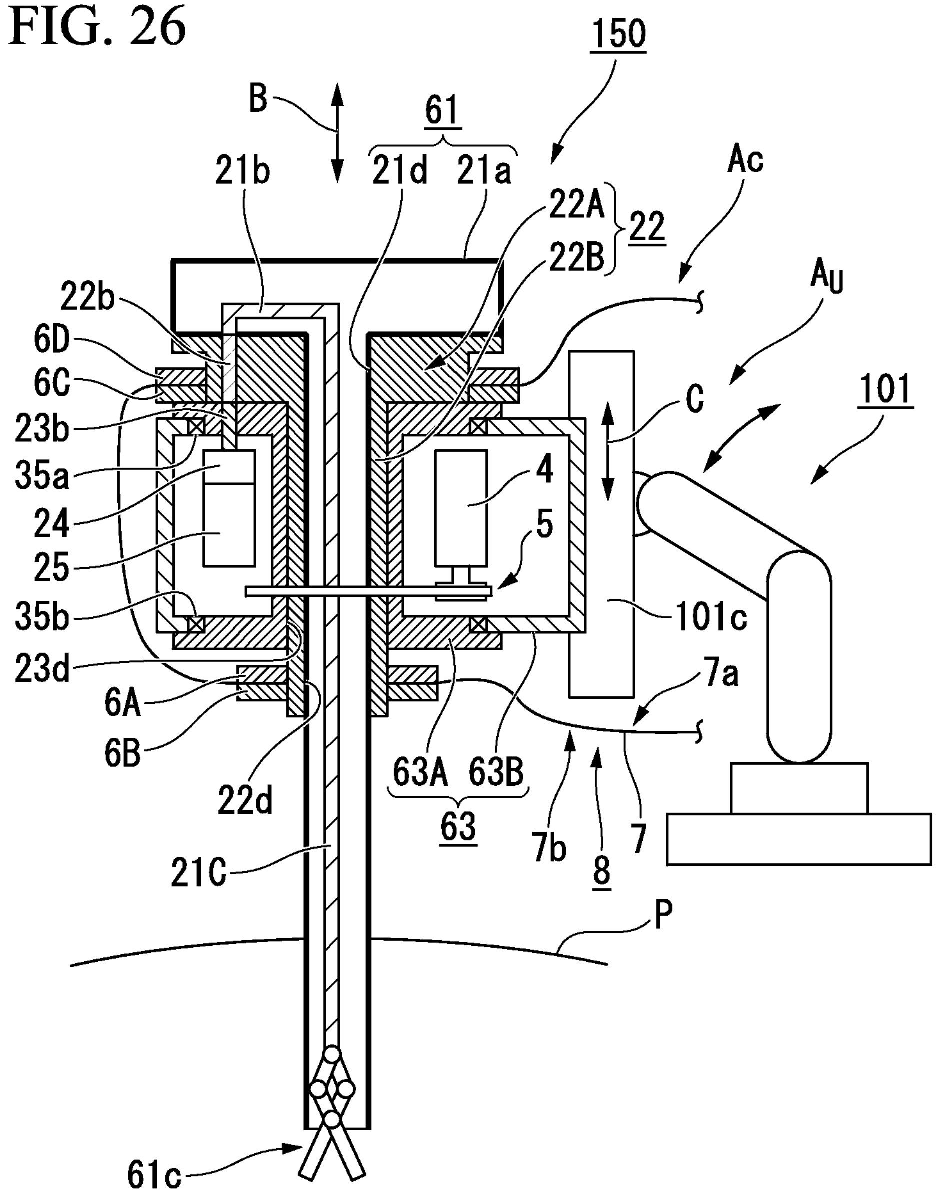
FIG. 26 is a schematic partial cross-sectional view showing a configuration of an operation support device according to a fourth embodiment of the present invention.

FIG. 26 is a schematic partial cross-sectional view showing a configuration of the operation support device according to the fourth embodiment of the present invention.

As shown in FIG. 26, an operation support device 150 according to the present embodiment includes a surgical instrument driving unit 63 (a driving force supply unit) and a surgical instrument unit 61, instead of the surgical instrument driving unit 23 and the surgical instrument unit 21 of the operation support device 120 according to the second embodiment, respectively.

In addition, the sterilization treatment is performed on the intermediate member 22 and the surgical instrument unit 61, and the sterilization treatment is not performed on the surgical instrument driving unit 63.

Hereinafter, the fourth embodiment will be described focusing on differences from the second embodiment.

The surgical instrument driving unit 63 has a configuration in which the linear driving force supply unit of the surgical instrument driving unit 23 according to the second embodiment is integrated as one system. The surgical instrument driving unit 63 is attached to the linear driving moving section 101*c* of the surgical instrument unit support section 101.

The surgical instrument driving unit 63 includes a support housing 63B having a through-hole formed at the linear driving moving section 101*c* and passing through opposite side surface portions in a direction parallel to the linear driving section 101*c*, and a shaft rotating member 63A rotatably fixed to the through-hole of the support housing 63B via bearings 35*a* and 35*b*.

The shaft rotating member 63A has flange portions formed at both end portions and fitted to inner rings of the bearings 35*a* and 35*b*. A through-hole portion 23*d* is formed in a tubular section sandwiched between the flange portions.

A motor 4 is fixed to the inside of the support housing 63B. The motor 4 is configured to rotate the shaft rotating member 63A via the transmission mechanism 5.

In addition, one motor unit 25 and one linear driving conversion unit 24 fixed to an outer circumference of a tubular body section of the shaft rotating member 63A via a fixing member (not shown) are installed in the support housing 63B.

Further, a driving force transmission shaft 23*b* connected to the linear driving conversion unit 24 is linearly disposed at the flange portions of the proximal end side of the shaft rotating member 63A.

The driving force transmission shaft 23*b* is detachably connected to the intermediate shaft 22*b* of the intermediate member 22, similar to the second embodiment.

The surgical instrument unit 61 includes a surgical instrument unit support 21*a* and a tubular section 21*d*, similar to the surgical instrument unit 21 according to the second embodiment. A forceps 61*c* (a surgical instrument) opened and closed by a link mechanism is installed at the distal end portion of the tubular section 21*d*.

A driving force transmission member 21*b* having the same configuration as in the second embodiment is installed in the surgical instrument unit support 21*a* and the tubular section 21*d*. The link mechanism of the forceps 61*c* is connected to the distal end of the driving force transmission member 21*b*.

According to the above-mentioned configuration, the operation support device 150 has the same action as in the operation support device 120 according to the second embodiment, except that the surgical instrument unit 61 is driven by the linear driving force of one system.

That is, as the same processes as in the second embodiment are performed and the drape assembly 8 and the intermediate member 22 are assembled with respect to the surgical instrument driving unit 63, the surgical instrument driving unit 63 and the surgical instrument unit support section 101 can be shielded and disposed in the unclean area $A_U$.

Further, as the same second connecting process as in the second embodiment is performed, in the clean area $A_C$, the sterilized surgical instrument unit 61 can be connected to the sterilized intermediate member 22.

In addition, as the shaft engagement process and the shaft engagement fixing release process according to the second embodiment are performed, the surgical instrument unit 61 can be attached and detached in the clean area $A_C$.

Accordingly, in the present embodiment, similar to the second embodiment, the assembly task of the surgical instrument unit 61 and the intermediate member 22 can be performed only in the clean area $A_C$. For this reason, exchange of the surgical instrument unit 61 during the operation can be rapidly and easily performed.

In addition, in the present embodiment, the surgical instrument unit 61 is inserted into and connected to the intermediate member 22. For this reason, for example, the surgical instrument unit 61 can be attached and detached toward the connecting body of the intermediate member 22 and the surgical instrument driving unit 23, disposed over the patient and supported by an arm, or the like, from an upper side. For this reason, the attachment/detachment task can be efficiently performed.

Fifth Embodiment

Next, an operation support device according to a fifth embodiment of the present invention will be described.

Figure 27:
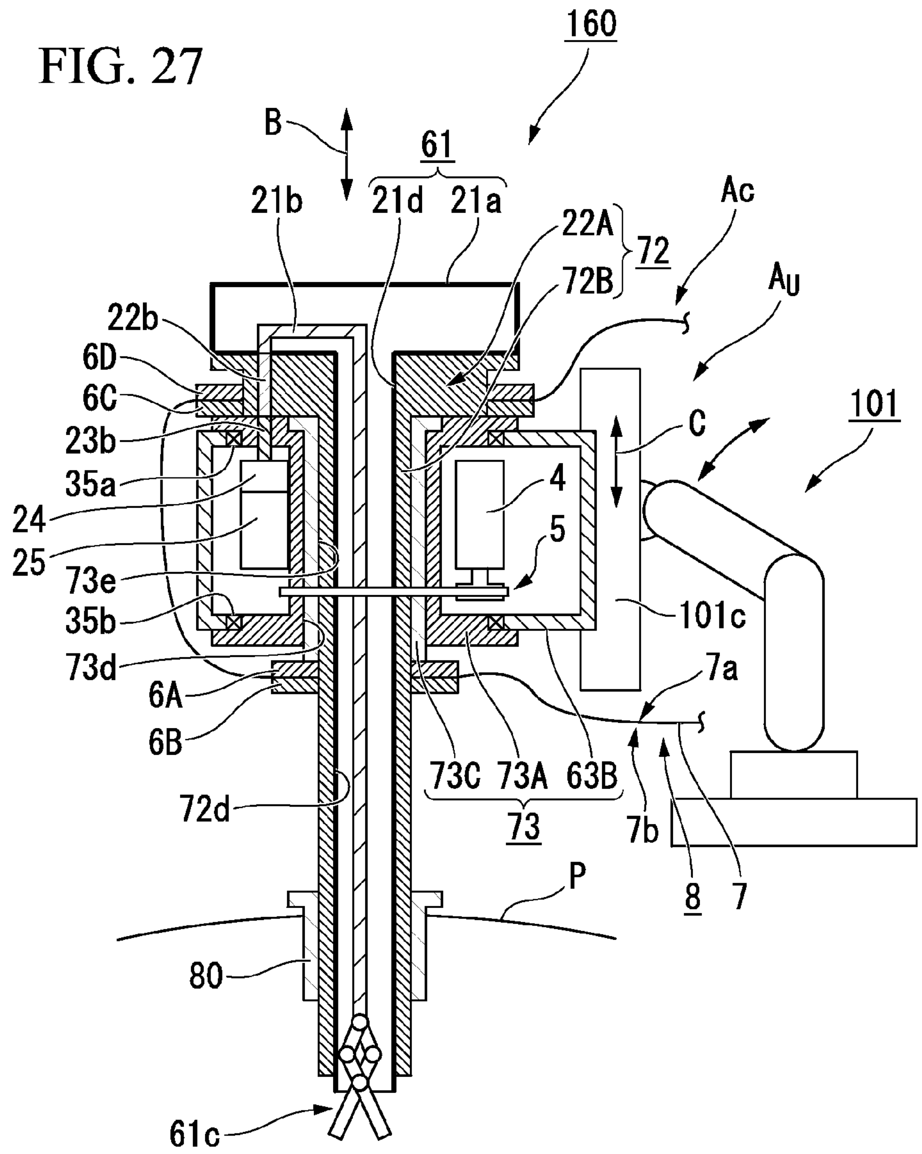
FIG. 27 is a schematic partial cross-sectional view showing a configuration of an operation support device according to a fifth embodiment of the present invention.

FIG. 27 is a schematic partial cross-sectional view showing a configuration of the operation support device according to the fifth embodiment of the present invention.

As shown in FIG. 27, an operation support device 160 according to the present embodiment includes a surgical instrument driving unit 73 and an intermediate member 72, instead of the surgical instrument driving unit 63 and the intermediate member 22 according to the fourth embodiment, respectively.

Hereinafter, the fifth embodiment will be described focusing on differences from the fourth embodiment.

The surgical instrument driving unit 73 includes a shaft rotating member 73A, instead of the shaft rotating member 63A of the surgical instrument driving unit 63 according to the fourth embodiment. Further, the surgical instrument driving unit 73 includes a sheath 73C (a sterilized sheath).

The shaft rotating member 73A includes an engaging hole 73*d* which the sheath 73C (to be described later) passes through and is engaged with, instead of the through-hole portion 23*d* according to the fourth embodiment. In the present embodiment, as an example, the engaging hole 73*d* has a shape in which a step-shaped section is formed at the proximal end side of the shaft rotating member 73A directed upward in a vertical direction, and a cylindrical surface having a diameter smaller than an outer diameter of the step-shaped section passes from the step-shaped section to the distal end.

The sheath 73C is a tubular member formed of a sterilizable material. In an outer circumferential section of the sheath 73C, a protrusion section engaged with the step-shaped section of the shaft rotating member 73A at least in the axial direction is formed at one end portion thereof. A cylindrical surface detachably fitted into the engaging hole 73*d* is formed from the protrusion section toward the other end side.

Accordingly, the sheath 73C is fitted in a state in which, when the sheath 73C is inserted into the engaging hole 73*d* of the shaft rotating member 73A from above, the protrusion section is fitted into the step-shaped section of the engaging hole 73*d* not to drop downward.

In addition, a through-hole 73*e* (a through-hole portion) constituted by a cylindrical surface having the same inner diameter as that of the through-hole portion 23*d* according to the fourth embodiment and formed to pass therethrough in the axial direction is formed at a center portion of the sheath 73C.

A length of the sheath 73C is substantially the same as that of the engaging hole 73*d*. Accordingly, in a state in which the sheath 73C on which the sterilization treatment has been performed is engaged with the engaging hole 73*d*, the sheath 73C passes through the shaft rotating member 73A in the axial direction and the engaging hole 73*d* is substantially covered from the inner circumference side.

In the above-mentioned assembly state, the engaging hole 73*d* is constituted by a through-hole portion through which the surgical instrument unit 61 passes and in which the sterilization treatment is performed.

The intermediate member 72 is distinguished from the fourth embodiment in that a tubular section 72B extending to a length in the axial direction substantially equal to a length of the surgical instrument unit 61 is provided, instead of the tubular section 22B of the intermediate member 22 according to the fourth embodiment.

For this reason, as shown in FIG. 27, when the surgical instrument unit 61 is inserted into a surgical instrument unit insertion hole 72*d* constituting an inner circumferential surface of the tubular section 72B, the tubular section 21*d* of the surgical instrument unit 61 is covered by the surgical instrument unit insertion hole 72*d* to substantially the distal end portion.

The operation support device 160 having the above-mentioned configuration is assembled in the same manner as in the fourth embodiment, except that, when the intermediate member 72 and the drape assembly 8 are connected to the surgical instrument driving unit 73, the sheath 73C is previously engaged with the engaging hole 73*d*. In addition, after assembly of the operation support device 160, in the clean area $A_C$, the surgical instrument unit 61 can be attached and detached in the same manner.

Accordingly, in the present embodiment, similar to the fourth embodiment, an assembly task of the surgical instrument unit 61 and the intermediate member 72 can be performed only in the clean area $A_C$. For this reason, exchange of the surgical instrument unit 61 during the operation can be rapidly and easily performed.

In addition, even in the present embodiment, the surgical instrument unit 61 is inserted into and connected to the intermediate member 72. For this reason, for example, the surgical instrument unit 61 can be attached and detached toward the connecting body of the intermediate member 72 and the surgical instrument driving unit 73, disposed over the patient and supported by an arm, or the like, from an upper side. For this reason, the attachment/detachment task can be efficiently performed.

In particular, in the present embodiment, in a state in which the surgical instrument unit 61 and the intermediate member 72 are separated from each other, in the clean area $A_C$, the sheath 73C after use can be separated from the shaft rotating member 73A, and replaced with a clean sheath 73C on which the sterilization treatment has been performed. In addition, the separated sheath 73C may be reused after the sterilization treatment, or may be used as a disposable sheath.

In addition, in the present embodiment, in an assembly state of the operation support device 160, the tubular section 21*d* of the surgical instrument unit 61 is received in the clean area in the intermediate member 72. For this reason, in comparison with the case in which the tubular section 21*d* is exposed from the intermediate member 22 as described in the fourth embodiment, cleanliness in use can be easily maintained.

Further, in the present embodiment, the clean sheath 73C on which the sterilization treatment has been performed is engaged with the unclean shaft rotating member 73A. For this reason, in the tubular section 72B of the intermediate member 72 inserted into the sheath 73C, cleanliness of a portion protruding from the sheath 73C is also maintained.

In the first to fourth embodiments, the outer circumferential surface of the tubular section of the intermediate member inserted into the shaft rotating member is brought in contact with the unclean shaft rotating member and contaminated. However, in the present embodiment, an outer circumferential surface 72*a* of the tubular section 72B of the intermediate member 72 is configured to contact the clean sheath 73C upon attachment/detachment. For this reason, in the tubular section 72B of the intermediate member 72, a portion protruding from the drape rings 6A and 6B is also clean.

For example, when an operation in the body of the patient P such as an operation by an endoscope is performed, as shown in FIG. 27, a trocar 80 is installed at an initial incision area formed at a body surface of the patient P, and various treatment tools and surgical instruments are inserted.

In the present embodiment, a portion protruding from the drape rings 6A and 6B in the tubular section 72B of the intermediate member 72 is also clean. For this reason, the tubular section 72B of the intermediate member 72 is also collected and inserted into the body of the patient P through the trocar 80.

When the forceps 61*c*, which is the surgical instrument of the surgical instrument unit 61, is inserted into the body in this state, the forceps 61*c* can be inserted into the body through the inside of the tubular section 72B of the intermediate member 72 with no contact with the external air. In addition, even when the surgical instrument is exchanged with a new one, the surgical instrument can be exchanged through the clean area in the tubular section 72B with no contact with the external air.

Accordingly, since the surgical instrument unit 61 is always exchanged in the clean area, safety against contamination is increased.

In addition, in the description of the respective embodiments and modified examples, the example of the case in which the surgical instrument unit support section 101 has the multi-joint arm 101*b* and the linear driving moving section 101*c* has been described. However, the same movement as described above may be manually performed.

Hereinabove, while preferred embodiments of the present invention have been described, the present invention is not limited to the embodiments. Additions, omissions, substitutions, and other modifications can be made to the present invention without departing from the spirit and scope of the present invention. The present invention is not limited to the above-mentioned description, and is only limited by the appended claims.

What is claimed is:

1. An operation support device having a surgical instrument unit and a surgical instrument unit support section configured to detachably support the surgical instrument unit, the operation support device comprising:

a sterilizable intermediate member rotatably connected to the surgical instrument support section and configured to detachably hold the surgical instrument unit;

a sterilizable drape having at least one hole portion, the hole portion being engaged with the intermediate member; and a driving force supply unit installed at the surgical instrument support section and configured to supply a driving force to the surgical instrument unit via the intermediate member, wherein a first space and a second space are formed by an assembly constituted by the drape and the intermediate member engaged with the hole portion of the drape as a boundary, the intermediate member is detachably connected to the surgical instrument support section at a side of the first space, the intermediate member detachably holds the surgical instrument unit at a side of the second space, and the driving force supply unit and the surgical instrument support section are disposed in the first space.

2. The operation support device according to claim 1, wherein, as at least the intermediate member is rotated, a rotary driving force is supplied to the surgical instrument unit.

3. The operation support device according to claim 1, wherein at least a pair of hole portions are provided, and the intermediate member has a through-hole portion, into which the surgical instrument unit is inserted, provided to pass through the pair of hole portions and constituting a part of the second space.

4. The operation support device according to claim 3, wherein the through-hole portion has a detachable sterilized sheath.

5. The operation support device according to claim 1, wherein the driving force supply unit has at least a linear driving force supply unit configured to advance and retract a drive shaft section in a certain direction to supply a linear driving force, the intermediate member has at least a linear driving transmission shaft section movably installed in the same direction as the drive shaft section, and the surgical instrument unit is driven by the linear driving force received from the linear driving transmission shaft section.

6. The operation support device according to claim 1, wherein the intermediate member and the surgical instrument unit are detachably installed to advance and retract with respect to the hole portion in a certain axial direction.

7. The operation support device according to claim 6, wherein the intermediate member and the driving force supply unit are detachably installed in the axial direction.

8. The operation support device according to claim 1, wherein the drape is provided with a frame member joined with the drape, and the hole portion on which the intermediate member is mounted is formed at an inner circumferential portion of the frame member.

9. The operation support device according to claim 8, wherein the frame member joined with the drape is detachably installed with respect to the driving force transmission section.

10. The operation support device according to claim 1, wherein the drape is provided with a coated housing joined with the drape, and the hole portion through which the intermediate member is capable of passing is formed at the coated housing.

11. The operation support device according to claim 10, wherein the coated housing joined with the drape is detachably installed with respect to the driving force transmission section.

12. An assembly method of an operation support device having a surgical instrument unit and a surgical instrument unit support section configured to detachably support the surgical instrument unit, wherein the operation support device comprises:

a sterilizable intermediate member rotatably connected to the surgical instrument support section and configured to detachably hold the surgical instrument unit;

a sterilizable shielding member having at least one hole portion engaged with the intermediate member; and a driving force supply unit installed at the surgical instrument support section and configured to supply a driving force to the surgical instrument unit via the intermediate member, the assembly method comprising:

a shielding member disposition process of disposing the shielding member to cover the driving force supply unit and the surgical instrument support section;

a first connecting process of engaging the hole portion of the shielding member with the intermediate member to form an assembly, positioning the driving force supply unit and the surgical instrument support section in a first space using the assembly as a boundary, and detachably connecting the intermediate member and the surgical instrument support section in a side of the first space; and a second connecting process of detachably holding the intermediate member and the surgical instrument unit in a side of a second space opposite to the first space using the assembly as a boundary.

* * * * *